US 6,979,556 B2
(12) United States Patent
Simmons et al.

(10) Patent No.: US 6,979,556 B2
(45) Date of Patent: Dec. 27, 2005

(54) SEPARATE-CISTRON CONTRUCTS FOR SECRETION OF AGLYCOSYLATED ANTIBODIES FROM PROKARYOTES

(75) Inventors: Laura C. Simmons, Burlingame, CA (US); Laura Klimowski, Salt Lake City, UT (US); Dorothea Reilly, San Francisco, CA (US); Daniel G. Yansura, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 157 days.

(21) Appl. No.: 10/020,786

(22) Filed: Dec. 13, 2001

(65) Prior Publication Data

US 2003/0073164 A1 Apr. 17, 2003

Related U.S. Application Data

(60) Provisional application No. 60/256,164, filed on Dec. 14, 2000.

(51) Int. Cl.[7] .......... C12N 15/09; C12N 15/00; C12P 21/06; C07K 16/00; C07H 21/04
(52) U.S. Cl. .......... 435/69.1; 435/69.7; 435/252.3; 435/471; 435/252.33; 435/69.6; 536/23.1; 536/23.4; 530/387.1
(58) Field of Search .......... 435/69.6, 69.7, 435/69.1, 252.3, 252.33, 471; 536/23.1, 23.4; 530/387.1

(56) References Cited

U.S. PATENT DOCUMENTS

| 4,816,567 A | 3/1989 | Cabilly et al. |
| 5,264,365 A | 11/1993 | Georgiou et al. |
| 5,500,362 A | 3/1996 | Robinson et al. |
| 5,508,192 A | 4/1996 | Georgiou et al. |
| 5,585,097 A | 12/1996 | Bolt et al. |
| 5,639,635 A | 6/1997 | Joly et al. |
| 5,648,237 A | 7/1997 | Carter |
| 5,747,662 A | 5/1998 | Simmons et al. |
| 5,821,337 A | 10/1998 | Carter et al. |
| 5,840,523 A | 11/1998 | Simmons et al. |
| 6,008,023 A | 12/1999 | Opper et al. |
| 6,027,888 A | 2/2000 | Georgiou et al. |
| 6,083,715 A | 7/2000 | Georgiou et al. |
| 6,455,279 B1 | 9/2002 | Ambrosius et al. |
| 6,602,688 B1 | 8/2003 | Opper et al. |

FOREIGN PATENT DOCUMENTS

| EP | 154316 | 9/1985 |
| EP | 401384 | 12/1990 |
| EP | 0 731 167 | 9/1996 |
| WO | WO 93/07896 | 4/1993 |
| WO | WO 93/08300 | 4/1993 |
| WO | WO 93/17715 | 9/1993 |
| WO | WO 93/19196 | 9/1993 |
| WO | WO 98/48837 | 11/1998 |

OTHER PUBLICATIONS

Arie et al., "Chaperone Function of FkpA, A Heat Shock Prolyl Isomerase, in the Periplasm of *Escherichia coli.*" *Molecular Microbiology.* 39(1):199–210 (2001).

Armour et al., "Recombinant Human IgG Molecules Lacking FCγ Receptor I Binding and Monocyte Triggering Activities." *European Journal of Immunology.* 29(8):2613–2624 (Aug. 1999).

(Continued)

Primary Examiner—Gerry Leffers
(74) Attorney, Agent, or Firm—Merchant & Gould P.C.

(57) ABSTRACT

The present invention provides methods and compositions for improved expression and production of recombinant antibodies in prokaryotic expression systems. Particularly contemplated are prokaryotic expression and production of full length aglycosylated antibodies. The antibody products of the invention can be used in various aspects of biological research, diagnosis and medical treatment.

27 Claims, 21 Drawing Sheets

OTHER PUBLICATIONS

Bachmann., "Derivations and Genotypes of Some Mutant Derivatives of *Escherichia coli* K–12." *Escherichia coli and Salmonella Typhimurium: Cellular and Molecular Biology*. (Washington, DC: American Society for Microbiology.), Chapter 72, 2:1190–1219 (1987).

Barbas III et al., "In Vitro Evolution of a Neutralizing Human Antibody to Human Immunodeficiency Virus Type 1 to Enhance Affinity and Broaden Strain Cross–Reactivity." *Proc. Natl. Acad. Sci. USA* 91(9):3809–3813 (Apr. 26, 1994).

Bass et al., "Hormone Phage: An Enrichment Method for Variant Proteins with Altered Binding Properties" *Proteins: Structure, Function, and Genetics* 8(4):309–314 (1990).

Bothmann and Pluckthun., "The Periplasmic *Escherichia coli* Peptidylprolyl cis, trans–Isomerase FkpA." *J. Bio. Chem.* 275(22):17100–17105 (Jun. 2000).

Capel et al., "Heterogeneity of HUman IgG Fc Receptors." *Immunomethods.* 4:25–34 (1994).

Carter et al., "High Level *Escherichia coli* Expression and Production of a Bivalent Humanized Antibody Fragment." *Bio/Technology.* 10(2):163–7 (Feb. 1992).

Carter et al., "Humanization of an Anti–p185$^{HER2}$ Antibody For Human Cancer Therapy" *Proc. Natl. Acad. Sci. USA* 89:4285–4289 (May 1992).

Chang et al., "High–Level Secretion of Human Growth Hormone by *Escherichia coli.*" *Gene.* 55:189–196 (1987).

Chari et al., "Immunoconjugates Containing Novel Maytansinoids: Promising Anticancer Drugs." *Cancer Research.* 52:127–131 (Jan. 1992).

Chen et al., "Chaperone Activity of DsbC." *J. Bio. Chem.* 274(28):19601–19605 (Jul. 1999).

Chothia and Lesk, "Canonical Structures for the Hypervariable Regions of Immunoglobulins" *J. Mol. Biol* 196:901–917 (1987).

Clynes et al., "Fc Receptors Are Required in Passive and Active Immunity to Melanoma." *Proc. Natl. Acad. Sci. USA* 95(2):652–656 (Jan. 20, 1998).

Cunningham and Wells, "High–Resolution Epitope Mapping of hGH–Receptor Interactions by Alanine–Scanning Mutagenesis" *Science* 244:1081–1085 (1989).

Daeron, M., "Fc Receptor Biology" *Annual Review of Immunology* 15:203–234 (1997).

de Haas et al., "Fcγ Receptors of Phagocytes." *J. of Laboratory Clinical Medicine.* 126:330–341 (1995).

Eigenbrot et al., "X–Ray Structures of Fragments From Binding and Nonbinding Versions of a Humanized Anti–CD18 Antibody: Structural Indications of the Key Role of $V_H$ Residues 59 to 65" *Proteins: Structure, Function, and Genetics* 18:49–62 (1994).

Fendly, B.M. et al., "Characterization of Murine Monoclonal Antibodies Reactive to Either the Human Epidermal Growth Factor Receptor or HER2/neu Gene Product" *Cancer Research* 50:1550–1558 (Mar. 1, 1990).

Francisco et al., "Agonistic Properties and in Vivo Antitumor Activity of the Anti–CD40 Antibody SGN–14." *Cancer Research.* 60:3225–3231 (Jun. 2000).

Friend et al., "Phase I Study of an Engineered Aglycosylated Humanized CD3 Antibody in Renal Transplant Rejection." *Transplantation.* 68(11):1632–1637 (Dec. 15, 1999).

Guyer et al., "Immunoglobulin Binding by Mouse Intestinal Epithelial Cell Receptors." *J. Immunol.* 117(2):587–593 (1976).

Hara et al., "Overproduction of Penicillin–Binding Protein 7 Suppresses Thermosensitive Growth Defect at Low Osmolarity Due to an spr Mutation of *Escherichia coli.*" *Micro. Drug Resistance.* 2(1):63–72 (1996).

Harris., "Therapeutic Monoclonals." *Biochemical Society Transactions* 23:1035–1038 (1995).

Hawkins et al., "Selection of Phage Antibodies by Binding Affinity Mimicking Affinity Maturation" *J. Mol. Biol.* 226:889–896 (1992).

Henzel et al., "Analysis of Two–Dimensional Gel Proteins by Mass Spectrometry and Microsequencing." *Methods: A Companion to Methods Enzymol.* 6:239–247 (1994).

Hurle and Gross., "Protein Engineering Techniques for Antibody Humanization." *Curr. Op. Biotech.* 5:428–433 (1994).

Idusogie et al., "Mapping of the Clq Binding Site on Rituxan, A Chimeric Antibody with a Human IgG1 Pc." *J. Immunol.* 164:4178–4184 (2000).

Isaacs et al., "A Therapeutic Human IgG4 Monoclonal Antibody that Depletes Target Cells in Humans." *Clin. Exp. Immunol.* 106:427–433 (1996).

Jackson et al., "In Vitro Antibody Maturation." *J. Immunol.* 154(7):3310–3319 (1995).

Jones et al., "Replacing the Complementarity–Determining Regions in a Human Antibody with those from a Mouse" *Nature* 321:522–525 (May 29, 1986).

Kikuchi et al., "The Nucleotide Sequence of the Promoter and the Amino–Terminal Region of Alkaline Phosphatase Structural Gene (phoA) of *Escherichia coli.*" *Nucleic Acids Research.* 9(21):5671–5678 (1981).

Kim et al., "Localization of the Site of the Murine IgG1 Molecule That is Involved in Binding to the Murine Intestinal Fc Receptor." *European Journal of Immunology.* 24:2429–2434 (1994).

Kipriyanov and Little., "Generation of Recombinant Antibodies." *Mol. Biotech.* 12:173–201 (1999).

Kostelny et al., "Formation of a Bispecific Antibody by the Use of Leucine Zippers" *Journal of Immunology* 148(5):1547–1553 (1992).

Lindmark et al., "Binding of Immunoglobulins to Protein A and Immunoglobulin Levels in Mammalian Sera." *J. Immunol. Meth.* 62:1–13 (1983).

Marks et al., "By–Passing Immunization: Building High Affinity Human Antibodies by Chain Shuffling" *Bio/Technology* 10:779–783 (1992).

Matsudaira, P., "Sequence from Picomole Quantities of Proteins Electroblotted onto Polyvinylidene Difluoride Membranes" *Journal of Biological Chemistry* 262(21):10035–10038 (Jul. 25, 1987).

Milstein and Cuello, "Hybrid Hybridomas and Their Use in Immunohistochemistry" *Nature* 305:537–540 (Oct. 1983).

Morrison et al., "Chimeric Human Antibody Molecules: Mouse Antigen–Binding Domains with Human Constant Region Domains." *Proc. Natl. Acad. Sci. USA* 81:6851–6855 (Nov. 1984).

Picken et al., "Nucleotide Sequence of the Gene for Heat-Stable Enterotoxin II of *Escherichia coli.*" *Infection and Immunity.* 42(1):269–275 (1983).

Pluckthun and Pack., "New Protein Engineering Approaches to Multivalent and Bispecific Antibody Fragments." *Immunotechnology.* 3:83–105 (Jun. 1997).

Pluckthun et al., "Producing Antibodies in *Escherichia coli*: From PCR to Fermentation." *Antibody Engineering: A Practical Approach*, Oxford Press, Chapter 10, pps. 203–252 (1996).

Pluckthun., "Antibodies From *Escherichia coli*." *The Pharmcol. of Monoclonal Antibodies: Handbook of Exp. Pharmcol.*, Rosenberg and Moore, eds., Berlin:Springer–Verlag, Chapter 11, vol. 3:269–315 (1994).

Presta et al., "Humanization of an Anti–Vascular Endothelial Growth Factor Monoclonal Antibody for the Therapy of Solid Tumors and Other Disorders" *Cancer Research* 57(20):4593–4599 (Oct. 15, 1997).

Presta et al., "Humanization of an Antibody Directed Against IgE" *J. Immunol.* 151(5):2623–2632 (Sep. 1, 1993).

Presta, L., "Antibody Engineering" *Curr. Op. Struct. Biol.* 2:593–596 (1992).

Proba et al., "Functional Antibody Single–Chain Fragments From the Cytoplasm of *Escherichia coli*: Influence of Thioredoxin Reductase (TrxB)." *Gene.* 159:203–207 (1995).

Ramm and Pluckthun., "The Periplasmic *Escherichia coli* Peptidylprolyl cis, trans Isomerase FkpA." *J. Bio. Chem.* 275:17106–17113 (2000).

Ravetch and Kinet, "Fc Receptors" *Annual Review of Immunology* 9:457–492 (1991).

Reddy et al., "Elimination of Fc Receptor–Dependent Effector Functions of a Modified IgG4 Monoclonal Antibody to Human CD4." *J. Immunol.* 164:1925–1933 (2000).

Riechmann et al., "Reshaping Human Antibodies for Therapy" *Nature* 332:323–327 (Mar. 24, 1988).

Schier et al., "Identification of Functional and Structural Amino–Acid Residues by Parsimonious Mutagenesis." *Gene.* 169:147–155 (1996).

Scholtissek and Grosse, "A Cloning Cartridge of $\lambda$ $t_o$ Terminator." *Nucl. Acids Res.* 15(7):3185 (1987).

Siebenlist et al., "*E. Coli* RNA Polymerase Interacts Homologously with Two Different Promoters" *Cell* 20:269–281 (Jun. 1980).

Simmons and Yansura., "Translational Level is a Critical Factor for the Secretion of Heterologous Proteins in *Escherichia coli*." *Nature Biotechnology.* 14:629–634 (May 1996).

Sims et al., "A Humanized CD18 Antibody Can Block Function Without Cell Destruction" *The Journal of Immunology* 151(4):2296–2308 (Aug. 1993).

Sutcliffe, J., "Complete Nucleotide Sequence of the *Escherichia coli* Plasmid pBR322." *Cold Spring Harbor Symposia on Quantitative Biology.* 43:77–90 (1979).

Thompson et al., "A Fully Human Antibody Neutralising Biologically Active Human TGFβ2 for Use in Therapy." *J. Immunol. Meth.* 227:17–29 (1999).

Vaswani and Hamilton., "Humanized Antibodies as Potential Therapeutic Drugs." *Ann. Allergy Asthma Immunol.* 81:105–119 (Aug. 1998).

Verhoeyen, M. et al., "Reshaping Human Antibodies: Grafting an Antilysozyme Activity" *Science* 239:1534–1536 (Mar. 25, 1988).

Vitetta et al., "Redesigning Nature's Poisons to Create Anti–Tumor Reagents" *Science* 238:1098–1104 (1987.

Yanotsky et al., "The Complete Nucleotide Sequence of the Tryptophan Operon of *Escherichia coli*." *Nucleic Acids Research* 9(24):6647–6668 (Nov. 1981).

Yansura and Simmons, "Nucleotide Sequence Selection for Increased Expression of Heterologous Genes in *Escherichia coli*." *Methods: A Companion to Methods in Enzymology.* 4(2):151–158 (1992).

Yelton et al., "Affinity Maturation of the BR96 Anti–Carcinoma Antibody by Codon–Based Mutagenesis." *J. Immunol.* 155:1994–2004 (1995).

Zemel–Dreasen and Zamir., "Secretion and Processing of an Immunoglobulin Light Chain in *Escherichia coli*." *Gene.* 27(3):315–322 (1984).

Boyd et al., "The Effect of the Removal of Sialic Acid, Galactose and Total Carbohydrate on the Functional Activity of Campath–1H." *Molecular Immunology* 32:1311–1318 (1995).

Schmiedl et al. *Antibody Engineering*, Berlin Heidelberg: Springer pps. 257 (2001).

Simmons, L. et al., "Expression of full–length immunoglobins in *Escerichia coli*: Rapid and efficient production of aglycosylated antibodies" *Journal of Immunological Methods* 263:133–147 (2002).

Sibila, T. et al., "A Structured Model for Monoclonal Antibody Synthesis in Exponentially Growing and Stationary Phase Hybridoma Cells" *Biotechnology and Bioengineering* 37:210–226 (1991).

Scharff, M.D. et al., "Synthesis and Assembly of Immunoglobulin Polypeptide Chains" *Progr. Allergy* 14:37–80 (1970).

Lo, K. et al., "Expression and secretion of an assembled tetrameric CH2–deleted antibody in *E. coli*", *Hum. Antibod. Hybridomas*, 3:123–128 (Jul. 1992).

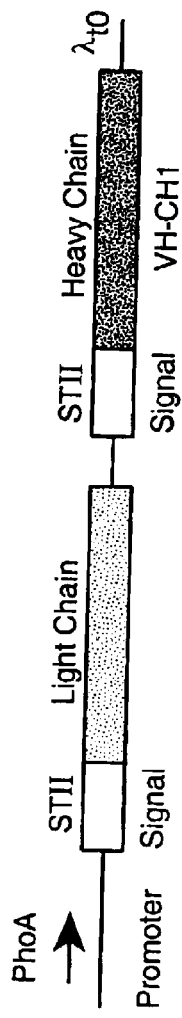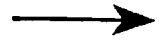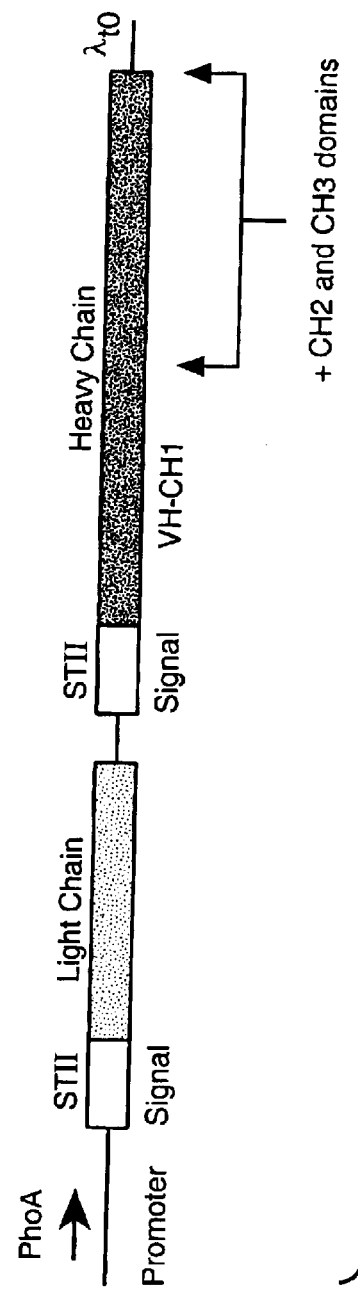
FIG._1

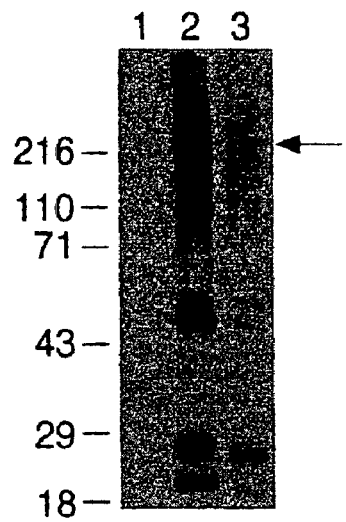
FIG._2
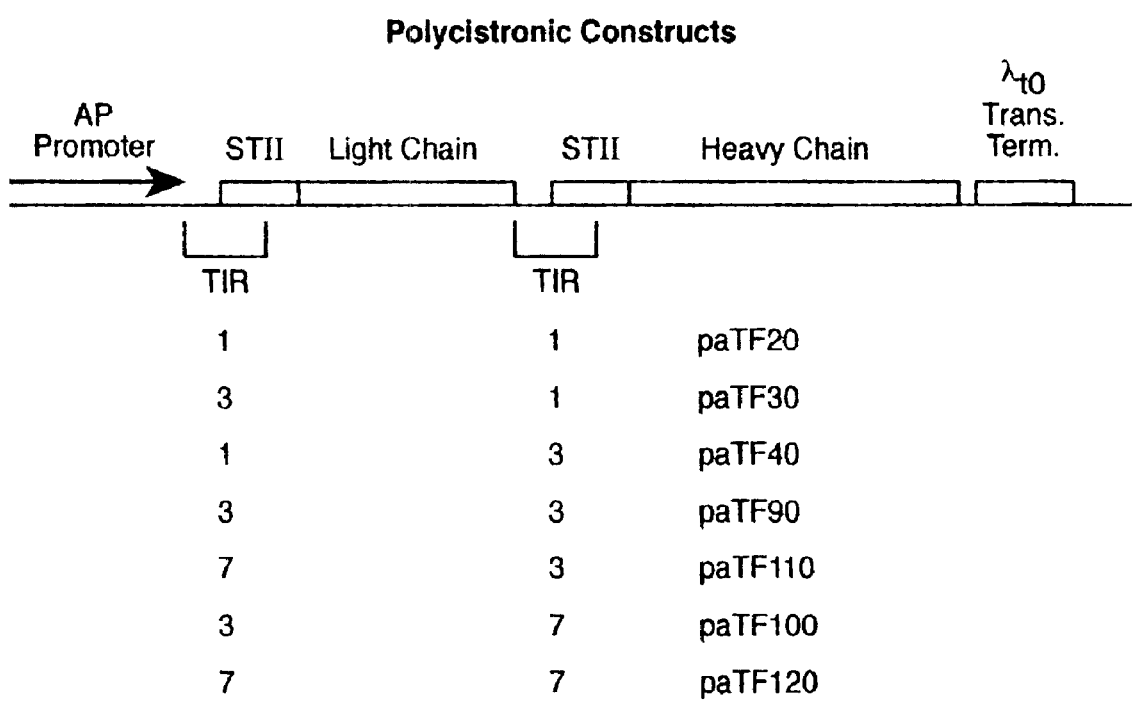
FIG._3

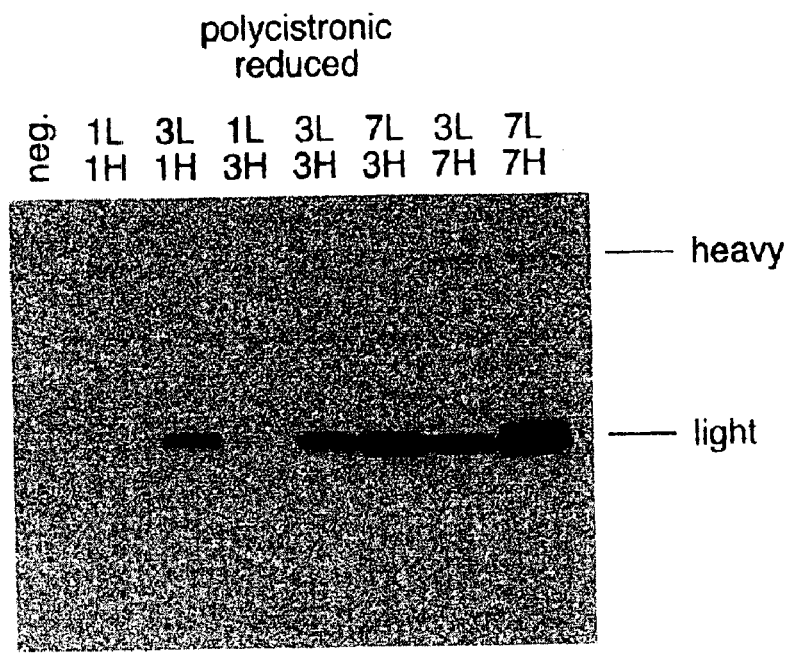
FIG._4A
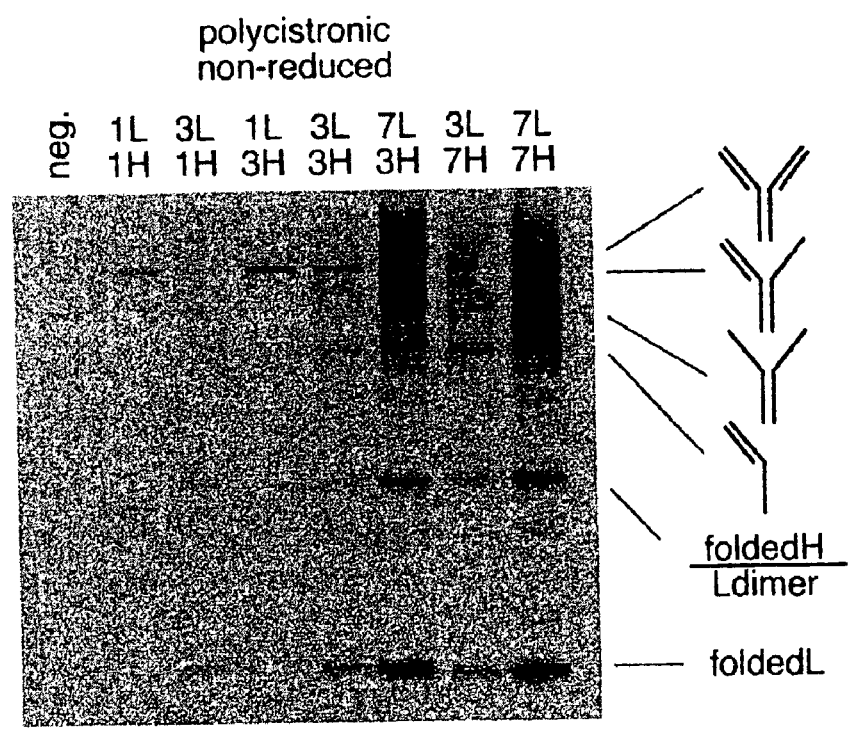
FIG._4B

Light Chain Constructions
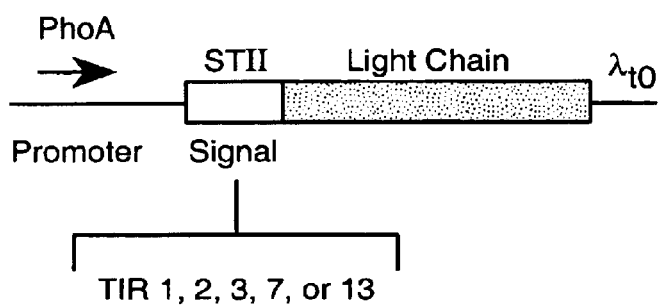
Heavy Chain Constructions
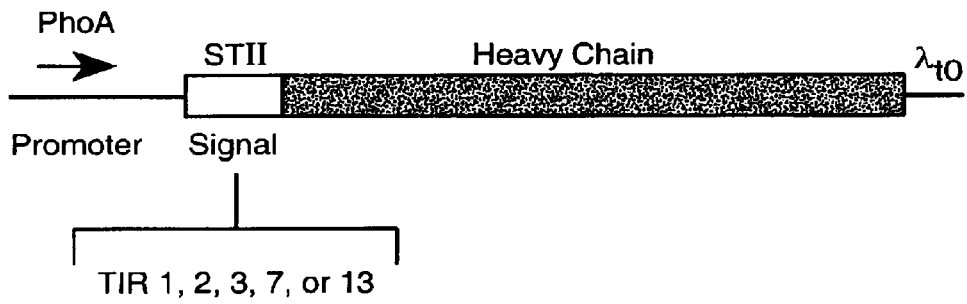
FIG._5

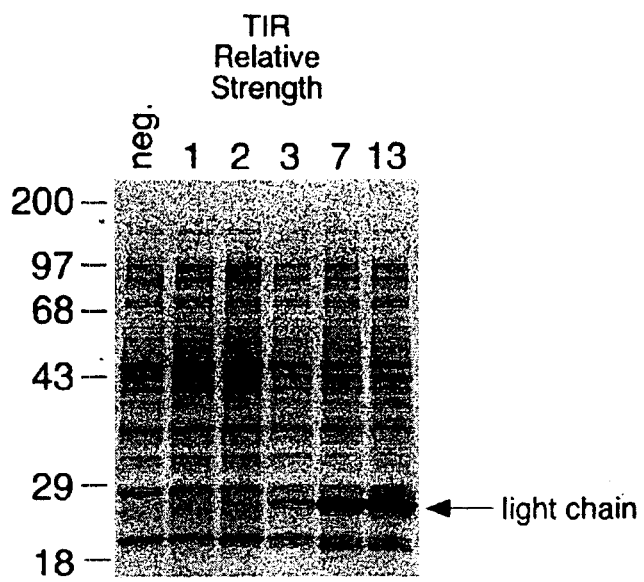
FIG._6A
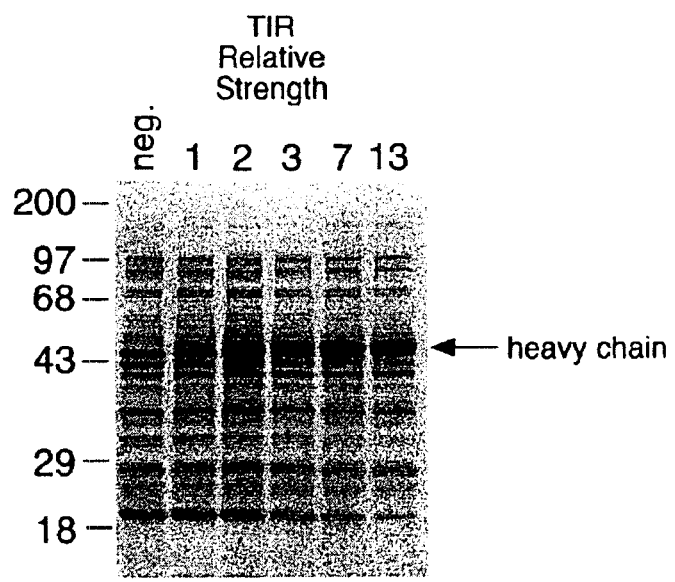
FIG._6B
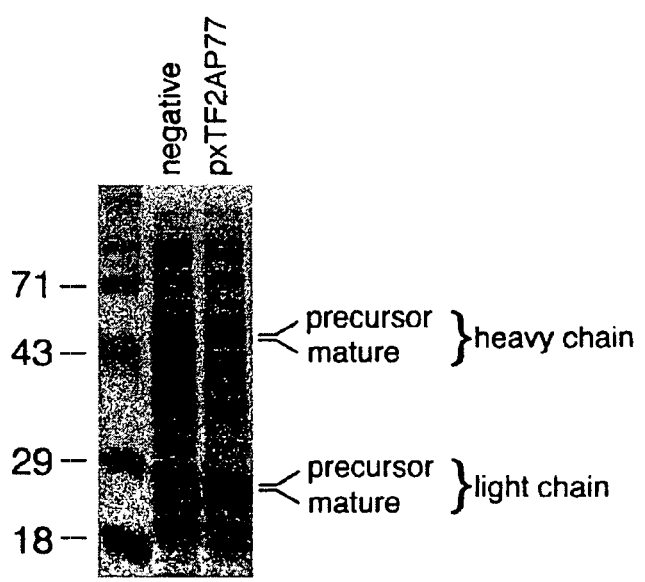
FIG._8

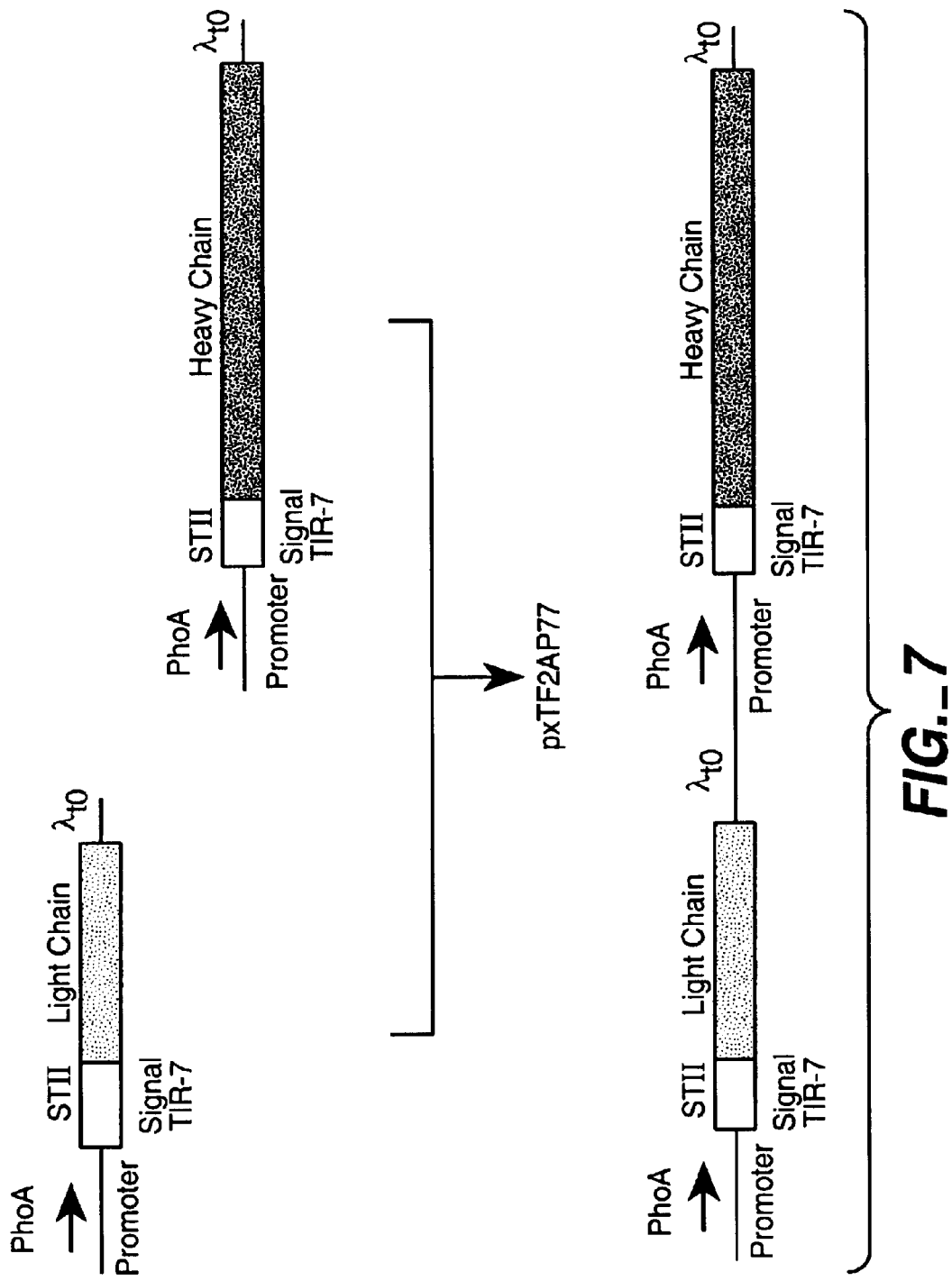
FIG._7

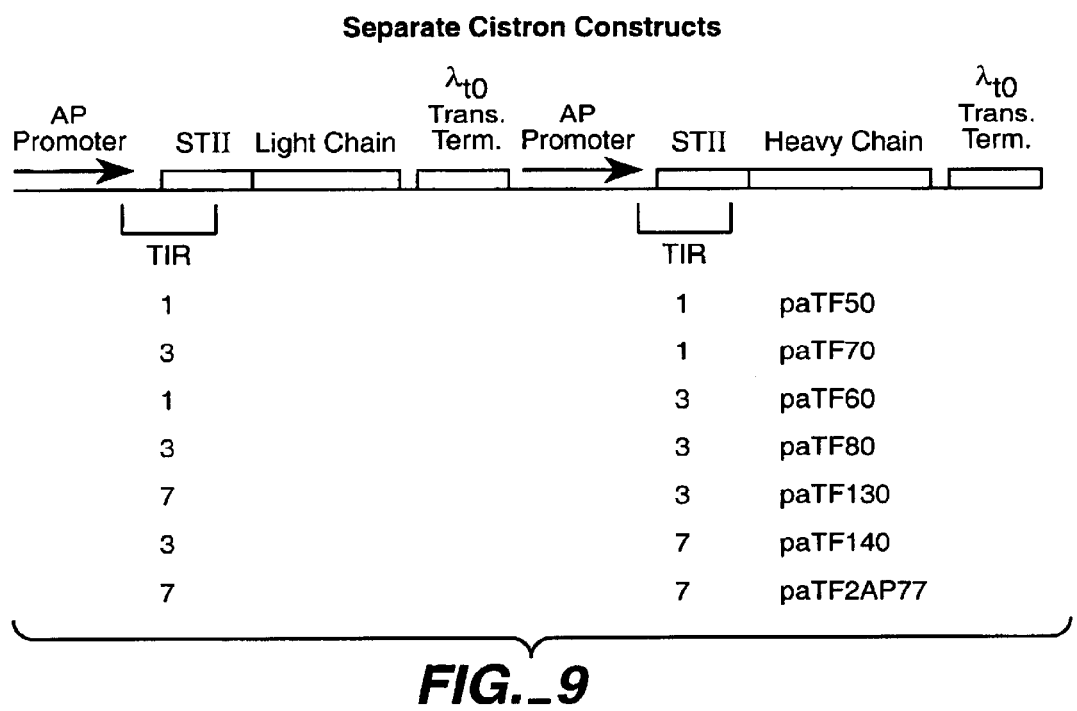
FIG._9

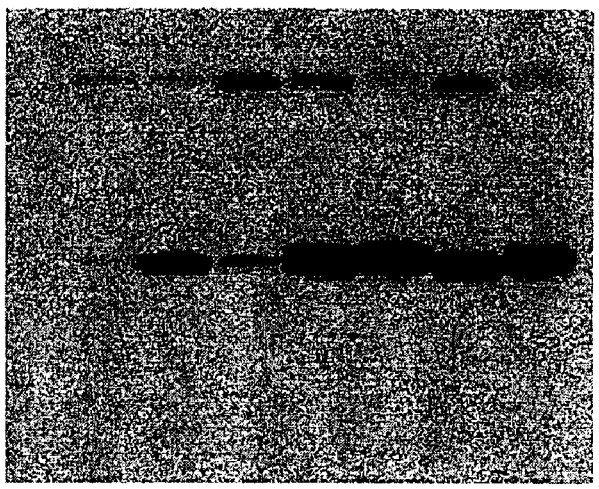
FIG._10A
separate cistrons reduced
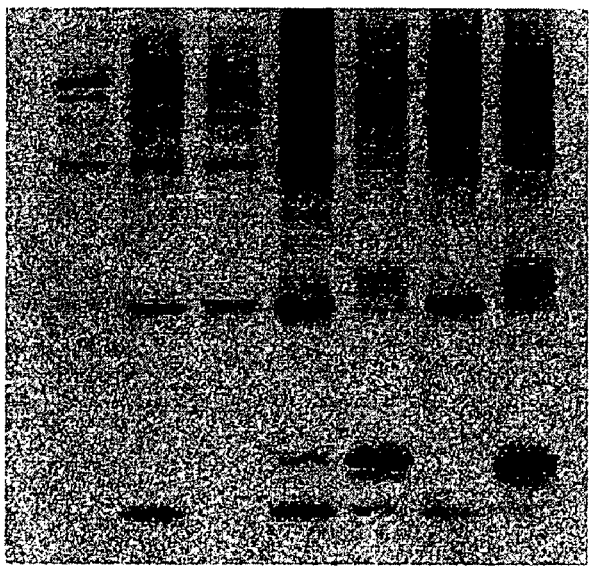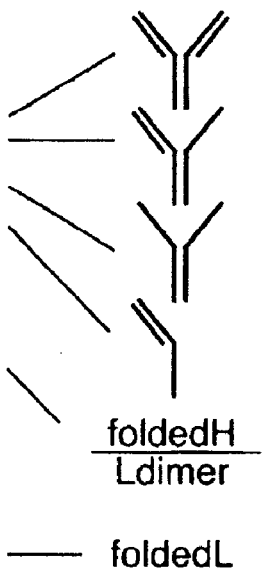
FIG._10B
separate cistrons non-reduced

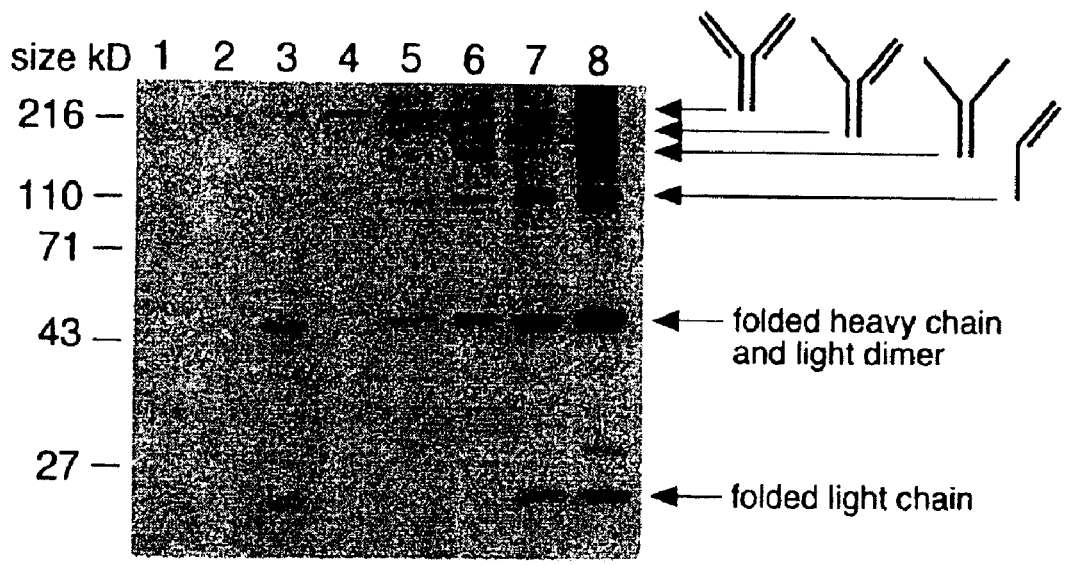
1) negative control
2) TIR 1-light, TIR 1-heavy, polycistronic
3) TIR 3-light, TIR 1-heavy, polycistronic
4) TIR 1-light, TIR 3-heavy, polycistronic
5) TIR 1-light, TIR 1-heavy, separate cistrons
6) TIR 1-light, TIR 3-heavy, separate cistrons
7) TIR 3-light, TIR 1-heavy, separate cistrons
8) TIR 3-light, TIR 3-heavy, separate cistrons
FIG._11
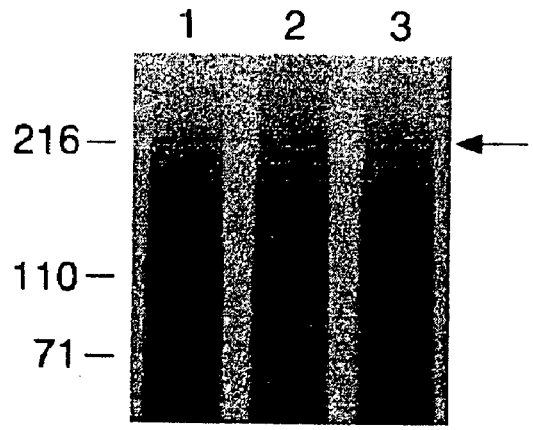
FIG._12

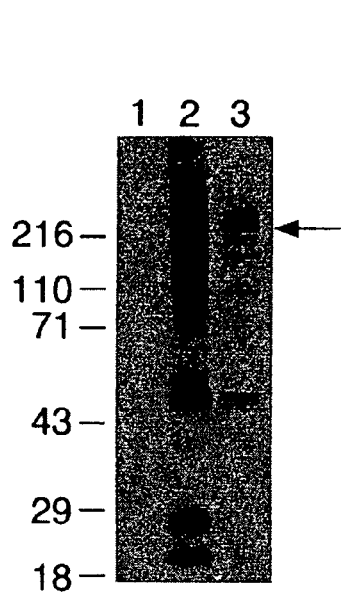
FIG._13
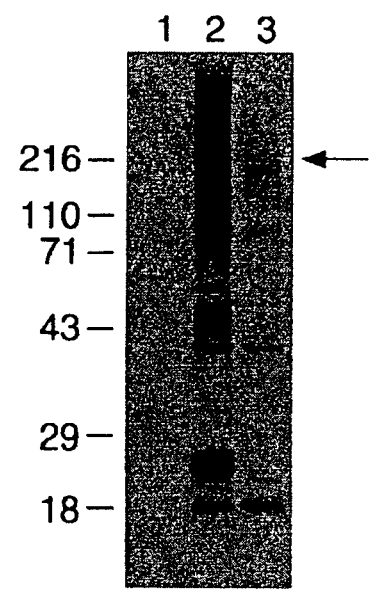
FIG._14
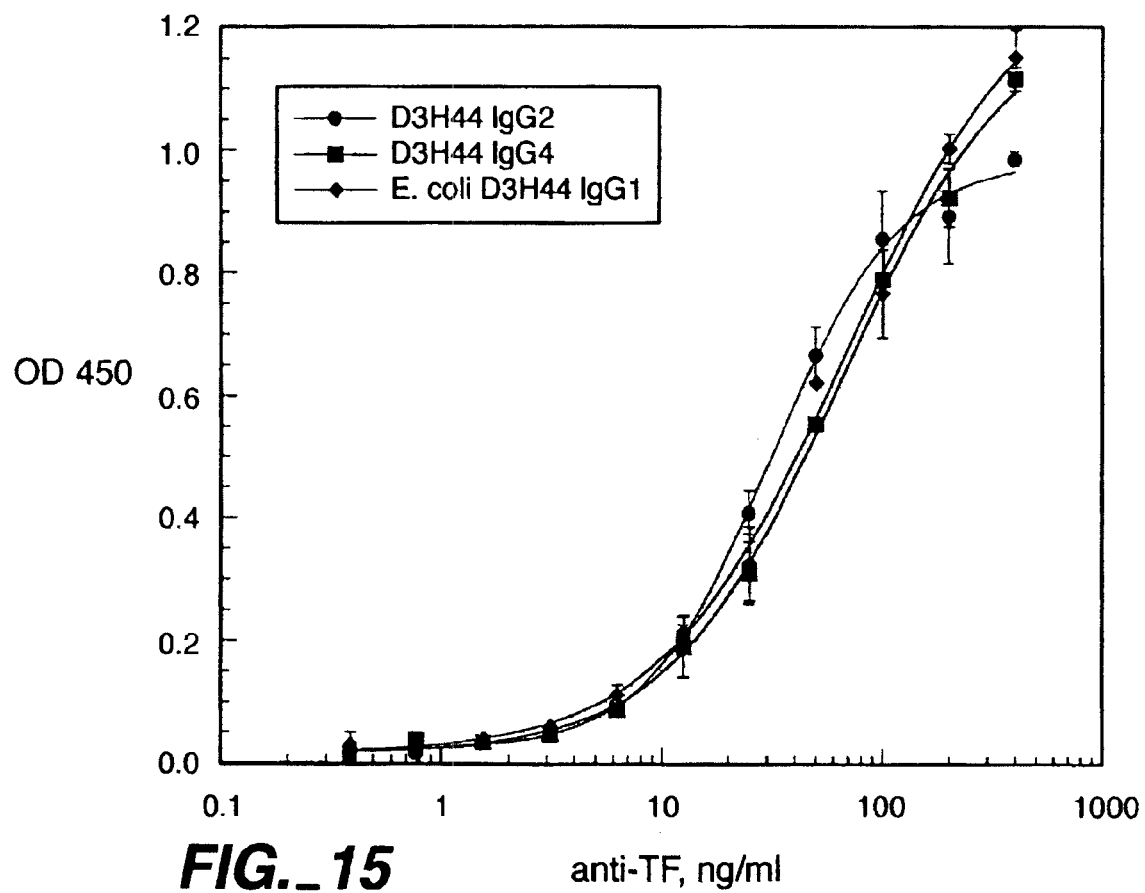
FIG._15

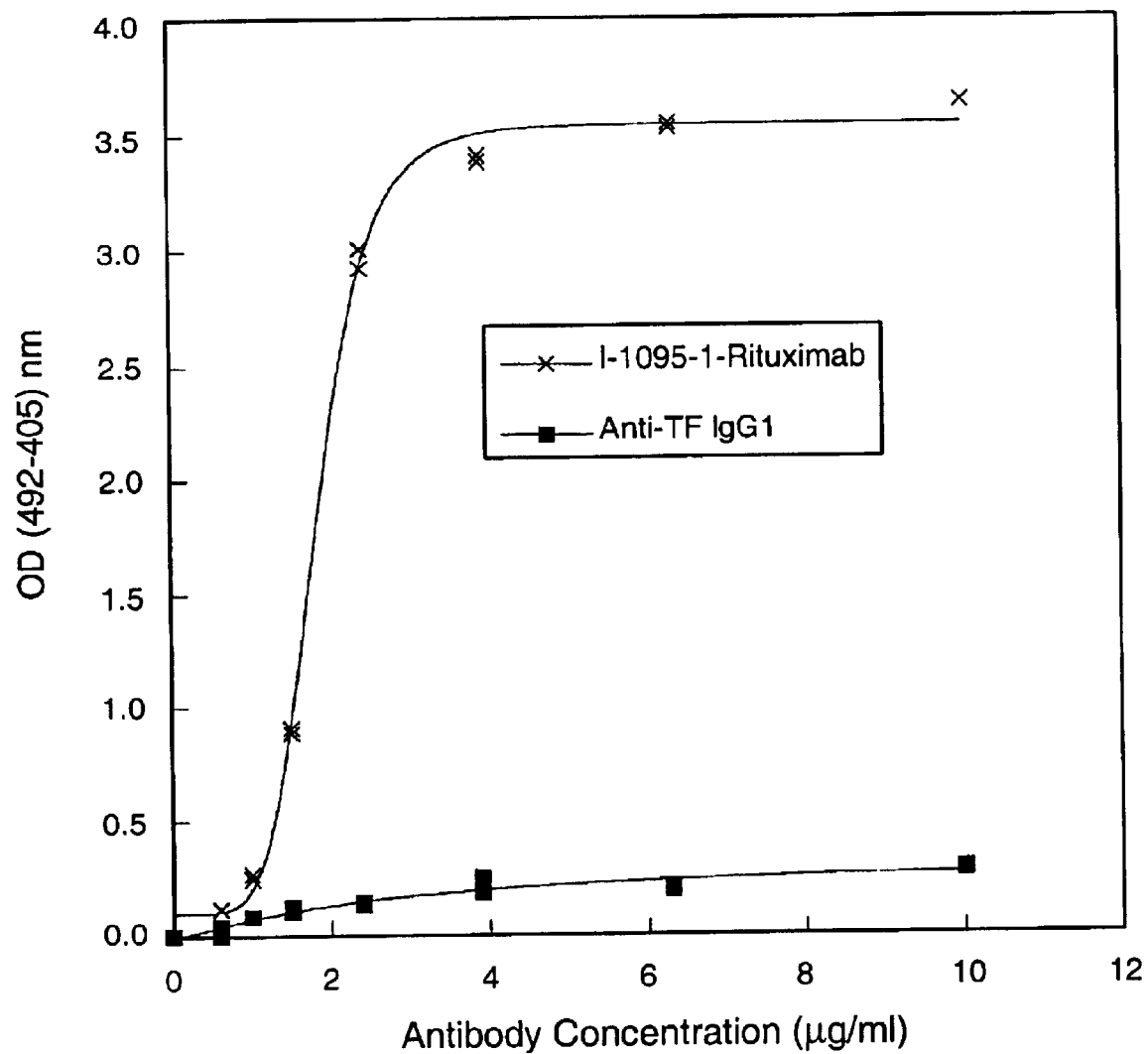
FIG._16

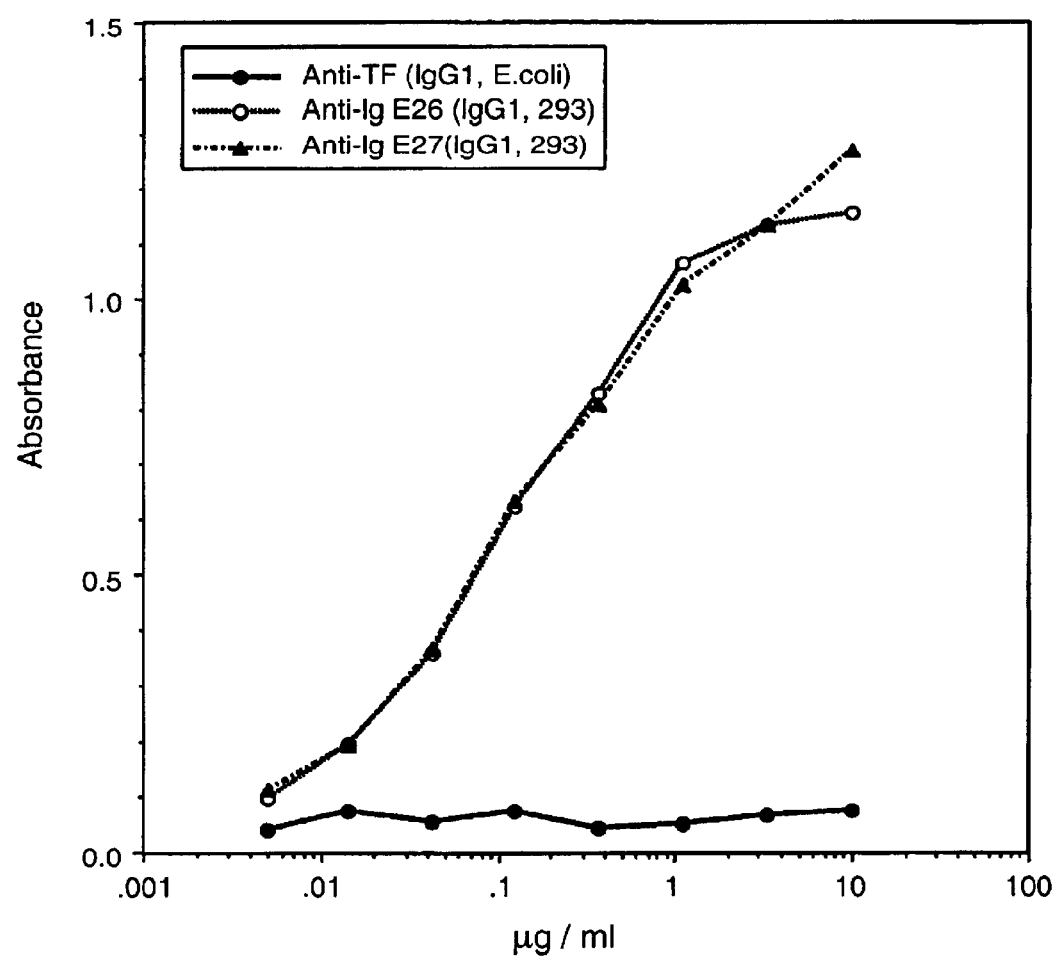
FIG._17

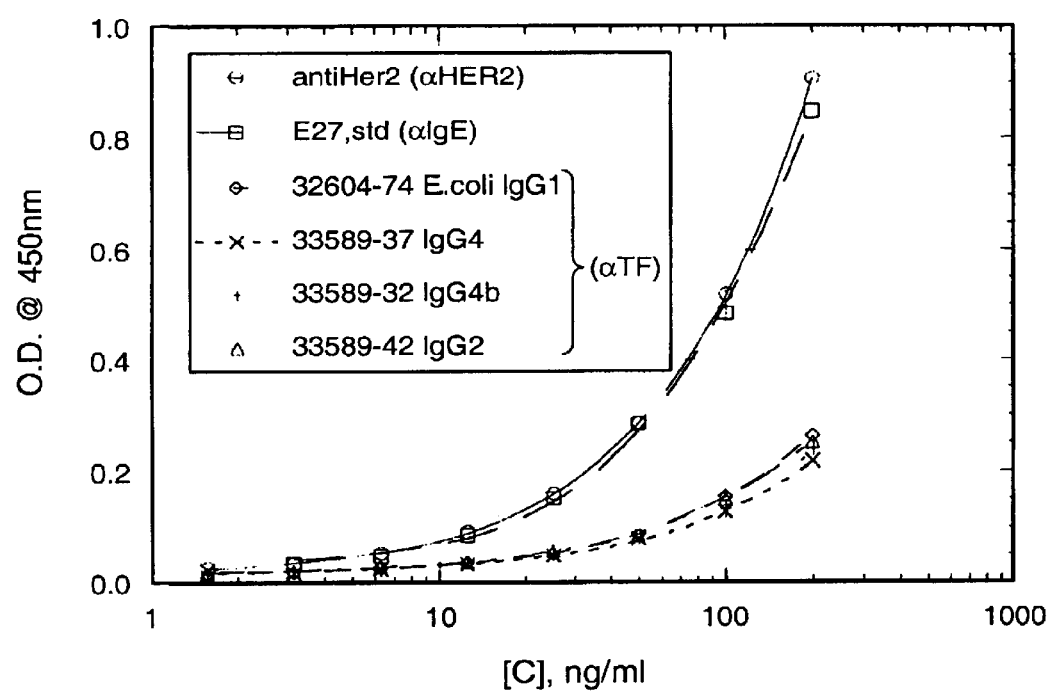
FIG._18

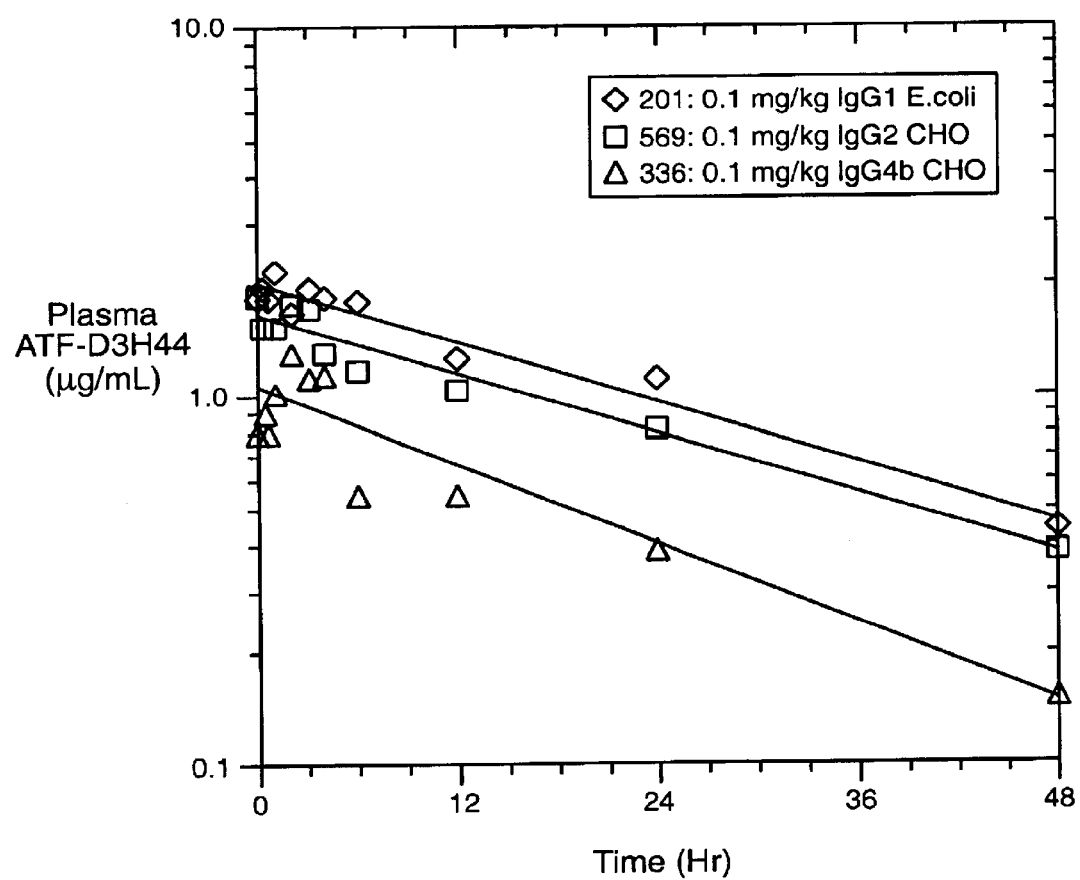
FIG._19

FIG. 20a

```
1201 CTCGGATGCC GCGGGGCGT TTTTATTGTT GCCGACGCGC ATCTCGAATG AACTGTGTGC GCAGTAGAGA GCTTTGGAGA TTATCGTCAC TTGAATTGATC
     GAGCCTACGG CGCCCCGCAA AAAATAACAA CGGCTGCGCG TAGAGCTTAC TTGACACACG CGTCCATCCT CGAAACCTCT AATAGCAGTG ACTTACGAA

1301 CGCAAATATG GCGCAAATGA CCAACAGCGG TTGATTGATC AGGTAGAGGG TCCCATCCCC GAGGCTGTAC CCGATGCCAG CATTCCTGAC GAGATACGG
     GCGTTATACC GCGTTTTACT GGTTGTCGCC AACTAACTAG TCCATCTCCC AGGGTAGGGG CTCCGACATG GGCTACGGTC GTAAGGACTG CTGCTATGCC

1401 AGCTCCTGCG CGATTACGTA AAGAAGTTAT TGAAGCATCC TGTCAGTAAA TGTCAATTAG TTTTCAACAG CTGTCATAAT CTGTCACAGG CCGAGACTTA
     TCGAGGAGCG GCTAATGCAT TTCTTCAATA ACTTCGTAGG ACAGTCATT AACAGTTATC AAAAGTTGTC GACAGTATTT GACAGTGTCC GGCTCTGAAT

1501 TAGTGCCTTT GTTTTATTT TTTAATGTAT TGTAACTAAC AACAATTGTC CACGTAAAAA GGGTATCTAG AATTATGAAG AAGAATATCG CATTCTCTCT
     ATCAGCGAAA CAAAAATAAA AAATTACATA ACATTGATTG TTGTTAACAG GTGCATTTTT CCCATAGATC TTAATACTTC TTCTTATAGC GTAAAGAAGA
   1                                                                                 M  K  K  N  I  A  F  L  L
                                                                                    ^STII Signal Sequence TIR-1

1601 TGCATCCATG ACGTAGATAC AAGCAAAAAA GATAACGATG TTTTCGCATG GCCTGAGTTC AGCTGGTGGA GTCTGGCGGT GGCCTGGTGC AGCCAGGGGG CTCACTCCGT
     ACGTAGGTAC TGCATCTATG TTCGTTTTTT CTATTGCTAC AAAAGCGTAC CGGACTCAAG TCGACCACCT CAGAGCCGCA CCGGACCACG TCGGTCCCCC GAGTGAGGCA
   10  A  S  M     F  V  F  S  I  A  T     N  A  Y     A  E  V  Q  L  V  E  S  G  G  G  L  V  Q  P  G  G  S  L  R
                                                       ^Anti-Tissue Factor Heavy Chain 1701 TTTGTCCTGT GACTTCTGG CAGCTTCAGC GTCGAAGACC GAAGTTATAA CTTCAATAT AAGGAGTACT ACATGCACTG GGTCCGGCAG GCCCGGGAAA AGGGCCTGGA ATGGGTTGGA TTGATTGATC AACTAACTAG
     AAACAGGACA CTGAAGACC GTCGAAGTCG CAGCTTCTGG CTTCAATATT GAAGTTATAA TTCCTCATGA TGTACGTGAC CCAGGCCGTC CGGGCCCTTT TCCCGGACCT TACCCAACCT AACTAACTAG LIDP 1801 CAGAGCAAGG CAACACGAAC TATGACCGGA AGTTCCAGGA CAAGGCCACT ATAAGCGCTG ACAAATCCAA GAACACAGCA TACCTGCAGA TGAACAGCCT TAGAACAGCT ACTGTGTGGA
     GTCTCGTTCC GTTGTGCTTG ATACTGGCCT TCAAGGTCCT TCAAGGTCCA TCAGGGCTTC TGTTTAAGTT CTTGTGTGGT ATGGACGTCT ACTTGTCGGA TGATCACACCT
   77  E  Q  G     N  T  I     Y  D  P  K     F  Q  D     R  A  T  I  S  A  D  N  S  K  N  T  A  Y  L  Q  M  N  S  L 1901 CGGTGCTGAG GACACTGCCG TCTATTATTG TGCTCGAGAC ACTGCTGCTTACTTGACTA ACTTCGACTA TGCTTCGATG ACGAGCTCTG TGAAGCTGAT CCTTGGGAAC CTTGGGAACC AGTGGCAGGC CCTGGGGAGG
     GCCACGACTC CTGTGACGGC AGATAATAAC ACGAGCTCTG TGACGACGAA TGAACGTGAT TGATGCTGAT TGTGACCTAC TGAAGCTGAT ACGAAGCTCT GGAACCCTTG GTCACCGTCC GGACCCCTCC
   110  R  A  E     D  T  A  V  V  Y  Y  C     A  R  D     T  A  A  Y     F  D  Y  W  G  Q     G  T  L  V  T  V  S  S  A  S 2001 ACCAAGGGCC CATCCGTCTT CCCCCTGGCA GCACCACCTCT CTGTGGAGGT GGGGCCCACA GAGACCACTIC TCTGTCCTGT GCTGCCTGGT CAAGGACTAC TTCCCCGAAC TTCCCTGATG AAGGGCTTG
     TGGTTCCCGG GTAGGCAGAA GGGGGACCGT CGTGGTGGGA GACACCTCCA CCCCGGGTGT CTCTGGTGAG GACACGGACA CGACCGGACCA GTTCCTGATG AAGGGGACTTG
   143  T  K  G  P     S  V  F     P  L  A     P  S  S  K     S  T  S     G  G  T     A  A  L  G     C  L  V  K  D  Y     F  P  E  P 2101 CGGTGACGGT GTGTGGAAC TCAGGCGCC CTGACCAGCG GCGTGCACAC CTTCCCGGCT GTCCTACAGT CCTCAGGACT CTACTCCCTC AGCAGCGTGG TGACCGTGCC CTCCAGCAGC TTGGGCACCC AGACCTACAT
     GCCACTGCCA CAGCACCTTG AGTCCGCGGG GACTGGTCGC CGCACGTGTG GAAGGGCCGA CAGGATGTCA GGAGTCCTGA GATGAGGGAG TCGTCGCACC ACTGGCACGG GAGGTCGTCG AACCCGTGGG
   177  V  T  V     S  W  N     S  G  A  L  T  S  G     V  H  T     F  P  A  V  L  Q  S     S  G  L  Y  S  L  S  S  V  V 2201 GACTGTGCCC TCTAGCAGCT TGGGCACCCA ACCGTGGACA GACTTCATC CTGGAATGTG CAACAACACC CAGCAACACC AGCAACACAC CAGAAGTTGA AGAAAGTTGA GCCAAAATCT
     CTGACACGGG AGATCGTCGA ACCCGTGGGT TGGCACCTGT CTGAAGTAG ACCCTTACAC GTTGTTGTGG GTCGTTGTGG TCGTTGTGTG GTCTTCAACT TCTTTCAACT CGGTTTTAGA
   210  T  V  P     S  S  S  L  G     T  Q     T  Y  I     C  N  V  N     H  K  P  S  N  T     K  V  D  K  K  V  E  P  K  S
```

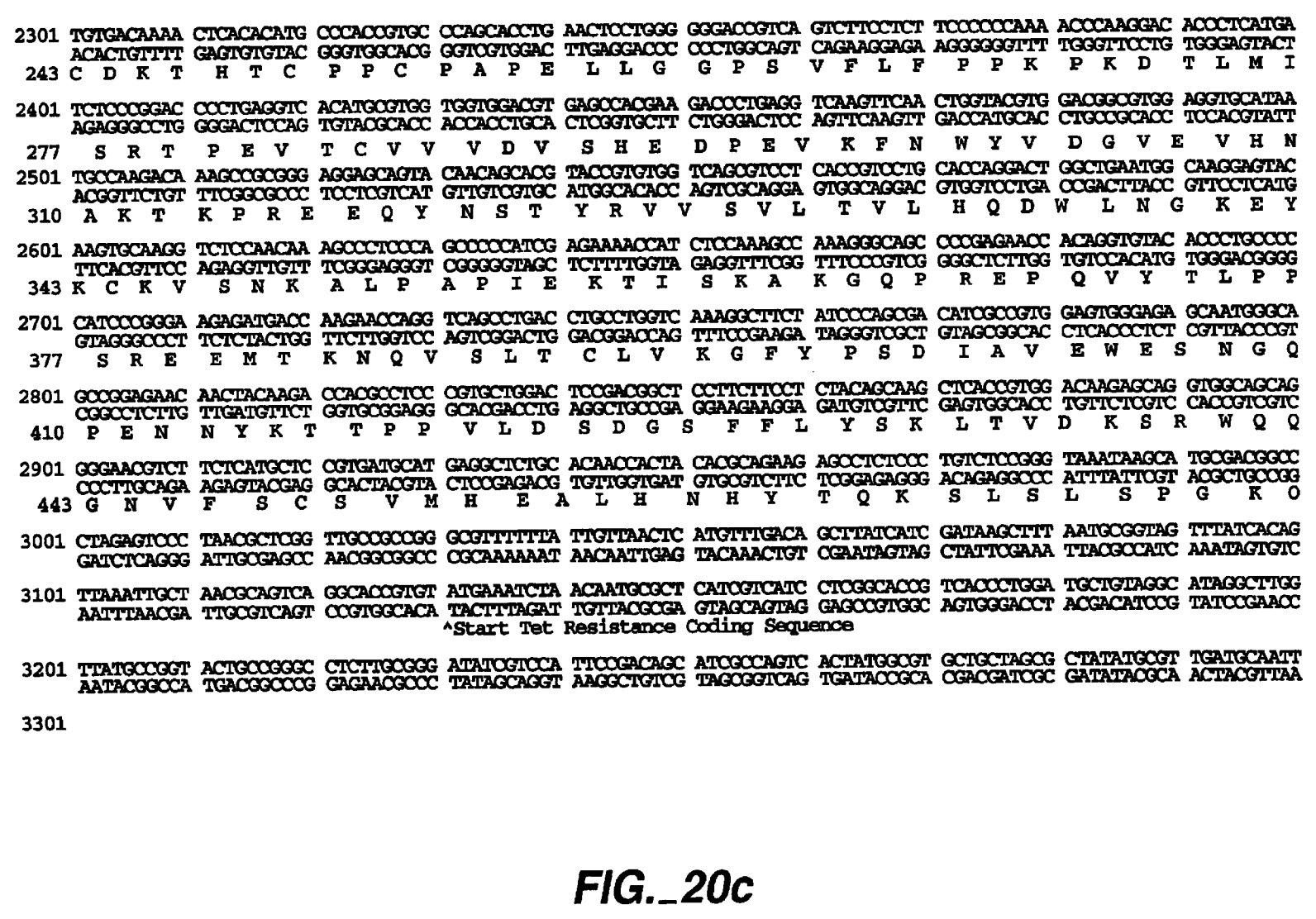

```
   1 GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGTATGA AACCTATTCC TTTATGTCTG TACTTTTTAG AGTAACGACT TCAACGAATAAA TTCGAACGGG TTTTTCTTCT TCTCAGCTTA
 101 GAACTGTGTG CGCAGGTAGA AGCTTTGGAG ATTATCGTCA CTGCAATGCT TCGCAATATG TCGCAAAATG GCGCAAAATG CCGCAAAATG GTTGATTGAT CAGGTAGAGG
     CTTGACACAC GCGTCCATCT TCGAAACCTC TAATAGCAGT GACGTTACGA AGCGTTATAC CGCGTTTAC TGGTTGTCGC CAACTAACTA GTCCATCTCC
 201 GGGCGCTGTA CGAGGTAAGC CCCGATGCCA GCATTCCTGA CAGGATATGC GAGCTGCTGC GCGATTACGT CGCTAAATGC TTTCTTCAAT AACTTCGTAG CTCGTCAGTA
     CCCGCGACAT GCTCCATTTC GGGCTACGGT CGTAAGGACT GTCCTATGCC CTCGACGACG CGCTAATGCA TTTCTTAATGTA TTGAAGCATC GAGCAGTCAT
 301 AAAAGTTAAT CTTTTCAACA GCTGTCACG CCGAGAGCTT ATAGTCGCTT GCCCAGAGACT TGTTTTATT TTTTAATGTA TTGTAACTA GTACGCAAGT
     TTTTCAATTA GAAAAGTTGT CGACAGTATT TCAACAGTGC CGGCTCTGAA TATCAGCGAA ACAAAAATAA AAAATTACAT CAGCGTTCA
 401 TCACGTAAAA AGGGTATCTA GAATTATGAA GCATTTCTTC TTGCATCTAT TTGCATCTAT GTTCGTTTT CAAACGCGTA CGCTGATATC
     AGTGCATTTT TCCCATAGAT CTTAATACTT CGTAAAGAAG AACGTAGATA CAAGCAAAA AGATAACGAT GTTGCCCAT GCGACTATAG
   1                            M  K  K  N  I     A  F  L  L     A  S  M  F  V  F     S  I  A  T     N  A  Y     A  D  I
                                *STII Signal TIR -1                                                     Anti-VEGF Light chain^
 501 CAGTTGACCC AGTCCCCGAG CCTCCTGTCC GCCTCTGTGG GCGATAGGGT CACCATCACC TGCAGCGCAA GTCAGGATAT TAGCAACTAT TTAAACTGGT
     GTCAACTGGG TCAGGGGCTC GGAGGACAGG CGGAGACACC CGCTATCCCA GTGGTAGTGG ACGTCGCGTT CAGTCGTATA ATCGTTGATA AATTTGACCA
  26 Q  L  T  Q     S  P  S     S  L  S     A  S  V  G     D  R  V     T  I  T     C  S  A  S     Q  D  I     S  N  Y     L  N  W  Y
 601 ATCAACAGAA ACCAGGTAAA GCTCCGAAAG TACTGATTTA CTTCACCTCC TCTCTCCACT CTGGAGTCCC TTCTCGCTTC TCTGGATCCG GTTCTGGGAC
     TAGTTGTCTT TGGTCCATTT CGAGGCTTTC ATGACTAAAT GAAGTGGAGG AGAGAGGTGA GACCTCAGGG AAGACGAAG AGACCTAGGC CAAGACCCTG
  60 Q  Q  K     P  G  K     A  P  K  V     L  I  Y     F  T  S     S  L  H  S     G  V  P     S  R  F     S  G  S  G     S  G  T
 701 GGATTTCACT CTGACCATCA GCAGTCTGCA GCCGAAGACT TCGCAACTTA TTACTGTCA ATTACTGTCAA TAATGACGAT GCCATCTGAT GAGCAGTTGA ACAGGTACC
     CCTAAAGTGA GACTGGTAGT CGTCAGACGT CGGCTTCTG AAGCGTTGAAT AATGACAGTT ATATATATCG CGGTAGACTA CTCGTCAACT TGTCCCATGG
  93 D  F  T     L  T  I  S     S  L  Q     P  E  D     F  A  T  Y     Y  C  Q     Q  Y  S     T  V  P  W     T  F  G     Q  G  T
 801 AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
     TTCCACCTCT AGTTTGCTTG ACACCGACGT AGTAGACAGA CCGGTAGACTA CTCGTCAACT TTAGACCTTG ACGAAGACAA CACACGGACG
 126 K  V  E  I     K  R  T     V  A  A     P  S  V  F     I  F  P     P  S  D     E  Q  L  K     S  G  T     A  S  V     V  C  L  L
 901 TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
     ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 160 N  N  F     Y  P  R     E  A  K  V     Q  W  K     V  D  N     A  L  Q  S     G  N  S     Q  E  S     V  T  E  Q     D  S  K
1001 GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
     CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
 193 D  S  T     Y  S  L  S     S  T  L     T  L  S     K  A  D  Y     E  K  H     K  V  Y     A  C  E  V     T  H  Q     G  L  S
1101 TCGCCCGTCA CAAAGAGCTT CAACAGGGGA GAGTGTTAAT AAATCCTCT ATTAGGAGA TGGCGGACG CATCGTGGCG AGCTCGGTAC CCGGGGATCT AGGCCTAACG
     AGCGGGCAGT GTTTCTCGAA GTTGTCCCCT CTCACAATTA TAAATCCTCT ATTAGGAGA TGGCCCTGC GTAGCACCGC TCGAGCCATG GGCCCCTAGA TCCGGATTGC
 226 S  P  V  T     K  S  F     N  R  G     E  C  O
```

FIG._21a

```
1201  CTCGGTTGCC GCCGGGCGTT TTTTATTGTT GCCGACGCGC ATCTCGAATG AACTGTGTGC GCAGGTAGAA GCTTTGGAGA TTATCCTCAC TGCAATGCTT
      GAGCCAACGG CGGCCCGCAA AAAATAACAA CGGCTGCGCG TAGAGCTTAC TTGACACACG CGTCCATCCT CGAAACCTCT AATAGCAGTG ACGTTACGAA
1301  CGCAATATGG CGCAACAGCGG TTGATTGATC AGTAGAGGGG GGCGCTGTAC GAGCGACATG CCGATGCCAG CCGATGCCAG CATTCCTGAC GACGATACGG
      GCGTTATACC GCGTTGTCGCC AACTAACTGA GTCATCTCCC CCGCGACATG CTCCATTCTG GGCTACGGTC GTAAGGACTG CTGCTATGCC
1401  AGTGCTGCG CGATTACGTA AAGAAGTTAT TTCTTCAATA TGAACATCC TCGTCAGTAA AAAGTTAATC TTTTCAACAG CTGTCATAAA GTTGTCACGG CCGAGACTTA
      TCGACGACGC GCTAATGCAT AAGAAGTTAT ACTTCGTAGG AGCAGTCATT TTCAATTAG AAAAGTTGTC GACAGTATTT CAACAGTGCC GGCTCTGAAT
1501  TAGTCGCTTT GTTTTATTT TTTAATGTAT TTGTAACTAG TACGCAAGTT CACGTAAAAA GGGTATCTAG AATTATGAAG AAGAATATCG CATTTCTTCT
      ATCAGCGAAA CAAAAATAAA AAATTACATA AACATTGATC ATGCGCTTCAA GTGCATTTT CCCATAGATC TTAATACTTC TTCTATAGC GTAAAGAAGA
                                                                               M  K  K  N  I  A    F  L  L
                                                                               ^STII Signal TIR-1
1601  TGCATCTATG TTCGTTTTT CTATTGCTAC AAACGCGTAC GCTGAGGTTC AGCTGGTGGA GTCTGGCGGT GGCCTGGTGC AGCCAGGGGG CTCACTCCGT
      ACGTAGATAC AAGCAAAAAA GATAACGATG TTTGCGCATG CGACTCCAAG TCGACCACCT CAGACCGCCA CCGGACCACG TCGGTCCCCC GAGTGAGGCA
      A  S  M  F  V  F  S    I  A  T  N  A  Y    A  E  V  Q  L  V  E    S  G  G    G  L  V  Q  P  G  G    S  L  R
                             ^Anti-VEGF Heavy Chain
1701  TTGTCCTGTG CAGCTTCTGG CTACGACTTC ACGCACTACG GTATGAACTG GTTCCGTCAG GCCCCGGGTA AGGGCCTGGA ATGGGTTGGA TGGATTAACA
      AACAGGACAC GTCGAAGACC GATGCTGAAG TGCGTGATGC CATACTTGAC CCAGGCAGTC CGGGGCCCAT TCCCGGACCT TACCCAACCT ACCTAATTGT
 43   L  S  C  A    A  S  G    Y  D  F    T  H  Y  G    M  N  W    V  R  Q    A  P  G  K    G  L  E    W  V  G    W  I  N  T
1801  CCTATACCGG TGAACCGACC TATGCTGCCG ATTTCAAACG TCGTTCACT TTTTCTTTAG ACGGCACGAG AAGCACAGCA TACCTGCAGA TGAACAGCCT
      GGATATGGCC ACTTGGCTGG ATACGACGGC TAAAGTTTGC AGCAAAGTGA AAAAGAAATC TGCCGTGCTC TTCGTGTCGT ATGGACGTCT ACTTGTCGGA
 77   P  Y  T  G    E  P  T    Y  A  A  D    F  K  R    R  F  T    F  S  L  D    T  S  K    S  T  A    Y  L  Q  M    N  S  L
1901  GCGCGTTGAG GACACTGCCG TCTATTACTG TGCAAAGTAC ACGTTTCATG GGTATCTGGT ACGGCACGAG CCACTGGTAT TTCGACGTCT GGGGTCAAGG AACCCTGGTC
      CGCGCAACTC CTGTGACGGC AGATAATGAC ACGTTTCATG AGCTGCAGTC CCCCAGTTCC TTGGGACCAG
 110  R  A  E    D  T  A  V    Y  Y  C    A  K  Y    P  Y  Y  Y    Y  G  T  S    H  W  Y    F  D  V  W    G  Q  G    T  L  V
2001  ACCGTCTCCT CGGCCTCCAC CAAGGGCCCA TCGGTCTTCC CCCTGGCACC CTCCTCCAAG AGCACCTCTG GGGGCACAGC GGCCCTGGGC TGCCTGGTCA ACGGACCAGT
      TGGCAGAGGA GCCGGAGGTG GTTCCCGGGT AGCCAGAAGG GGGACCGTGG GAGGAGGTTC TCGTGGAGAC CCCCGTGTCG TCGGGACCCG ACGGACCAGT
 143  T  V  S  S    A  S  T    K  G  P    S  V  F  P    L  A  P    S  S  K    S  T  S  G    G  T  A    A  L  G    C  L  V  K
2101  AGGACTACTT CCCCGAACCG GTGACGGTGT CGTGGAACTC AGGCGCCCTG ACCAGCGGCG TGCACACCTT CCCGGCTGTC CTACAGTCCT CAGGACTCTA CAGGACTCTA GTCCTGAGAT
      TCCTGATGAA GGGGCTTGGC CACTGCCACA GCACCTTGAG TCCGCGGGAC TGGTCGCCGC ACGTGTGGAA GGGCCGACAG GATGTCAGGA GTCCTGAGAT
 177  D  Y  F    P  E  P    V  T  V  S    W  N  S    G  A  L    T  S  G    V  H  T  F    P  A  V    L  Q  S  S    G  L  Y
2201  CTCCCTCAGC AGCGTGGTGA CTGTGCCCTC TAGCAGCTTG GGCACCCAGA CCTACATCTG CAACGTGAAT CACAAGCCCA GCAACACCAA GGTGGACAAG
      GAGGGAGTCG TCGCACCACT GACACGGGAG ATCGTCGAAC CCGTGGGTCT GGATGTAGAC GTTGCACTTA GTGTTCGGGT CGTTGTGGTT CCACCTGTTC
 210  S  L  S    S  V  V  T    V  P  S    S  S  L    G  T  Q  T    Y  I  C    N  V  N    H  K  P  S    N  T  K    V  D  K
```

*FIG._21b*

```
2301  AAAGTTGAGC CCAAATCTTG TGACAAAACT CACACATGCC CACCGTGCCC AGCACCTGAA CTTCCTCTTC CCCCCAAAAC
      TTTCAACTCG GGTTTAGAAC ACTGTTTTGA GTGTGTACGG GTGGCACGGG TCGTGGACTT GAAGGAGAAG GGGGGTTTTG
243    K  V  E  P    K  S  C    D  K  T    H  T  C  P    P  C  P    A  P  E    L  L  G    P  P  K  P

2401  CCAAGGACAC CCTCATGATC TCCCGGACCC CTGAGGTCAC ATGCGTGGTG GTGGACGTGA GCCACGAAGA CCCTGAGGTC AAGTTCAACT GGTACGTGGA
      GGTTCCTGTG GGAGTACTAG AGGGCCTGGG GACTCCAGTG TACGCACCAC CACCTGCACT CGGTGCTTCT GGGACTCCAG TTCAAGTTGA CCATGCACCT
277    K  D  T    L  M  I    S  R  T  P    E  V  T    C  V  V    V  D  V  S    H  E  D    P  E  V    K  F  N  W    Y  V  D

2501  CGGCGTGGAG GTGCATAATG CCAAGACAAA GCCGCGGGAG GAGCAGTACA ACAGCACGTA CCGTGTGGTC AGCGTCCTCA CCGTCCTGCA CCAGGACTGG
      GCCGCACCTC CACGTATTAC GGTTCTGTTT CGGCGCCCTC CTCGTCATGT TGTCGTGCAT GGCACACCAG TCGCAGGAGT GGCAGGACGT GGTCCTGACC
310    G  V  E    V  H  N  A    K  T  K    P  R  E    E  Q  Y  N    S  T  Y    R  V  V    S  V  L  T    V  L  H    Q  D  W

2601  CTGAATGGCA AGGAGTACAA GTGCAAGGTC TCCAACAAAG CCCTCCCAGC CCCCATCGAG AAAACCATCT CCAAAGCCAA AGGGCAGCCC CGAGAACCAC
      GACTTACCGT TCCTCATGTT CACGTTCCAG AGGTTGTTTC GGGAGGGTCG GGGGTAGCTC TTTTGGTAGA GGTTTCGGTT TCCCGTCGGG GCTCTTGGTG
343    L  N  G  K    E  Y  K    C  K  V    S  N  K  A    L  P  A    P  I  E    K  T  I  S    K  A  K    G  Q  P    R  E  P  Q

2701  AGGTGTACAC CCTGCCCCCA TCCCGGGAAG AGATGACCAA GAACCAGGTC AGCCTGACCT GCCTGGTCAA AGGCTTCTAT CCCAGCGACA TCGCCGTGGA
      TCCACATGTG GGACGGGGGT AGGGCCCTTC TCTACTGGTT CTTGGTCCAG TCGGACTGGA CGGACCAGTT TCCGAAGATA GGGTCGCTGT AGCGGCACCT
377    V  Y  T    L  P  P    S  R  E  E    M  T  K    N  Q  V    S  L  T  C    L  V  K    G  F  Y    P  S  D  I    A  V  E

2801  GTGGGAGAGC AATGGGCAGC CGGAGAACAA CTACAAGACC ACGCCTCCCG TGCTGGACTC CGACGGCTCC TTCTTCCTCT ACAGCAAGCT CACCGTGGAC
      CACCCTCTCG TTACCCGTCG GCCTCTTGTT GATGTTCTGG TGCGGAGGGC ACGACCTGAG GCTGCCGAGG AAGAAGGAGA TGTCGTTCGA GTGGCACCTG
410    W  E  S    N  G  Q  P    E  N  N    Y  K  T    T  P  P  V    L  D  S    D  G  S    F  F  L  Y    S  K  L    T  V  D

2901  AAGAGCAGGT GGCAGCAGGG GAACGTCTTC TCATGCTCCG TGATGCATGA GGCTCTGCAC AACCACTACA CGCAGAAGAG CCTCTCCCTG TCTCCGGGTA
      TTCTCGTCCA CCGTCGTCCC CTTGCAGAAG AGTACGAGGC ACTACGTACT CCGAGACGTG TTGGTGATGT GCGTCTTCTC GGAGAGGGAC AGAGGCCCAT
443    K  S  R  W    Q  Q  G    N  V  F    S  C  S  V    M  H  E    A  L  H    N  H  Y  T    Q  K  S    L  S  L    S  P  G  K

3001  AATAAGCATG CGACGGCCCT AGAGTCCCTA ACGCTCGGTT GCCGCCGGGC GTTTTTTATT CAATTGAGTA GTTAACTCAT CAAACTGTCG TAAGCTTTAA ATTCGAAATT
      TTATTCGTAC GCTGCCGGGA TCTCAGGGAT TGCGAGCCAA CGGCGGCCCG CAAAAAATAA GTTAACTCAT CAATTGAGTA GTTTGACAGC ATTCGAAATT TAAGCTTTAA
477    O
                                                                            ^Start Tet Resistance Coding Sequence 3101  TGCGGTAGTT TATCACAGTT AAATTGCTAA CACCGTGCAG CACCGTGTAT GAAATCTAAC AATGCGCTCA TCGTCATCCT CGGCACCGTC ACCCTGGATG
      ACGCCATCAA ATAGTGTCAA TTTAACGATT GTGGCACGTC GTGGCACATA CTTTAGATTG TTACGCGAGT AGCAGTAGGA GCCGTGGCAG TGGGACCTAC 3201  CTGTAGGCAT AGGCTTGGTT ATGCCGGTAC TGCCGGGCCT CTTGCGGGAT ATCGTCCATT CCGACAGCAT CGCCAGTCAC TATGGCGTGC TGCTAGCGCT
      GACATCCGTA TCCGAACCAA TACGGCCATG ACGGCCCGGA GAACGCCCTA TAGCAGGTAA GGCTGTCGTA CGGTCAGTG  GCGGTCAGTG ATACCGCACG ACGATCGCGA
3301
```

FIG._21c

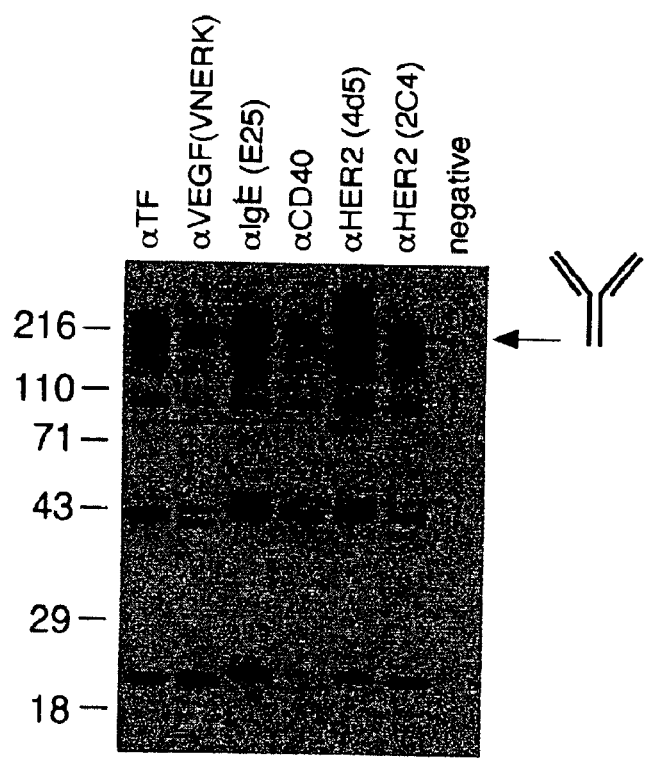
FIG._22A
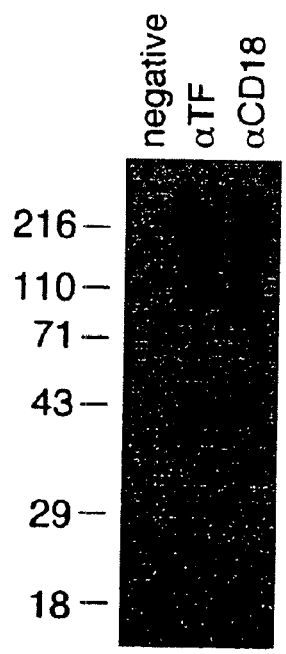
FIG._22B

SEQUENCE LISTING

<160> NUMBER OF SEQ ID NOS: 11

<210> SEQ ID NO 1
<211> LENGTH: 3300
<212> TYPE: DNA
<213> ORGANISM: Artificial sequence
<220> FEATURE:
<223> OTHER INFORMATION: anti-TF vector

<400> SEQUENCE: 1

```
gaattcaact tctccatact ttggataagg aaatacagac atgaaaaatc          50
tcattgctga gttgttattt aagcttgccc aaaaagaaga agagtcgaat         100
gaactgtgtg cgcaggtaga agctttggag attatcgtca ctgcaatgct         150
tcgcaatatg gcgcaaaatg accaacagcg gttgattgat caggtagagg         200
gggcgctgta cgaggtaaag cccgatgcca gcattcctga cgacgatacg         250
gagctgctgc gcgattacgt aaagaagtta ttgaagcatc ctcgtcagta         300
aaaagttaat cttttcaaca gctgtcataa agttgtcacg gccgagactt         350
atagtcgctt tgttttattt ttttaatgta tttgtaacta gtacgcaagt         400
tcacgtaaaa agggtatcta gaattatgaa gaagaatatc gcatttcttc         450
ttgcatctat gttcgttttt tctattgcta caaacgcgta cgctgatatc         500
cagatgaccc agtccccgag ctccctgtcc gcctctgtgg gcgatagggt         550
caccatcacc tgcagagcca gtcgcgacat caagagctat ctgaactggt         600
atcaacagaa accaggaaaa gctccgaaag tactgattta ctatgctact         650
agtctcgctg aaggagtccc ttctcgcttc tctggatccg gttctgggac         700
ggattacact ctgaccatca gcagtctgca gccagaagac ttcgcaactt         750
attactgtct tcagcacgga gagtctccat ggacatttgg acagggtacc         800
aaggtggaga tcaaacgaac tgtggctgca ccatctgtct tcatcttccc         850
gccatctgat gagcagttga aatctggaac tgcttctgtt gtgtgcctgc         900
tgaataactt ctatcccaga gaggccaaag tacagtggaa ggtggataac         950
gccctccaat cgggtaactc ccaggagagt gtcacagagc aggacagcaa        1000
ggacagcacc tacagcctca gcagcaccct gacgctgagc aaagcagact        1050
acgagaaaca caaagtctac gcctgcgaag tcacccatca gggcctgagc        1100
tcgcccgtca caaagagctt caacagggga gagtgttaat taaatcctct        1150
acgccggacg catcgtggcg agctcggtac ccggggatct aggcctaacg        1200
ctcggttgcc gccgggcgtt ttttattgtt gccgacgcgc atctcgaatg        1250
aactgtgtgc gcaggtagaa gctttggaga ttatcgtcac tgcaatgctt        1300
cgcaatatgg cgcaaaatga ccaacagcgg ttgattgatc aggtagaggg        1350
ggcgctgtac gaggtaaagc ccgatgccag cattcctgac gacgatacgg        1400
agctgctgcg cgattacgta aagaagttat gaagcatcc tcgtcagtaa        1450
aaagttaatc tttcaacag ctgtcataaa gttgtcacgg ccgagactta        1500
tagtcgcttt gttttatt tttaatgtat ttgtaactag tacgcaagtt        1550
cacgtaaaaa gggtatctag aattatgaag aagaatatcg catttcttct        1600
tgcatctatg ttcgtttttt ctattgctac aaacgcgtac gctgaggttc        1650
```

-continued

```
agctggtgga gtctggcggt ggcctggtgc agccaggggg ctcactccgt        1700
ttgtcctgtg cagcttctgg cttcaatatt aaggagtact acatgcactg        1750
ggtccgtcag gccccgggta agggcctgga atgggttgga ttgattgatc        1800
cagagcaagg caacacgatc tatgacccga agttccagga ccgtgccact        1850
ataagcgctg acaattccaa aaacacagca tacctgcaga tgaacagcct        1900
gcgtgctgag gacactgccg tctattattg tgctcgagac acggccgctt        1950
acttcgacta ctggggtcaa ggaaccctgg tcaccgtctc ctcggcctcc        2000
accaagggcc catcggtctt ccccctggca ccctcctcca agagcacctc        2050
tgggggcaca gcggccctgg gctgcctggt caaggactac ttccccgaac        2100
cggtgacggt gtcgtggaac tcaggcgccc tgaccagcgg cgtgcacacc        2150
ttcccggctg tcctacagtc ctcaggactc tactccctca gcagcgtggt        2200
gactgtgccc tctagcagct tgggcaccca gacctacatc tgcaacgtga        2250
atcacaagcc cagcaacacc aaggtggaca agaaagttga gcccaaatct        2300
tgtgacaaaa ctcacacatg cccaccgtgc ccagcacctg aactcctggg        2350
gggaccgtca gtcttcctct tccccccaaa acccaaggac accctcatga        2400
tctcccggac ccctgaggtc acatgcgtgg tggtggacgt gagccacgaa        2450
gaccctgagg tcaagttcaa ctggtacgtg gacggcgtgg aggtgcataa        2500
tgccaagaca aagccgcggg aggagcagta caacagcacg taccgtgtgg        2550
tcagcgtcct caccgtcctg caccaggact ggctgaatgg caaggagtac        2600
aagtgcaagg tctccaacaa agccctccca gcccccatcg agaaaaccat        2650
ctccaaagcc aaagggcagc ccgagaacc acaggtgtac accctgcccc        2700
catcccggga gagatgacc aagaaccagg tcagcctgac ctgcctggtc        2750
aaaggcttct atcccagcga catcgccgtg gagtgggaga gcaatgggca        2800
gccggagaac aactacaaga ccacgcctcc cgtgctggac tccgacggct        2850
ccttcttcct ctacagcaag ctcaccgtgg acaagagcag gtggcagcag        2900
gggaacgtct tctcatgctc cgtgatgcat gaggctctgc acaaccacta        2950
cacgcagaag agcctctccc tgtctccggg taaatagca tgcgacggcc        3000
ctagagtccc taacgctcgg ttgccgccgg gcgttttta ttgttaactc        3050
atgtttgaca gcttatcatc gataagcttt aatgcggtag tttatcacag        3100
ttaaattgct aacgcagtca ggcaccgtgt atgaaatcta acaatgcgct        3150
catcgtcatc ctcggcaccg tcaccctgga tgctgtaggc ataggcttgg        3200
ttatgccggt actgccgggc ctcttgcggg atatcgtcca ttccgacagc        3250
atcgccagtc actatggcgt gctgctagcg ctatatgcgt tgatgcaatt        3300
```

<210> SEQ ID NO 2
<211> LENGTH: 3300
<212> TYPE: DNA
<213> ORGANISM: Artificial sequence
<220> FEATURE:
<223> OTHER INFORMATION: anti-VEGF vector

<400> SEQUENCE: 2

```
gaattcaact tctccatact ttggataagg aaatacagac atgaaaaatc          50
```

| | |
|---|---|
| tcattgctga gttgttattt aagcttgccc aaaaagaaga agagtcgaat | 100 |
| gaactgtgtg cgcaggtaga agctttggag attatcgtca ctgcaatgct | 150 |
| tcgcaatatg gcgcaaaatg accaacagcg gttgattgat caggtagagg | 200 |
| gggcgctgta cgaggtaaag cccgatgcca gcattcctga cgacgatacg | 250 |
| gagctgctgc gcgattacgt aaagaagtta ttgaagcatc ctcgtcagta | 300 |
| aaaagttaat cttttcaaca gctgtcataa agttgtcacg gccgagactt | 350 |
| atagtcgctt tgttttattt ttttaatgta tttgtaacta gtacgcaagt | 400 |
| tcacgtaaaa agggtatcta gaattatgaa gaagaatatc gcatttcttc | 450 |
| ttgcatctat gttcgttttt tctattgcta caaacgcgta cgctgatatc | 500 |
| cagttgaccc agtccccgag ctccctgtcc gcctctgtgg gcgataggt | 550 |
| caccatcacc tgcagcgcaa gtcaggatat tagcaactat ttaaactggt | 600 |
| atcaacagaa accaggaaaa gctccgaaag tactgattta cttcacctcc | 650 |
| tctctccact ctggagtccc ttctcgcttc tctggatccg gttctgggac | 700 |
| ggatttcact ctgaccatca gcagtctgca gccagaagac ttcgcaactt | 750 |
| attactgtca acagtatagc accgtgccgt ggacgtttgg acagggtacc | 800 |
| aaggtggaga tcaaacgaac tgtggctgca ccatctgtct tcatcttccc | 850 |
| gccatctgat gagcagttga aatctggaac tgcttctgtt gtgtgcctgc | 900 |
| tgaataactt ctatcccaga gaggccaaag tacagtggaa ggtggataac | 950 |
| gccctccaat cgggtaactc ccaggagagt gtcacagagc aggacagcaa | 1000 |
| ggacagcacc tacagcctca gcagcaccct gacgctgagc aaagcagact | 1050 |
| acgagaaaca caaagtctac gcctgcgaag tcacccatca gggcctgagc | 1100 |
| tcgcccgtca caaagagctt caacagggga gagtgttaat aaatcctct | 1150 |
| acgccggacg catcgtggcg agctcggtac ccggggatct aggcctaacg | 1200 |
| ctcggttgcc gccgggcgtt ttttattgtt gccgacgcgc atctcgaatg | 1250 |
| aactgtgtgc gcaggtagaa gctttggaga ttatcgtcac tgcaatgctt | 1300 |
| cgcaatatgg cgcaaaatga ccaacagcgg ttgattgatc aggtagaggg | 1350 |
| ggcgctgtac gaggtaaagc ccgatgccag cattcctgac gacgatacgg | 1400 |
| agctgctgcg cgattacgta aagaagttat tgaagcatcc tcgtcagtaa | 1450 |
| aaagttaatc ttttcaacag ctgtcataaa gttgtcacgg ccgagactta | 1500 |
| tagtcgcttt gttttatttt ttaatgtat tgtaactag tacgcaagtt | 1550 |
| cacgtaaaaa gggtatctag aattatgaag aagaatatcg catttcttct | 1600 |
| tgcatctatg ttcgtttttt ctattgctac aaacgcgtac gctgaggttc | 1650 |
| agctggtgga gtctggcggt ggcctggtgc agccaggggg ctcactccgt | 1700 |
| ttgtcctgtg cagcttctgg ctacgacttc acgcactacg gtatgaactg | 1750 |
| ggtccgtcag gccccgggta agggcctgga atgggttgga tggattaaca | 1800 |
| cctataccgg tgaaccgacc tatgctgcgg atttcaaacg tcgtttcact | 1850 |
| ttttctttag acacctccaa aagcacagca tacctgcaga tgaacagcct | 1900 |
| gcgcgctgag gacactgccg tctattactg tgcaaagtac ccgtactatt | 1950 |
| acggcacgag ccactggtat ttcgacgtct ggggtcaagg aaccctggtc | 2000 |
| accgtctcct cggcctccac caagggccca tcggtcttcc ccctggcacc | 2050 |

```
ctcctccaag agcacctctg ggggcacagc ggccctgggc tgcctggtca          2100
aggactactt ccccgaaccg gtgacggtgt cgtggaactc aggcgccctg          2150
accagcggcg tgcacacctt cccggctgtc ctacagtcct caggactcta          2200
ctccctcagc agcgtggtga ctgtgccctc tagcagcttg ggcacccaga          2250
cctacatctg caacgtgaat cacaagccca gcaacaccaa ggtggacaag          2300
aaagttgagc ccaaatcttg tgacaaaact cacacatgcc caccgtgccc          2350
agcacctgaa ctcctggggg gaccgtcagt cttcctcttc cccccaaaac          2400
ccaaggacac cctcatgatc tcccggaccc ctgaggtcac atgcgtggtg          2450
gtggacgtga gccacgaaga ccctgaggtc aagttcaact ggtacgtgga          2500
cggcgtggag gtgcataatg ccaagacaaa gccgcgggag gagcagtaca          2550
acagcacgta ccgtgtggtc agcgtcctca ccgtcctgca ccaggactgg          2600
ctgaatggca aggagtacaa gtgcaaggtc tccaacaaag ccctcccagc          2650
ccccatcgag aaaaccatct ccaaagccaa agggcagccc cgagaaccac          2700
aggtgtacac cctgccccca tcccgggaag agatgaccaa gaaccaggtc          2750
agcctgacct gcctggtcaa aggcttctat cccagcgaca tcgccgtgga          2800
gtgggagagc aatgggcagc cggagaacaa ctacaagacc acgcctcccg          2850
tgctggactc cgacggctcc ttcttcctct acagcaagct caccgtggac          2900
aagagcaggt ggcagcaggg gaacgtcttc tcatgctccg tgatgcatga          2950
ggctctgcac aaccactaca cgcagaagag cctctccctg tctccgggta          3000
aataagcatg cgacggccct agagtcccta acgctcggtt gccgccgggc          3050 gtttttatt gttaactcat gtttgacagc ttatcatcga taagctttaa          3100
tgcggtagtt tatcacagtt aaattgctaa cgcagtcagg caccgtgtat          3150
gaaatctaac aatgcgctca tcgtcatcct cggcaccgtc accctggatg          3200
ctgtaggcat aggcttggtt atgccggtac tgccgggcct cttgcgggat          3250
atcgtccatt ccgacagcat cgccagtcac tatggcgtgc tgctagcgct          3300
```

<210> SEQ ID NO 3
<211> LENGTH: 35
<212> TYPE: DNA
<213> ORGANISM: Artificial sequence
<220> FEATURE:
<223> OTHER INFORMATION: probe

<400> SEQUENCE: 3
catactggta ccaggatcta gagggaagat ttatg          35

<210> SEQ ID NO 4
<211> LENGTH: 28
<212> TYPE: DNA
<213> ORGANISM: Artificial sequence
<220> FEATURE:
<223> OTHER INFORMATION: probe

<400> SEQUENCE: 4
ctggtgagta ctcaaccaag tcattctg          28

<210> SEQ ID NO 5
<211> LENGTH: 33
<212> TYPE: DNA

```
<213> ORGANISM: Artificial sequence
<220> FEATURE:
<223> OTHER INFORMATION: probe

<400> SEQUENCE: 5
tgcacggtta acatgctgtg gtgtcatggt cgg                                33

<210> SEQ ID NO 6
<211> LENGTH: 27
<212> TYPE: DNA
<213> ORGANISM: Artificial sequence
<220> FEATURE:
<223> OTHER INFORMATION: probe

<400> SEQUENCE: 6
tttaccgtta acaaacatcg ccggaac                                      27

<210> SEQ ID NO 7
<211> LENGTH: 34
<212> TYPE: DNA
<213> ORGANISM: Artificial sequence
<220> FEATURE:
<223> OTHER INFORMATION: probe

<400> SEQUENCE: 7
tcagctgccg gcgtccgatg cgaattattt accg                              34

<210> SEQ ID NO 8
<211> LENGTH: 237
<212> TYPE: PRT
<213> ORGANISM: Artificial sequence
<220> FEATURE:
<223> OTHER INFORMATION: anti-TF light chain

<400> SEQUENCE: 8
```

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
            20                  25                  30

Pro Ser Ser Leu Ser Ala Ser Val Gly Asp Arg Val Thr Ile Thr
            35                  40                  45

Cys Arg Ala Ser Arg Asp Ile Lys Ser Tyr Leu Asn Trp Tyr Gln
            50                  55                  60

Gln Lys Pro Gly Lys Ala Pro Lys Val Leu Ile Tyr Tyr Ala Thr
            65                  70                  75

Ser Leu Ala Glu Gly Val Pro Ser Arg Phe Ser Gly Ser Gly Ser
            80                  85                  90

Gly Thr Asp Tyr Thr Leu Thr Ile Ser Ser Leu Gln Pro Glu Asp
            95                 100                 105

Phe Ala Thr Tyr Tyr Cys Leu Gln His Gly Glu Ser Pro Trp Thr
           110                 115                 120

Phe Gly Gln Gly Thr Lys Val Glu Ile Lys Arg Thr Val Ala Ala
           125                 130                 135

Pro Ser Val Phe Ile Phe Pro Pro Ser Asp Glu Gln Leu Lys Ser
           140                 145                 150

Gly Thr Ala Ser Val Val Cys Leu Leu Asn Asn Phe Tyr Pro Arg
           155                 160                 165

Glu Ala Lys Val Gln Trp Lys Val Asp Asn Ala Leu Gln Ser Gly
           170                 175                 180

Asn Ser Gln Glu Ser Val Thr Glu Gln Asp Ser Lys Asp Ser Thr

```
                185                 190                 195
Tyr Ser Leu Ser Ser Thr Leu Thr Leu Ser Lys Ala Asp Tyr Glu
                200                 205                 210

Lys His Lys Val Tyr Ala Cys Glu Val Thr His Gln Gly Leu Ser
                215                 220                 225

Ser Pro Val Thr Lys Ser Phe Asn Arg Gly Glu Cys
                230                 235

<210> SEQ ID NO 9
<211> LENGTH: 470
<212> TYPE: PRT
<213> ORGANISM: Artificial sequence
<220> FEATURE:
<223> OTHER INFORMATION: anti-TF heavy chain

<400> SEQUENCE: 9

Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Glu Ser
                 20                  25                  30

Gly Gly Gly Leu Val Gln Pro Gly Gly Ser Leu Arg Leu Ser Cys
                 35                  40                  45

Ala Ala Ser Gly Phe Asn Ile Lys Glu Tyr Tyr Met His Trp Val
                 50                  55                  60

Arg Gln Ala Pro Gly Lys Gly Leu Glu Trp Val Gly Leu Ile Asp
                 65                  70                  75

Pro Glu Gln Gly Asn Thr Ile Tyr Asp Pro Lys Phe Gln Asp Arg
                 80                  85                  90

Ala Thr Ile Ser Ala Asp Asn Ser Lys Asn Thr Ala Tyr Leu Gln
                 95                 100                 105

Met Asn Ser Leu Arg Ala Glu Asp Thr Ala Val Tyr Tyr Cys Ala
                110                 115                 120

Arg Asp Thr Ala Ala Tyr Phe Asp Tyr Trp Gly Gln Gly Thr Leu
                125                 130                 135

Val Thr Val Ser Ser Ala Ser Thr Lys Gly Pro Ser Val Phe Pro
                140                 145                 150

Leu Ala Pro Ser Ser Lys Ser Thr Ser Gly Gly Thr Ala Ala Leu
                155                 160                 165

Gly Cys Leu Val Lys Asp Tyr Phe Pro Glu Pro Val Thr Val Ser
                170                 175                 180

Trp Asn Ser Gly Ala Leu Thr Ser Gly Val His Thr Phe Pro Ala
                185                 190                 195

Val Leu Gln Ser Ser Gly Leu Tyr Ser Leu Ser Ser Val Val Thr
                200                 205                 210

Val Pro Ser Ser Ser Leu Gly Thr Gln Thr Tyr Ile Cys Asn Val
                215                 220                 225

Asn His Lys Pro Ser Asn Thr Lys Val Asp Lys Lys Val Glu Pro
                230                 235                 240

Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp
```

-continued

```
                    290                 295                 300

Tyr Val Asp Gly Val Glu Val His Asn Ala Lys Thr Lys Pro Arg
                305                 310                 315

Glu Glu Gln Tyr Asn Ser Thr Tyr Arg Val Val Ser Val Leu Thr
            320                 325                 330

Val Leu His Gln Asp Trp Leu Asn Gly Lys Glu Tyr Lys Cys Lys
            335                 340                 345

Val Ser Asn Lys Ala Leu Pro Ala Pro Ile Glu Lys Thr Ile Ser
            350                 355                 360

Lys Ala Lys Gly Gln Pro Arg Glu Pro Gln Val Tyr Thr Leu Pro
            365                 370                 375

Pro Ser Arg Glu Glu Met Thr Lys Asn Gln Val Ser Leu Thr Cys
            380                 385                 390

Leu Val Lys Gly Phe Tyr Pro Ser Asp Ile Ala Val Glu Trp Glu
            395                 400                 405

Ser Asn Gly Gln Pro Glu Asn Asn Tyr Lys Thr Thr Pro Pro Val
            410                 415                 420

Leu Asp Ser Asp Gly Ser Phe Phe Leu Tyr Ser Lys Leu Thr Val
            425                 430                 435

Asp Lys Ser Arg Trp Gln Gln Gly Asn Val Phe Ser Cys Ser Val
            440                 445                 450

Met His Glu Ala Leu His Asn His Tyr Thr Gln Lys Ser Leu Ser
            455                 460                 465

Leu Ser Pro Gly Lys
            470

<210> SEQ ID NO 10
<211> LENGTH: 237
<212> TYPE: PRT
<213> ORGANISM: Artificial sequence
<220> FEATURE:
<223> OTHER INFORMATION: anti-VEGF light chain

<400> SEQUENCE: 10

Met Lys Lys Asn Ile Ala Phe Leu Leu Ala Ser Met Phe Val Phe
  1               5                  10                  15

Ser Ile Ala Thr Asn Ala Tyr Ala Asp Ile Gln Leu Thr Gln Ser
                20                  25                  30

Pro Ser Ser Leu Ser Ala Ser Val Gly Asp Arg Val Thr Ile Thr
            35                  40                  45

Cys Ser Ala Ser Gln Asp Ile Ser Asn Tyr Leu Asn Trp Tyr Gln
            50                  55                  60

Gln Lys Pro Gly Lys Ala Pro Lys Val Leu Ile Tyr Phe Thr Ser
            65                  70                  75

Ser Leu His Ser Gly Val Pro Ser Arg Phe Ser Gly Ser Gly Ser
            80                  85                  90

Gly Thr Asp Phe Thr Leu Thr Ile Ser Ser Leu Gln Pro Glu Asp
            95                  100                 105

Phe Ala Thr Tyr Tyr Cys Gln Gln Tyr Ser Thr Val Pro Trp Thr
            110                 115                 120

Phe Gly Gln Gly Thr Lys Val Glu Ile Lys Arg Thr Val Ala Ala
            125                 130                 135

Pro Ser Val Phe Ile Phe Pro Pro Ser Asp Glu Gln Leu Lys Ser
            140                 145                 150

Gly Thr Ala Ser Val Val Cys Leu Leu Asn Asn Phe Tyr Pro Arg
```

```
                       155                 160                 165
Glu Ala Lys Val Gln Trp Lys Val Asp Asn Ala Leu Gln Ser Gly
                170                 175                 180
Asn Ser Gln Glu Ser Val Thr Glu Gln Asp Ser Lys Asp Ser Thr
                185                 190                 195
Tyr Ser Leu Ser Ser Thr Leu Thr Leu Ser Lys Ala Asp Tyr Glu
                200                 205                 210
Lys His Lys Val Tyr Ala Cys Glu Val Thr His Gln Gly Leu Ser
                215                 220                 225
Ser Pro Val Thr Lys Ser Phe Asn Arg Gly Glu Cys
                230                 235

<210> SEQ ID NO 11
<211> LENGTH: 476
<212> TYPE: PRT
<213> ORGANISM: Artificial sequence
<220> FEATURE:
<223> OTHER INFORMATION: anti-VEGF heavy chain

<400> SEQUENCE: 11

Met Lys Lys Asn Ile Ala Phe Leu Leu Ala Ser Met Phe Val Phe
  1               5                  10                  15
Ser Ile Ala Thr Asn Ala Tyr Ala Glu Val Gln Leu Val Glu Ser
                 20                  25                  30
Gly Gly Gly Leu Val Gln Pro Gly Ser Leu Arg Leu Ser Cys
                 35                  40                  45
Ala Ala Ser Gly Tyr Asp Phe Thr His Tyr Gly Met Asn Trp Val
                 50                  55                  60
Arg Gln Ala Pro Gly Lys Gly Leu Glu Trp Val Gly Trp Ile Asn
                 65                  70                  75
Thr Tyr Thr Gly Glu Pro Thr Tyr Ala Ala Asp Phe Lys Arg Arg
                 80                  85                  90
Phe Thr Phe Ser Leu Asp Thr Ser Lys Ser Thr Ala Tyr Leu Gln
                 95                 100                 105
Met Asn Ser Leu Arg Ala Glu Asp Thr Ala Val Tyr Tyr Cys Ala
                110                 115                 120
Lys Tyr Pro Tyr Tyr Gly Thr Ser His Trp Tyr Phe Asp Val
                125                 130                 135
Trp Gly Gln Gly Thr Leu Val Thr Val Ser Ser Ala Ser Thr Lys
                140                 145                 150
Gly Pro Ser Val Phe Pro Leu Ala Pro Ser Ser Lys Ser Thr Ser
                155                 160                 165
Gly Gly Thr Ala Ala Leu Gly Cys Leu Val Lys Asp Tyr Phe Pro
                170                 175                 180
Glu Pro Val Thr Val Ser Trp Asn Ser Gly Ala Leu Thr Ser Gly
                185                 190                 195
Val His Thr Phe Pro Ala Val Leu Gln Ser Ser Gly Leu Tyr Ser
                200                 205                 210
Leu Ser Ser Val Val Thr Val Pro Ser Ser Ser Leu Gly Thr Gln
                215                 220                 225
Thr Tyr Ile Cys Asn Val Asn His Lys Pro Ser Asn Thr Lys Val
                230                 235                 240
Asp Lys Lys Val Glu Pro Lys Ser Cys Asp Lys Thr His Thr Cys
                245                 250                 255
Pro Pro Cys Pro Ala Pro Glu Leu Leu Gly Gly Pro Ser Val Phe
```

-continued

```
                          260                 265                 270

Leu Phe Pro Pro Lys Pro Lys Asp Thr Leu Met Ile Ser Arg Thr
                    275                 280                 285

Pro Glu Val Thr Cys Val Val Asp Val Ser His Glu Asp Pro
                    290                 295                 300

Glu Val Lys Phe Asn Trp Tyr Val Asp Gly Val Glu Val His Asn
                    305                 310                 315

Ala Lys Thr Lys Pro Arg Glu Glu Gln Tyr Asn Ser Thr Tyr Arg
                    320                 325                 330

Val Val Ser Val Leu Thr Val Leu His Gln Asp Trp Leu Asn Gly
                    335                 340                 345

Lys Glu Tyr Lys Cys Lys Val Ser Asn Lys Ala Leu Pro Ala Pro
                    350                 355                 360

Ile Glu Lys Thr Ile Ser Lys Ala Lys Gly Gln Pro Arg Glu Pro
                    365                 370                 375

Gln Val Tyr Thr Leu Pro Pro Ser Arg Glu Glu Met Thr Lys Asn
                    380                 385                 390

Gln Val Ser Leu Thr Cys Leu Val Lys Gly Phe Tyr Pro Ser Asp
                    395                 400                 405

Ile Ala Val Glu Trp Glu Ser Asn Gly Gln Pro Glu Asn Asn Tyr
                    410                 415                 420

Lys Thr Thr Pro Pro Val Leu Asp Ser Asp Gly Ser Phe Phe Leu
                    425                 430                 435

Tyr Ser Lys Leu Thr Val Asp Lys Ser Arg Trp Gln Gln Gly Asn
                    440                 445                 450

Val Phe Ser Cys Ser Val Met His Glu Ala Leu His Asn His Tyr
                    455                 460                 465

Thr Gln Lys Ser Leu Ser Leu Ser Pro Gly Lys
                    470                 475
```

SEPARATE-CISTRON CONTRUCTS FOR SECRETION OF AGLYCOSYLATED ANTIBODIES FROM PROKARYOTES

CROSS REFERENCE TO RELATED APPLICATIONS

This application claims priority under 35 U.S.C. 119(e) to U.S. Ser. No. 60/256,164 filed Dec. 14, 2000, the entire disclosure of which is hereby incorporated by reference.

FIELD OF THE INVENTION

The present invention relates generally to the fields of molecular biology and protein technology. More specifically, the invention concerns recombinantly produced antibodies and uses thereof.

BACKGROUND OF THE INVENTION

Recent years have seen increasing promises of using antibodies as diagnostic and therapeutic agents for various disorders and diseases. Many research and clinical applications require large quantities of functional antibodies, thus calling for large scale, economic production systems to be employed. Particularly useful is the recombinant production of antibodies using a variety of expression hosts, ranging from prokaryotes such as E. coli or B. subtilis, to yeast, plants, insect cells and mammalian cells. Kipriyanov and Little (1999) Mol. Biotech. 12:173–201.

Compared to other antibody production systems, bacteria, particularly E. coli, provides many unique advantages. The raw materials used (i.e. bacterial cells) are inexpensive and easy to grow, therefore reducing the cost of products. Shorter generation time and ease of scaling up make bacterial fermentation a more practical means for large-scale protein production. The genomic structure and biological activity of many bacterial species, such as E. coli, have been well-studied and a wide range of expression vectors are available, making expression of a desirable antibody more convenient. Compared with eukaryotes, fewer steps are involved in the production process, including the manipulation of recombinant genes, stable transformation of multiple copies into the host, expression induction and characterization of the products. Pluckthun and Pack Immunotech 3:83–105 (1997). In addition, E. coli permits a unique access to random approaches. Because of the unparalleled efficiency for transformation by plasmids or transfection by phages, E. coli systems can be used for phage library construction of many types of antibody variants, which is particularly important in functional genomic studies.

Currently, bacterial systems are used to produce antibody fragments. Like any other heterologous proteins, antibody fragments can be produced in E. coli either through refolding of inclusion bodies expressed in the cytoplasm, or through expression followed by secretion to the bacterial periplasm. The choice between secretion and refolding is generally guided by several considerations. Secretion is generally the faster and more commonly used strategy.

Opper et al., U.S. Pat. No. 6,008,023, describe an E. coli cytoplasmic expression system, wherein antibody fragments (e.g., Fabs) are fused with an enzyme for use in targeted tumor therapy. Zemel-Dreasen et al. Gene 27:315–322 (1984) report the secretion and processing of an antibody light chain in E. coli. Lo et al's PCT publication, WO 93/07896, reports the E. coli production of a tetrameric antibody lacking the CH2 region in its heavy chain. The genes encoding the light chain and the CH2-deleted heavy chain were constructed into the same expression vector, under the control of one single promoter. The authors acknowledged that the expression system was not optimized and the expression level was moderate. A similar polycistronic system, wherein two expression units (i.e., cistrons) were under the control of one promoter, was used by Carter et al. in U.S. Pat. No. 5,648,237, for producing antibody fragments in E. coli.

In contrast to the widespread uses of bacterial systems for expressing antibody fragments, there have been few attempts to express and recover at high yield functional intact antibodies in E. coli. Because of the complex feature and large size of an intact antibody, it is often difficult to achieve proper folding and assembly of the expressed light and heavy chain polypeptides, resulting in poor yield of reconstituted tetrameric antibody. Furthermore, since antibodies made in prokaryotes are not glycosylated, thus lacking the effector functions, the art has suggested that E. coli would not be a useful system for making intact antibodies. Pluckthun and Pack (1997) Immunotech 3:83–105; Kipriyanov and Little Mol. Biotech. 12:173–201 (1999); Pluckthun et al. (1996) in ANTIBODY ENGINEERING: A PRACTICAL APPROACH, pp 203–252 (Oxford Press); Pluckthun (1994) in HANDBOOK OF EXP. PHARMCOL vol 3: The Pharmcol. of Monoclonal Antibodies, pp 269–315 (ed. M. Rosenberg and G. P. Moore; Springer-Verlag, Berlin).

Recent developments in research and clinical studies suggest that in many instances, intact antibodies are preferred over antibody fragments. An intact antibody containing the Fc region tends to be more resistant against degradation and clearance in vivo, thereby having longer biological half life in circulation. This feature is particularly desirable where the antibody is used as a therapeutic agent for diseases requiring sustained therapies.

Furthermore, in many instances, intact antibodies deficient in effector functions are more desirable for therapeutic uses. Friend et al., Transplantation 68: 1632–1637 (1999) describe toxic effects, such as severe cytokine release syndromes, of glycosylated CD3 monoclonal antibodies when used in humans for the treatment of acute rejection episodes of organ allografts. The CD3 antibodies cause T-cell activation and cytokine release by cross-linking the T cell receptor complex as a result of FcR binding. U.S. Pat. No. 5,585,097 describe making aglycosylated CD3 antibodies by mutating certain glycosylation site residues of native CD3 antibodies. Armour et al., Eur. J. Immunol. 29:2613–2624 (1999) describe the use of non-destructive antibodies (i.e., lacking the effector functions) specific for HPA-1a-positive platelets in therapeutic applications where depletion of cells bearing the target antigen (i.e., the platelet cells) is undesirable. Thompson, et al., J. Immunol Meth 227:17–29 (1999) show that effector functions of a fully human antibody against TGFβ2 are not necessary for use in therapy of fibrotic diseases mediated by TGFβ2. Reddy, et al., J. Immunol. 164:1925–1933 (2000) describe liability of strong antibody-Fcγ receptor binding in treating autoimmune diseases; Isaacs, et al., Clin. Exp. Immunol. 106:427–433(1996) suggest that if a pure blocking effect is required in vivo, an aglycosylated monoclonal antibody variant or a mutant engineered to prevent Fc receptor binding may be better choices.

Currently, attempts to eliminate or reduce effector functions of an antibody focus on either using IgG4 isotype, which is thought to be unable to deplete target cells, or making Fc variants, wherein residues in the Fc region critical for effector function(s) are mutated. See, for example, U.S. Pat. No. 5,585,097. However, both of these approaches have limitations. For example, the IgG4 isotype has been shown to retain some level of effector functions, as described by Isaacs, et al. (1996) supra, and Thompson, et al. (1999), supra. Reddy et al. (2000), supra, also report that further alterations of an IgG4 mAb against CD4 were required to eliminate Fc effector functions. Fc mutants may elicit undesirable immune response because of the residue changes in the primary sequence.

SUMMARY OF THE INVENTION

The present invention addresses the need for producing intact antibodies in prokaryotic organisms. In one embodiment, the invention provides a process for producing an immunoglobulin in a prokaryotic host cell, comprising using a uniquely designed separate cistron expression vector. The separate cistron expression vector of the invention comprises a polynucleotide expression cassette, which comprises a first promoter-cistron pair for expression of an immunoglobulin light chain and a second promoter-cistron pair for expression of an immunoglobulin heavy chain, whereby expression of the light chain and heavy chain are independently regulated by separate promoters. Each cistron within the expression cassette polynucleotide comprises a translation initiation region (TIR) operably linked to the nucleic acid sequence coding for the light chain or heavy chain of the full length antibody. In some embodiments, the TIR sequences within the expression vector of the invention are manipulated so to provide different translational strength combinations for light and heavy chains. Many prokaryotic organisms are suitable as hosts for the expression vector of the invention. Preferably, the host is a gram-negative bacteria. More preferably, the host is *E. coli*. In one embodiment, the host cell is a genetically altered *E. coli* strain suitable for large quantity production of heterologous proteins. A number of promoters can be used for the expression vector of the invention. A preferred promoter is the *E. coli* PhoA promoter.

The invention also provides a full length aglycosylated antibody produced in a prokaryotic host using the novel separate cistron expression vector. The invention encompasses various antibody modifications or variants, including but not limited to humanized antibodies, affinity matured antibodies, antibodies with variant Fc regions, multispecific antibodies, and antibody derivatives. Immunoconjugate compositions comprising the full length antibody conjugated to a cytotoxic agent are also contemplated.

Also contemplated are various diagnostic and therapeutic uses of the full length antibodies described herein. In one therapeutic application, the full length antibody is used in combination with another therapeutic agent in a patient.

BRIEF DESCRIPTION OF DRAWINGS

FIG. 1 is a schematic representation of the construction of a full length antibody expression vector, pxTFPV, based on an existing Fab expression vector, pAK19.

FIG. 2 shows *E. coli* expression of full length antibodies using two polycistronic full length antibody expression vectors. Whole cell lysates were analyzed by SDS-PAGE immunoblot following induction. Lane 1 is negative control; lane 2 is pxTFPV (anti-TF antibody); and lane 3 is pY0317.Fab-CH3 (anti-VEGF antibody). The arrow indicates bands corresponding to full length antibodies.

FIG. 3 depicts polycistronic constructs with various TIR translational strength combinations for light and heavy chains.

FIGS. 4A and 4B show *E. coli* expression of full length anti-TF IgG1 using polycistronic vectors with various TIR combinations for light (L) and heavy (H) chains. Whole cell lysates were analyzed by SDS-PAGE immunoblot following induction. (4A) reduced samples. (4B) non-reduced samples. Listed above each lane is the relative TIR translational strength for light ("L") and heavy ("H") chains. "neg.": induced cells harboring only the background vector, pBR322.

FIG. 5 is a schematic representation of the constructions for the individual expression of light and heavy chains under different TIR translational strengths.

FIGS. 6A and 6B are Coomassie stained gel results of reduced whole cell lysate samples for different plasmids, showing the effect of TIR relative strength on the secretion yields of light chain (6A) and heavy chain (6B).

FIG. 7 schematically illustrates the construction of a separate cistron expression vector for full length antibody (pxTF2AP77) by combining light and heavy chain vectors with determined TIR strengths.

FIG. 8 shows Coomassie staining of reduced whole cell lysate transformed with the separate cistron vector pxTF2AP77.

FIG. 9 illustrates separate cistron constructs with various TIR strength combinations for light and heavy chains.

FIGS. 10A and 10B show *E. coli* expression of full length anti-TF IgG1 using separate cistron constructs with various TIR strength combinations for light (L) and heavy (H) chains. Whole cell lysates were analyzed by SDS-PAGE immunoblot following induction. (4A) reduced samples. (4B) non-reduced samples. Listed above each lane is the relative TIR translational strength for light ("L") and heavy ("H") chains. "neg.": induced cells harboring only the background vector, pBR322.

FIG. 11 is a comparison of full length antibody expressions using the polycistronic vs. the separate cistron systems. Non-reduced whole cell lysates were analyzed by SDS-PAGE immunoblot following induction. Various TIR strength combinations for light (L) and heavy (H) chains are indicated.

FIG. 12 is a Coomassie-stained gel comparison of the pAK19-derived polycistronic vector vs. the separate cistron vector for anti-TF antibody. Lane 1 is a negative control; lane 2 is pxTFPV (pAK19-derived polycistronic); and lane 3 is paTF50 (separate cistron). The arrow indicates the position for full length antibodies.

FIG. 13 is a comparison of the full length anti-TF antibody expression using a pAK19-derived polycistronic vector vs. a separate cistron vector. Non-reduced whole cell lysates were analyzed by SDS-PAGE immunoblot following induction. Lane 1 is a negative control; lane 2 is pxTFPV (pAK19-derived polycistronic); and lane 3 is paTF50 (separate cistron). The arrow indicates the band corresponding to full length antibody.

FIG. 14 is a comparison of the full length anti-VEGF antibody expression using a pAK19-derived polycistronic vector vs. a separate cistron vector. Non-reduced whole cell lysates were analyzed by SDS-PAGE immunoblot following induction. Lane 1 is a negative control; lane 2 is pY0317.Fab-CH3 (pAK19-derived polycistronic); and lane 3 is pxVG2AP11 (separate cistron). The arrow indicates the band representing full length anti-VEGF antibody.

FIG. 15 depicts the antigen (TF) binding of the full length anti-TF antibody made by the separate cistron vector paTF50 in *E. coli* (IgG1). Two CHO-made anti-TF antibodies (IgG2 and IgG4) were used as controls.

FIG. 16 depicts the C1q binding of the full length anti-TF antibody IgG1 made by paTF50 in *E. coli*. Another antibody, I-1095-1-Rituximab, was used for comparison.

FIG. 17 depicts the FcγR1 alpha binding of the full length anti-TF antibody made by paTF50 in *E. coli*. Two anti-IgE antibodies made in CHO cells were used as controls.

FIG. 18 depicts the FcRn binding of the full length anti-TF antibody IgG1 made by paTF50 in *E. coli* (32604-74 *E coli* IgG1) in comparison with five other antibodies as controls.

FIG. 19 depicts the plasma anti-TF antibody (ATF-D3H44) concentration (μg/ml) changes over time in chimpanzees given a single IV bolus dose of either the full length IgG1 made by paTF50 in *E. coli* (IgG1 *E. coli*), the IgG2 made in CHO (IgG2 CHO) or the IgG4b made in CHO (IgG4b CHO).

FIGS. 20a–20c show the expression cassette sequences of the separate cistron vector paTF50 (SEQ ID NOS: 1, 8 AND 9).

FIGS. 21a–21c show the expression cassette sequences of the separate cistron vector pxVG2AP11 (SEQ ID NOS: 2, 10 AND 11).

FIG. 22 shows expression of various full length antibodies using the separate cistron system. Whole cell lysates were analyzed by SDS-PAGE immunoblot following induction.

DETAILED DESCRIPTION OF THE PREFERRED EMBODIMENTS

I. Definitions

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. "Adjacent control regions" include, for example, a translational initiation region (TIR; as defined herein below) and a termination region.

A "polycistronic" expression vector refers to a single vector that contains and expresses multiple cistrons under the regulatory control of one single promoter. A common example of polycistronic vector is a "dicistronic" vector that contains and expresses two different polypeptides under the control of one promoter. Upon expression of a dicistronic or polycistronic vector, multiple genes are first transcribed as a single transcriptional unit, and then translated separately.

A "separate cistron" expression vector according to the present invention refers to a single vector comprising at least two separate promoter-cistron pairs, wherein each cistron is under the control of its own promoter. Upon expression of a separate cistron expression vector, both transcription and translation processes of different genes are separate and independent.

The "translation initiation region" or TIR, as used herein refers to a nucleic acid region providing the efficiency of translational initiation of a gene of interest. In general, a TIR within a particular cistron encompasses the ribosome binding site (RBS) and sequences 5' and 3' to RBS. The RBS is defined to contain, minimally, the Shine-Dalgarno region and the start codon (AUG). Accordingly, a TIR also includes at least a portion of the nucleic acid sequence to be translated. Preferably, a TIR of the invention includes a secretion signal sequence encoding a signal peptide that precedes the sequence encoding for the light or heavy chain within a cistron. A TIR variant contains sequence variants (particularly substitutions) within the TIR region that alter the property of the TIR, such as its translational strength as defined herein below. Preferably, a TIR variant of the invention contains sequence substitutions within the first 2 to about 14, preferably about 4 to 12, more preferably about 6 codons of the secretion signal sequence that precedes the sequence encoding for the light or heavy chain within a cistron.

The term "translational strength" as used herein refers to a measurement of a secreted polypeptide in a control system wherein one or more variants of a TIR is used to direct secretion of a polypeptide and the results compared to the wild-type TIR or some other control under the same culture and assay conditions. Without being limited to any one theory, "translational strength" as used herein can include, for example, a measure of mRNA stability, efficiency of ribosome binding to the ribosome binding site, and mode of translocation across a membrane.

"Secretion signal sequence" or "signal sequence" refers to a nucleic acid sequence encoding for a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be exogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

The term "host cell" (or "recombinant host cell"), as used herein, is intended to refer to a cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "antibody" and "immunoglobulin" are used interchangeably in the broadest sense and includes monoclonal antibodies (full length or intact monoclonal antibodies), polyclonal antibodies, multivalent antibodies, and multispecific antibodies (e.g., bispecific antibodies so long as they exhibit the desired biological activity). A naturally occurring antibody comprises four polypeptide chains, two identical heavy (H) chains and two identical light (L) chains inter-connected by disulfide bonds. Each heavy chain is comprised of a heavy chain variable region ($V_H$) and a heavy chain constant region. The heavy chain constant region is comprised of three domains, CH1, CH2 and CH3. Each light chain is comprised of a light chain variable region ($V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The light chains of antibodies from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contains the Fc region. A full length antibody can be a native sequence antibody or an antibody variant. A full length antibody can be human, humanized and/or affinity matured.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) isolated CDR regions; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) "linear antibodies" comprising a pair of tandem Fd segments (VH-CH1-VH-CH1) which, together with complementary light chain polypeptides, form a pair of antigen binding regions.

A "biologically active" or "functional" immunoglobulin is one capable of exerting one or more of its natural activities in structural, regulatory, biochemical or biophysical events. For example, a biologically active antibody may have the ability to specifically bind an antigen and the binding may in turn elicit or alter a cellular or molecular event such as signaling transduction or enzymatic activity. A biologically active antibody may also block ligand activation of a receptor or act as an agonist antibody. The capability of a full length antibody to exert one or more of its natural activities depends on several factors, including proper folding and assembly of the polypeptide chains. As used herein, the biologically active immunoglobulins generated by the disclosed methods are typically heterotetramers having two identical L chains and two identical H chains that are linked by multiple disulfide bonds and properly folded.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851–6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al, Nature 321:522–525 (1986); Riechmann et al., Nature 332:323–329 (1988); and Presta, Curr. Op. Struct. Biol. 2:593–596 (1992). See also the following review articles and references cited therein: Vaswani and Hamilton, *Ann. Allergy, Asthma & Immunol.* 1:105–115 (1998); Harris, *Biochem. Soc. Transactions* 23:1035–1038 (1995); Hurle and Gross, *Curr. Op. Biotech.* 5:428–433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779–783 (1992) describes affinity maturation by VH and VL domain shuffling. Random mutagenesis of CDR and/or framework residues is described by: Barbas et al. *Proc Nat. Acad. Sci, USA* 91:3809–3813 (1994); Schier et al. *Gene* 169:147–155 (1995); Yelton et al. *J. Immunol.* 155:1994–2004 (1995); Jackson et al., *J. Immunol.* 154(7):3310–9 (1995); and Hawkins et al, *J. Mol. Biol.* 226:889–896 (1992).

The term "Fc region" is used to define the C-terminal region of an immunoglobulin heavy chain which may be generated by papain digestion of an intact antibody. The Fc region may be a native sequence Fc region or a variant Fc region. Although the boundaries of the Fc region of an immunoglobulin heavy chain might vary, the human IgG heavy chain Fc region is usually defined to stretch from an amino acid residue at about position Cys226, or from about position Pro230, to the carboxyl-terminus of the Fc region. The Fc region of an immunoglobulin generally comprises two constant domains, a CH2 domain and a CH3 domain, and optionally comprises a CH4 domain. By "Fc region chain" herein is meant one of the two polypeptide chains of an Fc region.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457–92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652–656 (1998).

The terms "Fc receptor" and "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daëron, *Annu. Rev. Immunol.* 15:203–234 (1997)). FcRs are reviewed in Ravetch and Kinet, *Annu. Rev. Immunol* 9:457–92 (1991); Capel et al., *Immunomethods* 4:25–34 (1994); and de Haas et al., *J. Lab. Clin. Med.* 126:330–41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976); and Kim et al., *J. Immunol.* 24:249 (1994)).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Affinity binding" refers to the strength of the sum total of noncovalent interactions between a single binding site of a molecule (e.g., an antibody) and its binding partner (e.g., an antigen or FcRn receptor). The affinity of a molecule X for its partner Y is represented by the dissociation constant (Kd), which is the concentration of Y that is required to occupy the combining sites of half the X molecules present in a solution. Low-affinity antibodies bind antigen (or FcRn receptor) weakly and tend to dissociate readily, whereas high-affinity antibodies bind antigen (or FcRn receptor) more tightly and remain bound longer.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin $\gamma_1^I$ and calicheamicin $\theta^I_1$, see, e.g., Agnew *Chem Intl. Ed. Engl.* 33:183–186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A "blocking" antibody or an "antagonist" antibody is one which inhibits or reduces biological activity of the antigen it binds. Such blocking can occur by any means, e.g. by interfering with: ligand binding to the receptor, receptor complex formation, tyrosine kinase activity of a tyrosine kinase receptor in a receptor complex and/or phosphorylation of tyrosine kinase residue(s) in or by the receptor. For example, a VEGF antagonist antibody binds VEGF and inhibits the ability of VEGF to induce vascular endothelial cell proliferation. Preferred blocking antibodies or antagonist antibodies completely inhibit the biological activity of the antigen.

An "agonist antibody" is an antibody which binds and activates antigen such as a receptor. Generally, the receptor activation capability of the agonist antibody will be at least qualitatively similar (and may be essentially quantitatively similar) to a native agonist ligand of the receptor.

An antibody of the invention "which binds antigen essentially as effectively as" a corresponding antibody made in a mammalian cell system, is one capable of binding that antigen with affinity or avidity that is within about 10 fold, preferably about 5 fold, and more preferably about 2 fold, of the binding affinity of an antibody that is expressed by a mammalian cell, such as a Chinese Hamster Ovary (CHO) cell.

A "disorder" is any condition that would benefit from treatment with the antibody. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE); diabetes mellitus (e.g. Type I diabetes mellitus or insulin dependent diabetes mellitis); multiple sclerosis; Reynaud's syndrome; autoimmune thyroiditis; allergic encephalomyelitis; Sjorgen's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiffman syndrome; Behcet disease; giant cell arteritis; immune complex nephritis; IgA nephropathy; IgM polyneuropathies; immune thrombocytopenic purpura (ITP) or autoimmune thrombocytopenia etc.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

An "effective amount" refers to an amount effective, at dosages and for periods of time necessary, to achieve the desired therapeutic or prophylactic result. A "therapeutically effective amount" of the antibody may vary according to factors such as the disease state, age, sex, and weight of the individual, and the ability of the antibody to elicit a desired response in the individual. A therapeutically effective amount is also one in which any toxic or detrimental effects of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

II. Mode(s) for Carrying out the Invention

The present invention concerns the recombinant production of immunoglobulins in a prokaryotic system. The invention is based on a uniquely designed expression vector, in which the expressions of an immunoglobulin light chain and an immunoglobulin heavy chain are independently modulated (i.e., a separate cistron system). As illustrated in some of the examples provided herein, significant problems are associated with existing prokaryotic systems for antibody production, in which the transcription of light and heavy chain genes are under the control of one promoter (i.e., the polycistronic systems). Such systems tend to create unbalanced expression levels of the two immunoglobulin chains. When two genes are expressed from a single transcriptional unit, the first gene is typically expressed at a higher level than the second gene. This effect results from the translational dependency of the second gene on such additional factors as the efficiency of ribosomal coupling between the two genes. Accordingly, the polycistronic system produces an excess of light chain over heavy chain. This particular issue could in theory be improved by experimentally increasing the translational coupling. However, even if efficient translational coupling could be obtained between the chains, the polycistronic system creates an additional hurdle in complicating the determination of preferred light to heavy chain expression ratios. Since both chains are tied together on the same message, manipulating the translation of the first gene (light chain) affects the translation of the second gene (heavy chain). Considerable time and effort would be required to overcome such a complicated arrangement to achieve desirable ratios of light to heavy chain expression.

It has now been surprisingly discovered that the problem associated with the polycistronic system can be solved by using a separate cistron system, wherein each of the cistrons for light chain and heavy chain genes is paired with, and under the control of, a separate promoter, thus allowing separation and independence of both transcription and translation of the two genes. While it is generally desirable to obtain high expression levels for individual chains of an antibody, more important for maximizing production of full length, correctly folded, biologically active antibodies is obtaining desirable ratios of light to heavy chain expression.

While the separate cistron expression system of the present invention is mainly illustrated for the production of immunoglobulins, it should be understood that the approach described herein is applicable in any system in which multimeric proteins are to be produced and the final protein complex requires proper assembly of individual units/chains in order to be functional. The approach is especially useful for the production of protein complexes containing disulfide bonds including for example, but not limited to, T-cell receptors, class I and class II MHC molecules, integrins, CD8, CD28 and Factor VIII molecules, and related derivatives, variants and fusion proteins.

Antigen Specificity

The present invention is applicable to antibodies of any appropriate antigen binding specificity. Preferably, the antibodies of the invention are specific to antigens that are biologically important polypeptides. More preferably, the antibodies of the invention are useful for therapy or diagnosis of diseases or disorders in a mammal. The full length aglycosylated antibodies made according to the present invention are particularly useful as therapeutic antibodies such as blocking antibodies, agonist antibodies or antibody conjugates. Non-limiting examples of therapeutic antibodies include anti-VEGF, anti-IgE, anti-CD11, anti-CD18, anti-CD40, anti-tissue factor (TF), anti-HER2, and anti-TrkC antibodies. Antibodies directed against non-polypeptide antigens (such as tumor-associated glycolipid antigens) are also contemplated.

Where the antigen is a polypeptide, it may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD3, CD4, CD8, CD19, CD20 and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred antigens for antibodies encompassed by the present invention include CD proteins such as CD3, CD4, CD8, CD19, CD20, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, $\alpha$4/$\beta$7 integrin, and $\alpha$v/$\beta$3 integrin including either $\alpha$ or $\beta$ subunits thereof (e.g. anti-CD11a, anti-CD18 or anti-CD11b antibodies); growth factors such as VEGF; tissue factor (TF); TGF-$\beta$ alpha interferon ($\alpha$-IFN); an interleukin, such as IL-8; IgE; blood group antigens Apo2, death receptor; flk2/flt3 receptor; obesity (OB) receptor; mpl receptor; CTLA-4; protein C etc. The most preferred targets herein are VEGF, TF, CD19, CD20, CD40, TGF-$\beta$, CD11a, CD18, Apo2 and C24.

Soluble antigens or fragments thereof, optionally conjugated to other molecules, can be used as immunogens for generating antibodies. For transmembrane molecules, such as receptors, fragments of these molecules (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

The antibodies of the present invention may be monospecific, bispecific, trispecific or of greater multispecificity. Multispecific antibodies may be specific to different epitopes of a single molecule or may be specific to epitopes on different molecules. Methods for designing and making multispecific antibodies are known in the art. See, e.g., Millstein et al. (1983) *Nature* 305:537–539; Kostelny et al. (1992) *J. Immunol.* 148:1547–1553; WO 93/17715.

Vector Construction

Polynucleotide sequences encoding the immunoglobulin light and heavy chains of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the light and heavy chains are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237, and the "Examples" section herein below.

In addition, phage vectors containing replicon and control sequences that are compatible with the host microorganism can be used as transforming vectors in connection with these hosts. For example, bacteriophage such as $\lambda$GEM.TM.-11 may be utilized in making a recombinant vector which can be used to transform susceptible host cells such as *E. coli* LE392.

The expression vector of the invention comprises at least two promoter-cistron pairs, one for the immunoglobulin light chain and the other for the immunoglobulin heavy chain. Promoter is an untranslated regulatory sequence located upstream (5') to a cistron that modulate its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

Although both constitutive and inducible promoters can be used in the present invention, inducible promoters under high regulation are preferred in the expression vectors disclosed herein. A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites. More preferred promoter for use in this invention is the PhoA promoter.

In one aspect of the present invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In a preferred embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

The present invention provides an expression system in which the quantitative ratio of expressed light and heavy chains can be modulated in order to maximize the yield of secreted and properly assembled full length antibodies. Such modulation is accomplished by simultaneously modulating translational strengths for light and heavy chains.

One technique for modulating translational strength is disclosed in Simmons et al. U.S. Pat. No. 5, 840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One preferred method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151–158.

Preferably, a set of vectors is generated with a range of TIR strengths for each cistron therein. This limited set provides a comparison of expression levels of each chain as well as the yield of full length products under various TIR strength combinations. TIR strengths can be determined by quantifying the expression level of a reporter gene as described in detail in Simmons et al. U.S. Pat. No. 5,840, 523. For the purpose of this invention, the translational strength combination for a particular pair of TIRs within a vector is represented by (N-light, M-heavy), wherein N is the relative TIR strength of light chain and M is the relative TIR strength of heavy chain. For example, (3-light, 7-heavy) means the vector provides a relative TIR strength of about 3 for light chain expression and a relative TIR strength of about 7 for heavy chain expression. Based on the translational strength comparison, the desired individual TIRs are selected to be combined in the expression vector constructs of the invention.

Prokaryotic host cells suitable for expressing full length antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. Preferably, gram-negative cells are used. More preferably, *E. coli* cells are used as hosts for the invention. Preferred *E. coli* strain are strain W3110 (Bachmann, *Cellular and Molecular Biology*, vol. 2 (Washington, D.C.: American Society for Microbiology, 1987), pp. 1190–1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639, 635). Of course other strains and derivatives thereof, such as *E. coli* 294 (ATCC 31,446), *E. coli* B, *E. coli*$_λ$ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309–314 (1990). It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Preferably the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, two PhoA promoters are used for controlling transcription of the light and heavy chains. Accordingly, the transformed host cells are cultured in a phosphate-limiting medium for induction. Preferably, the phosphate-limiting medium is the C.R.A.P medium, as described in detail below in Example 2. A variety of other inducers may be used, according to the vector construct employed, as is known in the art.

The expressed light and heavy chain polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, the antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180–220, at which stage the cells are in the early stationary phase. A variety of inducers may be used, according to the vector construct employed, as is known in the art and described above. Cells may be grown for shorter periods prior to induction. Cells are usually induced for about 12–50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601–19605; Georgiou et al., U.S. Pat. No. 6,083,715; Georgiou et al., U.S. Pat. No. 6,027,888; Bothmann and Pluckthun (2000) *J. Biol. Chem.* 275:17100–17105; Ramm and Pluckthun (2000) *J. Biol. Chem.* 275:17106–17113; Arie et al. (2001) *Mol. Microbiol.* 39:199–210. Sufficient disulfide bonds are particularly important for the formation and folding of full length, bivalent antibodies having two heavy chains and two light chains.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance,* 2:63–72 (1996).

In a preferred embodiment, *E. coli* strains deficient for proteolytic enzymes and transformed with plasmids overexpressing one or more chaperone proteins are used as host cells in the expression system of the invention. Some of these strains are further described in the Examples section below.

Antibody Purification

In a preferred embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) *J. Immunol. Meth.* 62:1–13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the full length antibody to Protein A. The solid phase is then washed to remove contaminants non-specifically bound to the solid phase. Finally the full length antibody is recovered from the solid phase by elution.

Activity Assays

The full length, aglycosylated antibody of the present invention can be characterized for its physical/chemical properties and biological functions by various assays known in the art. In one aspect of the invention, it is important to compare the antibody made in the prokaryotic host cells of the present invention to similar antibodies made in other expression systems, such as different expression vector designs or different host cell systems. Particularly, the quantity of the full length antibody expressed by the separate-cistron vector of the present invention can be compared to those expressed by various polycistronic vectors. Methods for protein quantification are well known in the art. For example, samples of the expressed proteins can be compared for their quantitative intensities on a Coomassie-stained SDS-PAGE. Alternatively, the specific band(s) of interest (e.g., the full length band) can be detected by, for example, western blot gel analysis and/or AME5-RP assay.

The purified full length antibody can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the full length antibody produced herein is analyzed for its biological activity. Preferably, the antibody of the present invention is tested for its antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An exemplary antigen binding assay is provided below in the Examples section.

In one embodiment, the present invention contemplates a full length antibody that is aglycosylated. The unique features of the antibody (i.e., having an intact Fc region, yet lacking effector functions) make it a desired candidate for many applications in which the half life of the antibody in vivo is important yet the effector functions (i.e., complement and ADCC) are unnecessary or deleterious. In certain embodiments, the Fc activities of the produced full length antibody are measured to ensure that only the desirable properties are maintained. For example, Fc receptor (FcR) binding assays can be conducted to ensure that the antibody lacks FcγR1 binding (hence lacks ADCC toxicity), but retains FcRn binding ability. C1q binding assays may also be carried out to confirm that the antibody is unable to bind C1q and hence lacks CDC activity. In vitro and in vivo cytotoxicity assays can be conducted to confirm the depletion of CDC and or ADCC activities. Techniques for carrying out these assays are known in the art. Exemplary procedure details are provided in the Examples section.

Humanized Antibodies

The present invention encompasses humanized antibodies. Various methods for humanizing non-human antibodies are known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522–525; Riechmann et al. (1988) *Nature* 332:323–327; Verhoeyen et al. (1988) *Science* 239:1534–1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244:1081–1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed full length antibodies are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6–7 sites) are mutated to generate all possible amino substitutions at each site. The full length antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the full length antibody of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an FcγR may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an FcγRI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an FcγRIII and comprise an amino acid modification at any one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter *Nature* 322:738–40 (1988); U.S. Pat. Nos. 5,648,260; 5,624, 821; and WO94/29351 concerning Fc region variants.

Immunoconjugates

The invention also pertains to immunoconjugates comprising an antibody conjugated to a cytotoxic agent such as a chemotherapeutic agent (as defined and described herein above), toxin (e.g. a small molecule toxin or an enzymatically active toxin of bacterial, fungal, plant or animal origin, including fragments and/or variants thereof), or a radioactive isotope (i.e., a radioconjugate).

Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127–131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al. *Cancer Research* 53: 3336–3342 (1993) and Lode et al. *Cancer Research* 58: 2925–2928 (1998)). See, also, U.S. Pat. Nos. 5,714,586; 5,712,374; 5,264,586; and 5,773,001.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127–131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

Antibody Derivatives

The antibodies and antibody variants of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and or type of polymers used for derivatization can be determined based on considerations including, but not limited to, the particular properties or functions of the antibody to be improved, whether the antibody derivative will be used in a therapy under defined conditions.

In general, the full length antibody produced by the prokaryotic expression system described herein is aglycosylated and lacks the effector activities of the Fc region. In some instances, it may be desirable to at least partially restore one or more effector functions of the native full length antibody. Accordingly, the present invention contemplates a method for restoring the effector function(s) by attaching suitable moieties to identified residue sites in the Fc region of the aglycosylated full length antibody. A preferred moiety for this purpose is PEG, although other carbohydrate polymers can also be used. Pegylation may be carried out by any of the pegylation reactions known in the art. See, for example, EP 0401384; EP 0154316; WO 98/48837. In one embodiment, cysteine residues are first substituted for residues at identified positions of the antibody, such as those positions wherein the antibody or antibody variant is normally glycosylated or those positions on the surface of the antibody. Preferably, the cysteine is substituted for residue(s) at one or more positions 297, 298, 299, 264, 265 and 239 (numbering according to the EU index as in Kabat). After expression, the cysteine substituted antibody variant can have various forms of PEG (or pre-synthesized carbohydrate) chemically linked to the free cysteine residues.

Pharmaceutical Formulations

Therapeutic formulations of the full length antibody are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the full length antibody, which matrices are in the form of shaped articles, e.g., films, or microcapsule. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used, for example, to purify, detect, and target a specific polypeptide it recognizes, including both in vitro and in vivo diagnostic and therapeutic methods.

In one aspect, an antibody of the invention can be used in immunoassays for qualitatively and quantitatively measuring specific antigens in biological samples. Conventional methods for detecting antigen-antibody binding includes, for example, an enzyme linked immunosorbent assay (ELISA), an radioimmunoassay (RIA) or tissue immunohistochemistry. Many methods may use a label bound to the antibody for detection purposes. The label used with the antibody is any detectable functionality that does not interfere with its binding to antibody. Numerous labels are known, including the radioisotopes $^{32}P$, $^{32}S$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotin/avidin, spin labels, bacteriophage labels, stable free radicals, imaging radionuclides (such as Technecium) and the like.

Conventional methods are available to bind these labels covalently to the antibody polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. *Nature* 144: 945 (1962); David et al. *Biochemistry* 13:1014–1021 (1974); Pain et al. *J. Immunol. Methods* 40:219–230 (1981); and Nygren *Histochem. and Cytochem* 30:407–412 (1982). Preferred labels herein are enzymes such as horseradish peroxidase and alkaline phosphatase. The conjugation of such label, including the enzymes, to the antibody polypeptide is a standard manipulative procedure for one of ordinary skill in immunoassay techniques. See, for example, O'Sullivan et al., "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, N.Y., 1981), pp. 147–166. Such bonding methods are suitable for use with the antibody polypeptides of this invention.

Alternative to labeling the antibody, antigen can be assayed in biological fluids by a competition immunoassay utilizing a competing antigen standard labeled with a detectable substance and an unlabeled antibody. In this assay, the biological sample, the labeled antigen standards and the antibody are combined and the amount of labeled antigen standard bound to the unlabeled antibody is determined. The amount of tested antigen in the biological sample is inversely proportional to the amount of labeled antigen standard bound to the antibody.

In one aspect, the aglycosylated full length antibody of the invention is particularly useful to detect and profile expressions of specific surface antigens in vitro or in vivo. As discussed before, the aglycosylated full length antibody does not exert effector functions (i.e., ADCC or CDC activity). Therefore, when the antibody binds to the cell surface antigen, it will not initiate undesirable cytotoxic events. The surface antigen can be specific to a particular cell or tissue type, therefore serving as a marker of the cell or tissue type. Preferably, the surface antigen marker is differentially expressed at various differentiation stages of particular cell or tissue types. The full length antibody directed against such surface antigen can thus be used for the screening of cell or tissue populations expressing the marker. For example, the antibody of the invention can be used for the screening and isolation of stem cells such as embryonic stem cells, hematopoietic stem cells and mesenchymal stem cells. The antibody of the invention can also be used to detect tumor cells expressing tumor-associated surface antigens such HER2, HER3 or HER4 receptors.

A full length antibody of the invention may be used as an affinity purification agent. In this process, the full length antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized full length antibody. Finally, the support is washed with another suitable solvent, such as glycine buffer, pH 5.0, that will release the antigen from the full length antibody.

The antibodies of the invention can be used as an antagonist to partially or fully block the specific antigen activity both in vitro and in vivo. Moreover, at least some of the antibodies of the invention, can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In another embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but not limited to, anti-VEGF, anti-IgE, anti-CD11 and anti-tissue factor antibodies. The antibodies of the invention can be used to diagnose, treat, inhibit or prevent diseases, disorders or conditions associated with abnormal expression and or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, the blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. The antibody of the invention can also act as an agonist of a particular antigen receptor, thereby potentiating, enhancing or activating either all or partial activities of the ligand-mediated receptor activation.

In certain embodiments, an immunoconjugate comprising the antibody conjugated with a cytotoxic agent is administered to the patient. Preferably, the immunoconjugate and/or antigen to which it is bound is/are internalized by the cell, resulting in increased therapeutic efficacy of the immunoconjugate in killing the target cell to which it binds. In a preferred embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the present invention can be used either alone or in combination with other compositions in a therapy. For instance, the antibody may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where the full length antibody inhibits tumor growth, it may be particularly desirable to combine the full length antibody with one or more other therapeutic agent(s) which also inhibits tumor growth. For instance, anti-VEGF antibodies blocking VEGF activities may be combined with anti-ErbB antibodies (e.g. HERCEPTIN® anti-HER2 antibody) in a treatment of metastatic breast cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the full length antibody can occur prior to, and/or following, administration of the adjunct therapy or therapies.

The full length antibody (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the full length antibody is suitably administered by pulse infusion, particularly with declining doses of the antibody. Preferably the dosing is given by injections, most preferably intravenous or subcutaneous injections, depending in part on whether the administration is brief or chronic.

The full length antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The full length antibody need not be, but is optionally formulated with one or more agents currently used to prevent or treat the disorder in question. The effective amount of such other agents depends on the amount of full length antibody present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of the full length antibody (when used alone or in combination with other agents such as chemotherapeutic agents) will depend on the type of disease to be treated, the type of antibody, the severity and course of the disease, whether the full length antibody is administered for preventive or therapeutic purposes, previous therapy, the patient's clinical history and response to the full length antibody, and the discretion of the attending physician. The antibody is suitably administered to the patient at one time or over a series of treatments. Depending on the type and severity of the disease, about 1 $\mu$g/kg to 15 mg/kg (e.g. 0.1 mg/kg–10 mg/kg) of antibody is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another embodiment of the invention, an article of manufacture containing materials useful for the treatment of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a full length antibody of the invention. The label or package insert indicates that the composition is used for treating the condition of choice, such as cancer. Moreover, the article of manufacture may comprise (a) a first container with a composition contained therein, wherein the composition comprises a full length antibody; and (b) a second container with a composition contained therein, wherein the composition comprises a further cytotoxic agent. The article of manufacture in this embodiment of the invention may further comprise a package insert indicating that the first and second antibody compositions can be used to treat cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following examples are intended merely to illustrate the practice of the present invention and are not provided by way of limitation. The disclosures of all patent and scientific literatures cited herein are expressly incorporated in their entirety by reference.

EXAMPLES

Example 1

Construction of Expression Vectors

Various expression vectors were made for the expression of antibodies specific to tissue factor (anti-TF antibody) and antibodies specific to vascular endothelial cell growth factor (anti-VEGF antibody). For each vector construction, an expression cassette was cloned into the framework of the *E. coli* plasmid pBR322 at the EcoRI site. Sutcliffe (1978) Cold Spring Harbor Symp. Quant. Biol. 43:77–90. Each expression cassette contains at least the following components: (1) a phoA promoter for the control of transcription; (2) a Shine-Dalgarno sequence from the *E. coli* trp or the heat stable enterotoxin II (STII) gene, or a combination of both, for translation initiation; and (3) a $\lambda t_0$ terminator to end transcription. The basic components of bacterial expression cassettes are known in the art and have been described in, for example, Kikuchi et al., *Nucleic Acids Res.* 9(21):5671–5678 (1981) (for phoA promoter); Scholtissek and Grosse, *Nucleic Acids Res.* 15:3185 (1987) (for $\lambda t_0$ terminator); Yanofsky et al., *Nucleic Acids Res.* 9:6647–6668 (1981) (for trp); Picken et al., *Infect. Immun.* 42:269–275 (1983) for STII); and Chang et al., *Gene* 55:189–196 (1987) (for combination use of trp and STII Shine-Dalgarno sequence). Additionally, the STII signal sequence or silent codon variants thereof precedes the coding sequence for light or heavy chain and directs the secretion of the polypeptide into periplasm. Picken et al., *Infect. Immun.* 42:269–275 (1983); Simmons and Yansura, *Nature Biotechnology* 14:629–634 (1996).

Polycistronic Vectors

In order to illustrate the enhanced properties of the separate cistron systems of the present invention, several polycistronic vectors for full length antibodies were constructed for comparisons. In a polycistronic vector, the two cistrons for light and heavy chain genes are under the transcriptional control of one single PhoA promoter.

The initial polycistronic vector for anti-TF antibody expression, pxTFPV, was constructed using the expression cassette of a previously published vector, pAK19, which was for antibody fragment Fab' expression. Carter et al. (1992) *Bio/Technology* 10:12–16. The structure of the original pAK19 and the construction of the full length version pxTFPV are illustrated in FIG. 1. The expression cassette contains, from 5' to 3' end, a PhoA promoter, the cistron for light chain, the cistron for heavy chain and a transcription terminator $\lambda_{t0}$. The distance between the light chain stop codon and the start of the STII signal sequence preceding the heavy chain is 81 base pairs. To construct a polycistronic anti-VEGF vector, the coding sequences for anti-VEGF light and heavy chains were substituted for the coding sequences of anti-TF light and heavy chains in pxTFPV. The anti-VEGF expression cassette was further modified by deleting the ~50 bp HindIII fragment upstream of the PhoA promoter and several nucleotide changes were also made in the untranslated region upstream of the heavy chain Shine-Dalgarno sequence. The resulting polycistronic vector for anti-VEGF is named pY0317.Fab_CH3.

Several additional polycistronic anti-TF constructs, paTF20, paTF30, paTF40, paTF90, paTF110, paTF100, paTF120, were similarly made. The expression cassette sequences of these polycistronic plasmids differ from that of pxTFPV mainly in the 5' untranslated region and in the region preceding the secretion signal sequence for the heavy chain. Additionally, depending upon the construct, silent codon differences also exist in the STII signal sequence between pxTFPV and some of the additional polycistronic plasmids. Simmons and Yansura, *Nature Biotechnology*, 14:629–634 (1996).

Separate Cistron Vectors

Figure 20A:
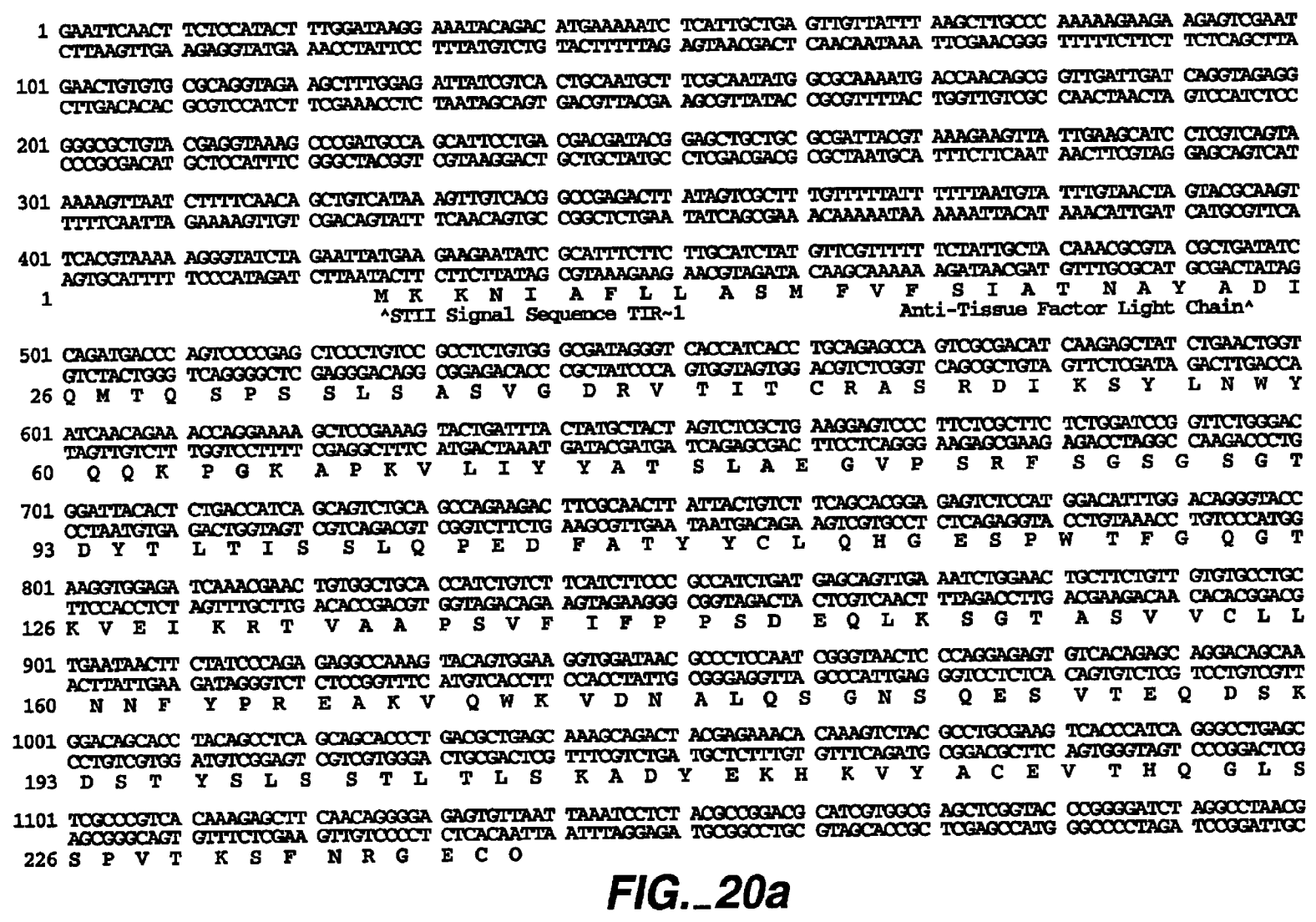

To practice the present invention, vectors with separate cistrons were designed to provide independent expression of the immunoglobulin light and heavy chain genes. In such vectors, the cistron unit for each chain is under the control of its own PhoA promoter and is followed by a $\lambda t_0$ terminator. Furthermore, each cistron unit comprises a TIR upstream of the coding sequence for light or heavy chain. The construction of a separate cistron vector is illustrated in FIG. 7. The expression cassette comprises, from 5' to 3', a first PhoA promoter followed by the cistron for light chain (TIR-L+Light Chain) and the first $\lambda t_0$ terminator, and a second PhoA promoter followed by the cistron for heavy chain (TIR-H+Heavy Chain) and the second $\lambda t_0$ terminator. Both TIR-L and TIR-H further contain therein an STII secretion signal sequence or its variant. The expression cassette sequences of paTF50 (for anti-TF; SEQ ID NO:1) and pxVG2AP11 (for anti-VEGF; SEQ ID NO:2) are provided in FIGS. 20 and 21, respectively. Additional separate cistron vectors for anti-TF, paTF70, paTF60, paTF80, paTF130, paTF140, and pxTF2AP77 represent various combinations of TIR strengths for light and heavy chain translations and differ from paTF50 with respect to silent codon changes in the STII signal sequence, as previously described. Simmons and Yansura, *Nature Biotechnology*, 14:629–634 (1996).

Example 2

*E. coli* Expression of Full Length Antibodies Using Polycistronic Vectors

Full length antibodies were first made in *E. coli* using polycistronic vectors derived from a published vector, pAK19, according to the methods described in Example 1. Small scale inductions were first performed to evaluate and compare the expression levels obtained with the various constructs.

Materials and Methods

For small scale expression of each construct, the *E. coli* strain 33D3 (W3110 ΔfhuA (ΔtonA) ptr3 lac Iq lacL8 ΔompTΔ(nmpc-fepE) degP41 kan$^R$) was used as host cells. Following transformation, selected transformant picks were inoculated into 5 ml Luria-Bertani medium supplemented with carbenicillin (50 ug/ml) and grown at 30° C. on a culture wheel overnight. Each culture was then diluted (1:50 or 1:100) into C.R.A.P. phosphate-limiting media (3.57 g (NH4)2SO4, 0.71 g NaCitrate-2H2O, 1.07 g KCl, 5.36 g Yeast Extract (certified), 5.36 g HycaseSF-Sheffield, adjusted pH with KOH to 7.3, qs to 872 ml with SQ H2O and autoclaved; cool to 55° C. and supplemented with 110 ml 1M MOPS pH 7.3, 11 ml 50% glucose, 7 ml 1M MgSO4). Carbenicillin was then added to the induction culture at a concentration of 50 ug/ml and the culture was grown for approximately 24 hours at 30° C. on a culture wheel. Unless otherwise noted, all shake flask inductions were performed in a 2 ml volume.

Non-reduced whole cell lysates from induced cultures were prepared as follows: (1) 1 $OD_{600}$-ml pellets were centrifuged in a microfuge tube; (2) each pellet was resuspended in 90 ul TE (10 mM Tris pH 7.6, 1 mM EDTA); (3) 10 ul of 100 mM iodoacetic acid (Sigma 1-2512) was added to each sample to block any free cysteines and prevent disulfide shuffling; (4) 20 ul of 10% SDS was added to each sample. The samples were vortexed, heated to about 90° C. for ~3 minutes and then vortexed again. After the samples had cooled to room temperature, ~750–1000 ul acetone was added to precipitate the protein. The samples were vortexed and left at room temperature for about 15 minutes. Following centrifugation for 5 minutes in a microcentrifuge, the supernatant of each sample was aspirated off and each protein pellet was resuspended in 50 ul $dH_2O$+50 ul 2× NOVEX sample buffer. The samples were then heated for ~3–5 minutes at about 90° C., vortexed well and allowed to cool to room temperature. A final 5 minute centrifugation was then done and the supernatants were transferred to clean tubes.

Reduced samples were prepared by following steps similar to what is described above for non-reduced samples, except that 10 ul of 1M DTT was added to the cell resuspension solution in Step (2) and the addition of IAA was omitted in Step (3). Reducing agent was also added to a concentration of 100 mM when the protein precipitate was resuspended in 2× sample buffer+$dH_2O$.

Following preparation, 5–10 ul of each sample was loaded onto a 10 well, 1.0 mm NOVEX manufactured 12% Tris-Glycine SDS-PAG and electrophoresed at ~120 volts for 1.5–2 hours. The resulting gels were then either stained with Coomassie Blue or used for Western blot analysis.

For Western blot analysis, the SDS-PAGE gels were electroblotted onto a nitrocellulose membrane (NOVEX). The membrane was then blocked using a solution of 1× NET (150 mM NaCl, 5 mM EDTA, 50 mM Tris pH 7.4, 0.05% Triton X-100)+0.5% gelatin for approximately 30 min.–1 hour rocking at room temperature. Following the blocking step, the membrane was placed in a solution of 1× NET+ 0.5% gelatin+anti-Fab antibody (peroxidase-conjugated goat IgG fraction to human IgG Fab; CAPPEL #55223). The anti-Fab antibody dilution ranged from 1:50,000 to 1:1,000, 000 depending on the lot of antibody. The membrane was left in the antibody solution overnight at room temperature with rocking. The next morning, the membrane was washed a minimum of 3×10 minutes in 1× NET+0.5% gelatin and then 1×15 minutes in TBS (20 mM Tris pH 7.5, 500 mM NaCl). The protein bands bound by the anti-Fab antibody were visualized by using Amersham Pharmacia Biotech ECL detection and exposing the membrane to X-Ray film.

Some of the expressed protein bands were further subjected to N-terminal sequence analysis in which, following SDS-PAG electrophoresis, samples from induced cultures were electroblotted to a PVDF membrane (Matsudaira, J. Biol. Chem. 262:10035–10038 (1987)). Appropriate PVDF bands were sequenced on an Applied Biosystems (Foster City, Calif.) 494HT or 494cLC sequencer equipped with a 140C or 140D online PTH analyzer (Henzel et al., *Methods: A Companion to Methods Enzymol.* 6:239–247 (1994)).

Results

Polycistronic Vectors Produced Limited Quantities of Full Length Antibodies

Polycistronic plasmids for anti-TF antibody (pxTFPV) and anti-VEGF antibody (pY0317.Fab_CH3) were constructed, transformed into strain 33D3 and induced as described in Example 1 and above under Methods and Materials. Non-reduced whole cell lysate samples were then prepared and analyzed by western blot. The results are shown in FIG. 2. As the arrow indicates, a small amount of apparently full length, correctly folded antibody was observed for anti-TF antibody (Lane 2), and essentially no full length band was detected in the anti-VEGF antibody sample (Lane 3). Reduced samples were then prepared, separated by SDS-PAGE and transferred to a PVDF membrane. The induced protein bands for both anti-TF and anti-VEGF antibodies were then cut out and submitted for N-terminal amino acid analysis. The results revealed a mixture of processed mature protein and unprocessed precursor protein (in which the secretion signal sequence was not cleaved off) for both constructs. Thus, the polycistronic vectors pxTFPV and pY0317.Fab_CH3 failed to direct significant secretion and assembly of full length anti-TF or anti-VEGF antibodies.

To address the problem of inefficient secretion, additional polycistronic vectors were made with modulated TIR strength combinations for light and heavy chain, as illustrated in FIG. 3. The purpose of this experiment was to determine the translational levels that would achieve better secretion of light and heavy chains. The different combinations of TIR strengths could also be used to determine the preferred expression ratio of light to heavy chain for maximum accumulation of full length antibody. All of the constructs were designed and constructed according to the teachings in Example 1. The following constructs with various TIR strength combinations were constructed: paTF20 (1-light chain, 1-heavy chain), paTF30 (3-light, 1-heavy), paTF40 (1-light, 3-heavy), paTF90 (3-light, 3-heavy), paTF100 (3-light, 7-heavy, paTF110 (7-light, 3-heavy), paTF120 (7-light, 7-heavy). The numbers in the parenthesis represent the TIR relative strength for light or heavy chain, as described in Simmons et al., *Nature Biotechnol.* 14:629–634(1996), and in U.S. Pat. No. 5,840,523.

Western blot results of expression products using polycistronic vectors with various TIR strength combinations are shown in FIG. 4. 4A shows samples under reduced conditions in which the separated light and heavy chains. And 4B shows samples under non-reduced conditions in which the disulfide bonds remain intact. The reduced samples clearly show a large excess of light chain over heavy chain at all TIR strength combinations, even taken into consideration the fact that light chain is more readily detectable than heavy chain using this anti-Fab antibody (FIG. 4A). At the highest TIR strength combination (paTF120 (7-light, 7-heavy)), a small amount of unprocessed light chain starts to accumulate, indicating that secretion is being blocked. The non-reduced Western blot shows the accumulation of full length antibody along with several intermediate forms (FIG. 4B). The maximum level of full length antibody is achieved with paTF40 (1-light, 3-heavy) followed by paTF100 (3-light, 7-heavy). Both of these constructs have relatively lower ratios of light vs. heavy chain expression as shown in FIG. 4A, suggesting that the level of folded full length antibody is correlated to the relative expression levels of light and heavy chains.

Example 3

*E. coli* Expression of Full length Antibodies Using Separate Cistron Vectors

To construct the separate cistron vectors with modulated TIR strength combinations, a preferred TIR strength for secretion of each individual chain was first determined in a series of single cistron plasmids constructed to express light or heavy chain only (FIG. 5). A series of single cistron plasmids with various TIRs was therefore constructed for the individual expression of both anti-TF light and heavy chains. Methods and materials used for vector construction and protein expression were similar to those used for polycistronic vector expressions, which has been described in Examples 1 and 2 above.

The range of TIR strengths tested extended from a relative strength of 1 to a maximum relative strength of 13. Reduced whole cell lysates from induced cultures transformed with these constructed plasmids were analyzed by SDS-PAGE and the results are shown in FIG. 6. For both heavy and light chain, levels of secreted protein increase with increasing TIR up to a relative strength of 7. Then, in the case of heavy chain, the level of mature protein decreases when the TIR relative strength is raised to 13. When a TIR relative strength of 13 is used for light chain expression, the level of mature protein remains constant; however, precursor material begins to accumulate using this construct. This result suggested that for individual expression of light and heavy chain, the most preferred TIR is 7. The light and heavy chain protein bands produced using the TIR of 7 were confirmed by N-terminal amino acid analysis to be the completely processed mature form of the protein.

Once the most preferred TIR for each individual antibody chain was determined, the next step involved bringing together the two cistrons onto one plasmid. The two constructs with the TIR's of 7 were combined such that expression of each gene was maintained under the control of its own PhoA promoter (FIG. 7). Following transformation and induction, reduced whole cell lysate from this expression plasmid (pxTF2AP77) was prepared and analyzed by SDS-PAGE (FIG. 8). Four antibody-related bands were detected by Coomassie staining. These protein bands were subsequently determined by N-terminal amino acid analysis to be precursor and mature forms of both heavy and light chains. Therefore, although the preferred TIR strength may have been determined for each individual chain, when the two cistrons, maintained under the control of separate promoters, were combined onto a single construct, the simultaneous co-expression of both chains resulted in inefficient protein secretion. This result suggested that the most preferred TIR combination should be determined by simultaneously altering the individual TIRs for light and heavy chains in the context of a separate cistron construct.

A series of new constructs was prepared to determine the TIR strength combinations for light and heavy in the context of a separate cistron system. The TIR series shown in FIG. 9 parallels that of the polycistronic series and includes paTF50 (1-light, 1-heavy), paTF70 (3-light, 1-heavy), paTF60 (1-light, 3-heavy), paTF80 (3-light, 3-heavy), paTF130 (7-light, 3-heavy), paTF140 (3-light, 7-heavy), and pxTF2AP77 (7-light, 7-heavy). All expression inductions (2 mL) were carried out side-by-side in strain 33D3. Samples were removed for SDS-PAGE separation and the Western blot results are shown in FIG. 10. The reduced samples (FIG. 10A) show a more even distribution of light and heavy chains compared to the results from polycistronic vectors. A small level of light chain precursor accumulates with paTF80 (3-light, 3-heavy) and paTF140 (3-light, 7-heavy), while significant amounts of light and heavy chain precursor are obvious for paTF130 (7-light, 3-heavy) and pxTF2AP77 (7-light, 7-heavy). The non-reduced samples reveal various levels of full length antibody along with intermediate species (FIG. 10B). The greatest accumulation of full length antibody occurs with paTF50 (1-light, 1-heavy), and as the translation levels increase slowly up to paTF80 (3-light, 3-heavy), the levels of intermediate species rise dramatically. The two constructs with large amounts of unprocessed light and heavy chain (paTF130 and pxTF2AP77) show a sharp decrease in the levels of full length antibody as well as intermediate species. Therefore, the results suggested that for anti-TF full length antibody, the most preferred TIR combination is (1-light, 1-heavy), as represented by the plasmid paTF50.

Next, in order to further illustrate the high yield of full length antibody by the separate cistron system, expressions using the polycistronic constructs (paTF20 (1-light, 1-heavy), paTF30 (3-light, 1-heavy) and paTF40 (1-light, 3-heavy)) and the separate cistron constructs (paTF50 (1-heavy, 1-light), paTF60 (1-light, 3-heavy), paTF70 (3-light, 1-heavy) and paTF80 (3-light, 3-heavy)) were compared side by side. The non-reduced samples clearly show a much higher production level of full length antibody and intermediate species with the separate cistron system (FIG. 11). As shown on the gel, the best of the polycistronic constructs, paTF40 (1-light, 3-heavy), is still inferior to each of the separate cistron constructs shown.

A similar comparison between the pAK19-derived polycistronic plasmids and the separate cistron plasmids further illustrates the advantages of this new technology for the expression of full length antibodies in *E. coli*. The analysis included expression plasmids for both anti-tissue factor and anti-VEGF antibodies. With respect to the expression of anti-tissue factor, the polycistronic plasmid pxTFPV and the separate cistron plasmid paTF50 (1-light, 1-heavy) were transformed into strain 33D3 and induced in phosphate-limiting media. Non-reduced samples were prepared (IAA treated) and analyzed by Coomassie-stained SDS-PAGE (FIG. 12). An induced full length antibody protein band is observed from the separate cistron sample, using only Coomassie Blue stain as a method of detection (Lane 3). This protein band was subsequently determined by N-terminal amino acid analysis to contain both anti-tissue factor light and heavy chains, as expected. No such protein band is apparent by Coomassie staining using the polycistronic plasmid (Lane 2). The samples were also analyzed by western blot using a polyclonal goat anti-human Fab antibody (FIG. 13). Applying this sensitive method of detection, a small amount of full length antibody can be seen using the polycistronic plasmid (Lane 2); however, the expression level increases dramatically using the separate cistron plasmid (Lane 3).

A similar experiment comparing the expression of anti-VEGF antibody using a polycistronic vector (pY0317.Fab_CH3) and a separate cistron vector, pxVG2AP11 (1-light, 1-heavy), was also performed. The plasmids were transformed into strain 33D3 and induced in phosphate-limiting media. Non-reduced samples were prepared (IAA treated) and analyzed by Western Blot using a polyclonal goat anti-human Fab antibody (FIG. 14). Virtually no full length antibody is apparent using the polycistronic vector. Much of the sample appears as an indiscreet smear (Lane 2), a pattern which appears to correlate with a very high excess of light chain expression. In contrast, when the separate cistron system was used, a distinct full length antibody protein band is observed (arrow; Lane 3). Thus, for the expression of full length anti-VEGF, the separate cistron vector of the invention increases the expression level from essentially no detectable full length antibody to a level readily detectable by western blot.

Example 4

Large-scale Production (Fermentation) and Purification of Full Length Antibodies Expressed in *E. coli*

Full length anti-TF and anti-VEGF antibodies were also produced in large scale, using fermentation processes. The organisms used for these fermentations include: 59A7 W3110 ΔfhuA (ΔtonA) phoAΔE15 Δ(argF-lac)169 deoC degP41 kan$^S$ ilvG$^+$Δ prc::kanR prc suppressor; 43H1 W3110 ΔfhuA (ΔtonA) phoAΔE15 Δ(argF-lac)169 ptr3 degP41 kan$^S$ ΔompTΔ(nmpc-fepE) ilvG$^+$ prc::kanR prc suppressor; 33D3 W3110 ΔfhuA (ΔtonA) ptr3 lac Iq lacL8 ΔompTΔ (nmpc-fepE) degP41 kan$^R$; and 58H7 W3110 ΔfhuA (ΔtonA)Δ ptr3 ΔompT ΔdegP lac Iq ΔlacY.

For each 10-liter fermentation, 0.5 mL of frozen stock culture (containing 10–15% DMSO) was thawed and used to inoculate a 2 L shake flask containing 500 ml of LB medium supplemented with either 0.5 ml of tetracycline solution (5 mg/ml) or 10 mL of ampicillin solution (2 mg/mL) and 2.5 ml 1M sodium phosphate solution. This seed culture was grown for approximately 16 hours at 30° C. with shaking and was then used to inoculate the 10-liter fermentor.

The fermentor initially contained approximately 7.0 liters of medium containing 1.1 g of glucose, 100 ml of 1M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese sulfate monohydrate, in a final volume of 1 liter), either 20 ml of a tetracycline solution (5 mg/ml in ethanol) or 250 mL of an ampicillin solution (2 mg/mL), 1 bag of HCD salts, (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), 200 g of NZ Amine A (a protein hydrolysate), and 100 grams of Yeast Extract. Fermentations were performed at 30° C. with 20 slpm of air flow and were controlled at a pH of 7.0±0.2 (although occasional excursions beyond this range occurred in some cases). The back pressure of the fermentor was maintained at 1 bar gauge and the agitation rate was set to 650 rpm. The back pressure of the fermentor and agitation rate can also be varied to manipulate the oxygen transfer rate in the fermentor, and, consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Additions of L-61 (an antifoam—others can be used) were also used in some cases to control foaming. When the culture reached a cell density of approximately 40 OD550, an additional 100 ml of 1M magnesium sulfate was added to the fermentor. Additionally, a concentrated salt feed (12.5 g ammonium sulfate, 32.5 g potassium phosphate dibasic, 16.25 g sodium phosphate monobasic dihydrate, 2.5 g sodium citrate dihydrate, 18.75 g potassium phosphate monobasic, 10 ml of 2.7% ferric chloride and 10 ml of trace elements in a final volume of 1250 ml) was added to the fermentor and started at a rate of 2.5 ml/min when the culture reached approximately 20 OD550 and continued until approximately 1250 ml were added to the fermentation. Fermentations were typically continued for 70–80 hours. During the fermentation, once the dissolved oxygen set point for the fermentation was reached, the concentrated glucose solution was fed based on the dissolved oxygen probe signal in order to control the dissolved oxygen concentration at the set point. Consequently, in this control scheme, manipulations of fermentor operating parameters such as the agitation rate or back pressure which affect the oxygen transfer capacity in the fermentation correspondingly also manipulated the oxygen uptake rate or metabolic rate of the cells. A mass spectrometer was used to monitor the composition of the off-gas from the fermentations and enable the calculation of the oxygen uptake and carbon dioxide evolution rates in the fermentations.

Non-reduced soluble samples were prepared as follows: frozen, 1 mL whole broth samples taken during the course of the fermentation were thawed at room temperature. 100 μL of the thawed whole broth was added to 500 μL of extraction buffer. (Extraction buffer: 10 mM Tris, pH 6.8, 5 mM EDTA, freshly added 0.2 mg/mL of hen egg lysozyme, and freshly prepared iodacetic acid to a final concentration of 5–10 mM.) The whole broth samples plus extraction buffer were incubated on ice for 5–10 minutes, then sonicated 2×10 pulses, then centrifuged at 4C and 14,000 rpm for 15–20 minutes. The supernatant was removed as the soluble fraction. For analysis by SDS-PAGE and immunoblots, the soluble fraction was diluted 1:4 into 2× Novex Tricine sample buffer without reducing agent. 10 μL of this prep was loaded onto a 15 well Novex 4–12% Bis-Tris NuPage gel and electrophoresed at 200 V with MOPS buffer. The gel was then used for either an immunoblot or stained with Coomassie Blue.

Samples of the soluble fractions were submitted for analysis by an AME5-RP assay. This assay is a dual column HPLC assay where the first column is an affinity column that captures light chain and the second column is a reversed-phase column. An Integral Workstation was configured in the dual column mode. The solvent reservoirs were: Solvent 1A, affinity loading buffer; Solvent 1B, reversed-phase aqueous buffer and affinity elution buffer, 0.1% TFA in water; Solvent 2A, water; Solvent 2B, reversed-phase organic elution buffer, 0.09% TFA/80% acetonitrile. The first column was the affinity column (30×2.1 mm) containing an immobilized anti-light-chain (kappa) Fab antibody (AME5) immobilized on controlled pore glass. All procedures involving the affinity column were performed at ambient temperature. The second column was the reversed-phase column containing the polymer based POROS R220 packing material (30×2.1 mm). The reversed-phase column temperature was maintained at 60° C.

The affinity column was equilibrated in 30% loading buffer (5 ml) and a 50 µl sample was loaded at a flow rate of 0.1 ml/min. The flow-through was directed to waste. After the sample was loaded the affinity column was washed with 30% loading buffer (2 ml), followed by 100% loading buffer (5 ml) to reduce non-specifically bound components. A final wash with water prepared the affinity column for elution (3 ml). The affinity column was now connected to the reversed-phase column (by valve switching) and eluted with elution buffer (2 ml) at a flow rate of 2 ml/min to transfer the affinity captured components to the reversed phase column. During this transfer step the Integral UV detector is located after the affinity column and before the reversed-phase column and hence monitors the elution of the affinity column (which becomes the load to the reversed-phase column). In addition to this detector, a second detector was added after the reversed-phase column to monitor its flow-through to confirm that all the components eluted from the affinity column were in fact captured by the reversed-phase column.

Re-equilibration of the affinity column was subsequently performed with loading buffer (4 ml) after removing its connection to the reversed-phase column.

The loaded reversed-phase column was washed with aqueous 0.1% TFA (2 ml). The flow rate was set to 1 ml/min and a rapid gradient (1 min) was run to 35% solvent 2B (0.1% TFA/80% acetonitrile) followed by a shallow gradient to 50% solvent 2B over 14 min. Elution is completed by a gradient to 90% solvent 2B over 4 min. The reversed phase column was then returned to initial conditions over 1 min. and re-equilibrated for 3 min at 2 ml/min. The column eluate was monitored at 280 and 214 nm. Quantitation was performed by comparison of the integrated peak areas with those of standards of known concentrations.

Fractions were collected across the gradient profile, pooled as appropriate and lyophilized. Peak fractions were partially characterized using the usual procedures employed in N-terminal sequence analysis, and SDS-PAGE analysis. They were also analyzed by liquid chromatography/mass spectrometry (LC/MS). N-terminal sequence analysis, LC/MS, and SDS-PAGE revealed that Peak 5 on the chromatogram contained predominantly full-length antibodies in tetrameric form (i.e., two light chains and two heavy chains).

Production of full-length anti-TF antibodies using the polycistronic plasmid paTF20 (1-light, 1-heavy) or paTF40 (1-light, 3-heavy) was compared to that using the separate cistron vector paTF50 (1-light, 1-heavy), in the 43H1 *E. coli* strain. Fermentations have also been conducted in 33D3 and 59A7 strains transformed with the paTF50 plasmid. Analysis of fermentation samples by the AME5-RP assay gave the following AME5-RP assay Peak 5 titers shown in Table 2:

TABLE 2

| anti-TF Plasmid | *E. coli* Host | AME5-RP Peak 5 (mg/L) |
|---|---|---|
| paTF20 | 43H1 | 13 |
| paTF40 | 43H1 | 18 |
| paTF50 | 43H1 | 134 |
| paTF50 | 33D3 | 115 |
| paTF50 | 59A7 | 156 |

Thus, as the AME5-RP results indicated, the separate cistron vector paTF50 produces significantly higher yields of intact anti-TF antibodies, compared to polycistronic vectors.

Fermentation products were purified as follows: bacteria cell paste was diluted 1:5 (w/v) in 20 mM sodium phosphate pH 7.4, 0.14 M NaCl, then lysed using an M110Y microfluidizer (Microfluidics Corp., Newton, Mass.). The solution containing lysed cells was clarified by centrifugation (4300× g, 30 min) to remove cellular debris. Polyethylene imine (BASF Corp., Rensselaer, N.Y.) was added to the supernatant to a final concentration of 0.2%, followed by centrifugation (4300×g, 30 min). The supernatant was filtered (0.2 µm) and applied to a Protein A affinity resin, Prosep A (Millipore Corp., Bedford, Mass.). The *E. coli* derived $IgG_1$ was eluted using 0.1 M acetic acid pH 2.9. The Protein A pool was conditioned by the addition of urea to a final concentration of 2M, adjusted to pH 5.5, then diluted with purified water and applied to SP Sepharose FF (Amersham Pharmacia Biotech, Uppsala, Sweden). The SP Sepharose FF column was washed with 20 mM MES pH 5.5, followed by $IgG_1$ elution using a linear gradient from 0 to 0.25 M NaCl in 20 mM MES pH 5.5. SP Sepharose FF gradient fractions were analyzed by SDS-PAGE and pooled. The SP Sepharose FF pool was adjusted to pH 8.0 and applied to Q Sepharose FF (Amersham Pharmacia Biotech, Uppsala, Sweden). The Q Sepharose FF column was washed with 25 mM Tris pH 8.0, 50 mM NaCl, followed by $IgG_1$ elution using 25 mM Tris pH 8.0, 150 mM NaCl. The Q Sepharose FF pool was formulated by ultrafiltration using a 10 kDa regenerated cellulose membrane (Millipore Corp., Bedford, Mass.), followed by diafiltration into 20 mM sodium acetate pH 5.5, 0.14 M NaCl.

Example 5

Characterization of Full Length Antibodies Produced in *E. coli*

To further confirm that the full length antibodies produced in the *E. coli* host cells of the present invention possess desired properties, the anti-TF antibody products prepared by fermentation and purified according to the procedures of Example 4 were further characterized by a series of assays including Mass Spectrometry, Ion-Exchange Chromatography, Size-Exclusion Chromatography, Amino Acid Analysis and N-terminal Sequencing.

MALDI-TOF-MS Analysis:

MALDI-TOF-MS was performed on a Voyager DE Biospectrometry WorkStation (Perseptive Biosystems, Framingham, Mass.) equipped with delayed extraction. A nitrogen laser was used to irradiate samples with ultraviolet light (337 nm) and an average of 240 scans was taken. The instrument was operated in linear configuration (1.2 m flight path), and an acceleration voltage of 20 kV was used to propel ions down the flight tube after a 60 ns delay. Samples (1.0 ul) were mixed with 1 ul of matrix and 1 ul of this mixture was added to the target and dried under vacuum (50×10−3 Torr). Protein standards were used to achieve a two point external calibration for mass assignment of ions. 4-Hydroxycinnamic acid matrix was used in the analysis of the full length anti-TF antibodies.

Ion-Exchange Chromatography:

Cation-exchange chromatography was carried out on a HP1100 instrument using Baker Bond CSX column (4.6× 250 mm). The column was equilibrated for 20 min with buffer A (25 mM sodium acetate, pH 4.8) at 1 ml/min flow rate. The samples were diluted to —approximately 1 mg/ml in buffer A and injected—approximately 50 ug. The column temperature was maintained at 40° C. A linear gradient was applied over 40 min to 60% buffer B (buffer A+500 mM NaCl) and held at 60% buffer B for 5 min. The column effluent was monitored at 280 nm.

Size Exclusion Chromatography:

A TSK G3000SW-XL column (7.8×300 mM; TosoHaas) was used for size exclusion chromatography on a HP1100 instrument. The column was equilibrated with 100 mM potassium phosphate buffer pH 6.3 containing 250 mM sodium chloride at flow rate of 0.5 ml/min. Samples were diluted to 1 mg/ml with the elution buffer and —approximately 100 ug was injected to the column. The run time was 30 min. Samples of gel filtration standards (Bio-Rad) were also injected after five-fold dilution with the elution buffer.

Amino-Terminal Sequence Analysis:

The sample was exchanged into 0.1% acetic acid by dialysis. An aliquot containing 83 ug was loaded for N-terminal sequence analysis by the Edman degradation method using an Applied Biosystems 477A/120A automated protein sequencer. Peak height comparison to an external standard was used to quantitate PTH-amino acids.

Amino Acid Analysis:

Aliquots containing 15 ug of desalted samples were dried in hydrolysis ampoules by evaporation in a Savant Speed-Vac. After addition of 6 N HCl (Pierce), the ampoules were sealed under reduced pressure and incubated for 24 or 72 hours at 110° C. Additional aliquots were subjected to performic acid oxidation by incubation for four hours at 0–5° C. with a solution prepared an hour earlier containing 10% hydrogen peroxide and 90% formic acid. The performic acid was subsequently removed by evaporation in a Savant SpeedVac, after which the samples were subjected to 24-hour hydrolysis in 6 N HCl as described above. For Trp determinations, triplicate aliquots containing 25 ug of each lot were dried in ampoules and incubated at 110° C. for 24 hours under a nitrogen atmosphere in a 7% mercaptoacetic acid (Baker)/93% 6 N HCl (Pierce) solution under reduced pressure. After hydrolysis, all samples were dried by evaporation in a Savant SpeedVac.

Hydrolysates were reconstituted in a 0.2 N sodium citrate buffer, pH 2.2 (Beckman) and subjected to amino acid analysis using a Beckman 6300 cation exchange instrument with post-column ninhydrin detection. The signal representing the sum of the absorbance at 440 nm and 570 nm was monitored by a PE Nelson Turbochrom 4 data system. Amino acid quantitation was achieved by peak area or peak height comparisons to external standard mixtures containing 1 or 2 mmol of each component.

The results obtained from various assays described above confirmed that the full length anti-TF antibodies produced in E. coli using the expression vectors of the present invention share similar structural characteristics to those anti-TF antibodies produced in eukaryotic host cells, such as CHO cells.

Example 6

Functional Analysis of the Full Length Antibodies Produced in E. coli

The antibodies produced and purified from E. coli according to the previous examples are full length and aglycosylated. The following experiments were performed to illustrate that the antibodies: 1) exhibit tight bivalent antigen binding ability; 2) lack C1q binding ability and therefore the CDC function is depleted; 3) lack FcγR1 binding ability and therefore the ADCC functions are depleted; and 4) show strong FcRn binding, for improved resistance to clearance therefore promoting a longer half life in vivo.

TF Antigen Binding

The full length anti-TF antibodies were evaluated for antigen binding using an ELISA assay. MaxiSorp 96-well microwell plates (Nunc, Roskilde, Denmark) were coated with 1 µg/ml soluble tissue factor (TF) comprising residues 1–219 (Genentech) in 50 mM carbonate buffer, pH 9.6, at 4° C. overnight. Plates were blocked with PBS, 0.5% bovine serum albumin, 10 ppm Proclin 300 (Supelco, Bellefonte, Pa.), pH 7.2, at room temperature for 1 hour. Threefold serial dilutions of antibodies (0.27–200 ng/ml) in PBS, 0.5% bovine serum albumin, 0.05% polysorbate 20, 0.25% CHAPS, 0.2% bovine γ globulins (Sigma, St Louis, Mo.), pH 7.2 (assay buffer) were added to the plates and plates were incubated for 2 hours. Bound IgG was detected by adding peroxidase conjugated goat anti-human F(ab')$_2$ antibody (Jackson ImmunoResearch, West Grove, Pa.) in assay buffer, incubating the plates for 1 hour and adding 3,3',5,5'-tetramethyl benzidine (Kirkegaard & Perry Laboratories, Gaithersburg, Md.) as the substrate. Plates were washed between steps with PBS, 0.05% polysorbate 20, pH 7.2. Absorbance was read at 450 nm on a Titerek stacker reader (ICN, Costa Mesa, Calif.). Titration curves were fitted using a four-parameter nonlinear regression curve-fitting program (KaleidaGraph, Synergy software, Reading, Pa.).

The results of the TF antigen binding ELISA assay are shown in FIG. 15. The full length anti-TF antibodies made in E. coli (IgG1) are compared with anti-TF antibodies of different isotypes that were made in CHO cells. The E. coli made IgG1 antibody shows antigen binding activities that are at least comparable to the other anti-TF antibodies made in CHO cell systems.

C1q Binding

The binding of human C1q to purified E. coli produced anti-TF antibody was determined using an ELISA binding assay as described in Idusogie et al. (2000) J. Immuno 164:4178–4184. Briefly, Costar 96 well plates were coated overnight at 4° C. with various concentrations of antibodies in coating buffer (0.05 M sodium carbonate buffer), pH 9. The plates were then washed 3× with PBS/0.05% TWEEN 20™, pH 7.4 and blocked with 200 µl of ELISA diluent without thimerosal (0.1M NaPO4/0.1M NaCl/0.1% gelatin/ 0.05% TWEEN 20™/0.05% ProClin300) for 1 hr at room temperature. The plate was washed 3× with wash buffer, an aliquot of 100 µl of 2 µg/ml C1q (Quidel, San Diego, Calif.) was added to each well and incubated for 2 hrs at room temperature. The plate was then washed 6× with wash buffer. 100 µl of a 1:1000 dilution of sheep anti-human C1q peroxidase conjugated antibody (Biodesign) was added to each well and incubated for 1 hour at room temperature. The plate was again washed 6× with wash buffer and 100 µl of substrate buffer (PBS/0.012% H$_2$O$_2$) containing OPD (O-phenylenediamine dihydrochloride (Sigma)) was added to each well. The oxidation reaction, observed by the appearance of a yellow color, was allowed to proceed for 30 minutes and stopped by the addition of 100 μl of 4.5 N H$_2$SO$_4$. The absorbance was then read at (492–405) nm using a microplate reader (SPECTRA MAX 250™, Molecular Devices Corp.). The appropriate controls were run in parallel (i.e. the ELISA was performed without C1q for each concentration of the antibodies used and also the ELISA was performed without the antibody). For each sample, C1q binding was measured by plotting the absorbance (492–405) nm versus concentration in μg/ml, using a 4-parameter curve fitting program (KALEIDAGRAPH™) and comparing EC$_{50}$ values. The results of this assay are depicted in FIG. 16. A CHO cell-expressed antibody, I-1095-1-Rituximab, was used as a positive control. No C1q binding was detected from the E. coli made full length anti-TF antibody, even at high antibody concentrations.

Fc γ Receptor Binding

The binding of FcγR1 to purified anti-TF antibody was determined using the following ELISA binding assay. FcγR1 α subunit-GST fusion was coated onto Nunc F96 maxisorb plates (cat. no. 439454) by adding 100 ul of receptor-GST fusion at 1 ug/ml in PBS and incubated for 48 hours at 4° C. Prior to assay, plates were washed 3× with 250 ul of wash buffer (PBS pH 7.4 containing 0.5% TWEEN 20) and blocked with 250 ul of assay buffer (50 mM Tris buffered saline, 0.05% TWEEN 20, 0.5% RIA grade bovine albumin (Sigma A7888), and 2 mM EDTA pH 7.4). Samples diluted to 10 ug/ml in 1 ml of assay buffer were added to FcγR1 α subunit coated plates and incubated for 120 minutes at 25° C. on an orbital shaker. Plates were washed 5× with wash buffer to remove unbound complexes and IgG binding was detected by adding 100 ul horse radish peroxidase (HRP) conjugated goat anti-human IgG γ heavy chain specific (Boehringer Mannheim 1814249) at 1:10,000 in assay buffer and incubated for 90 min at 25° C. on an orbital shaker. Plates were washed 5× with wash buffer to remove unbound HRP goat anti-human IgG and bound anti-IgG was detected by adding 100 ul of substrate solution (0.4 mg/ml o-phenylenedaimine dihydrochloride, Sigma P6912, 6 mM H$_2$O$_2$ in PBS) and incubating for 8 min at 25° C. Enzymatic reaction was stopped by the addition of 100 ul 4.5 N H$_2$SO$_4$ and calorimetric product was measured at 490 nm on a 96 well plate densitometer (Molecular Devices). The results of this assay are depicted in FIG. 17. The positive controls, mammalian 293 expressed antibodies, bind to the receptor but no FcγR1 binding is detected for the E. coli produced anti-TF antibody.

FcRn Binding

The binding of purified anti-TF antibodies to FcRn was analyzed using the following ELISA binding assay. ELISA plates were coated with soluble tissue factor and blocked as described above. Two fold serial dilutions of anti-TF antibodies (1.6–200 ng/ml) in PBS, 0.5% bovine serum albumin, 0.05% polysorbate 20, pH 6.0 (sample buffer) were added to the plates and plates were incubated for two hours at room temperature. Biotinylated FcRn (prepared using biotin-X-NHS from Research Organics, Cleveland, Ohio) at 3.6 μg/ml in sample buffer was added to the plates. After a 1 hour incubation, bound FcRn was detected by adding streptavidin labeled peroxidase (Amdex, Copenhagen, Denmark) in sample buffer, incubating the plates for 1 hour and adding 3,3',5,5'-tetramethyl benzidine (Kirkegaard & Perry Laboratories) as the substrate. Plates were washed between steps with PBS, 0.5% BSA, 0.05% polysorbate 20, pH 6.0. Absorbance was read at 450 nm on a Thermo$_{max}$ plate reader (Molecular Devices, Menlo Park, Calif.). Titration curves were fit as described above. FIG. 18 shows that the FcRn binding activity of the E. coli made full length anti-TF antibody is comparable to other anti-TF antibodies (IgG4, IgG4b, IgG2) made in mammalian host cells.

Example 7

Pharmacokinetics Study of the Full Length α-TF Antibodies Made in E. coli

The E. coli made full length anti-TF antibody (IgG1 E. coli) was subject to a single IV bolus dose chimpanzee pharmacokinetic (PK) study, along with two other anti-TF antibodies made in CHO cells (IgG2 CHO and IgG4b CHO) as controls. Three chimpanzees were tested negative for the presence of anti-TF antibodies. Each animal received a single IV bolus dose of anti-TF antibody (IgG1 E. coli, IgG2 CHO or IgG4 CHO) at 0.10 mg/kg. Plasma samples were collected up to 28 days post dosing according to the following schedule: 30 and 15 minutes predose; 2, 15, 30 minutes; 1, 2, 3, 4, 6, 12 hours; 1, 2, 4, 7, 14, 21, and 28 days post IV bolus dose. Plasma samples were assayed for anti-TF antibody (ATF) content by ELISA, using TF as a coat and an anti-Fc monoclonal antibody as a detecting antibody. The limit of quantification was 0.102 μg/ml in chimpanzee plasma.

The ELISA results is shown in FIG. 19 in the form of plasma ATF concentration versus time curves. The data were fit to a one-compartment elimination profile in Win Nonlin 3.0. The PK parameter estimates of Clearance (CL), elimination half-life (T$_{1/2}$) and Volume (V) are reported in Table 3. Based on this experiment in three individual chimpanzees, no obvious differences in PK parameter estimates were observed between the antibody made in E. coli and those made in CHO cells.

TABLE 3

| Chimp Number | 202 | 336 | 569 |
|---|---|---|---|
| Antibody | IgG1 E. coli | IgG4b CHO | IgG2 CHO |
| CL (ml/day/kg) | 36.3 | 44.6 | 91.8 |
| T$_{1/2}$ (day) | 0.938 | 0.926 | 0.694 |
| V (ml/kg) | 49.2 | 59.6 | 92.0 |

Example 8

Expression and Fermentation of Various Full Length Antibodies Using Separate Cistron Vectors Separate cistron vectors were also constructed for the expression of the following full length antibodies: anti-VEGF (VNERK), a higher affinity variant of the humanized antibody described in Presta et al., Cancer Res. 57:4593–4599 (1997); a humanized anti-IgE antibody described in Presta et al., J. Immunol. 151:2623–2632 (1993); anti-CD40, a humanized version of the anti-CD40 antibody described in Francisco et al., Cancer Res. 60:3225–3231 (2000); anti-HER-2 (versions 4D5 and 2C4; Carter et al., Proc. Natl. Acad. Sci. USA 89:4285–4289 (1992) and Fendly et al., Cancer Res. 50:1550–1558 (1990); and a humanized anti-CD18 (Eigenbrot et al., Proteins: Structure, Function, and Genetics 18:49–62 (1994)).

For the construction of separate cistron plasmids, the V$_L$ and V$_H$ regions of paTF50 (TIR1-light, TIR1-heavy; see Example 1) were replaced with the V$_L$ and V$_H$ of each of the listed antibodies. Expression induction was carried out in strain 33D3, as described in Example 3. Samples were removed for SDS-PAGE separation and immunoblot under non-reducing conditions. As shown in FIG. 22, full length versions of antibodies anti-VEGF, anti-IgE, anti-CD40, 4D5, 2C4 and anti-CD18 were successfully expressed in *E. coli* using separate cistron vectors. This data illustrates that the separate cistron expression system is a generally applicable approach for antibody expression in *E. coli*.

To further illustrate the utility of the separate cistron expression system described herein, the above-described plasmids expressing various listed antibodies were used in large-scale productions (fermentation processes).

The organisms used for these fermentations include: 33D3 W3110 ΔfhuA (ΔtonA) ptr3 lac Iq lacL8 ΔompTΔ (nmpc-fepE) degP41 kan$^R$; 61D6 W3110 ΔfhuA (ΔtonA) ptr3 lac Iq lacL8 ΔompTΔ(nmpc-fepE) degP41; and 62A7 W3110 ΔfhuA (ΔtonA) ptr3 lac Iq lacL8 ΔompTΔ(nmpc-fepE) degP41 ilvG repaired.

Fermentations of the listed antibodies were done at the 10-liter scale and soluble samples prepared and submitted to the AME5-RP assay as described in Example 4. The AME5-RP assay titers of peak 5 containing full length antibodies predominantly in tetrameric form (two L chains and two H chains), are shown in Table 4.

TABLE 4

| Antibody | *E. coli* host | AME5-RP Peak 5, mg/L |
| --- | --- | --- |
| anti-TF | 61D6 | 112 |
| anti-CD18 | 61D6 | 34 |
| anti-IgE (E25 variant) | 33D3 | 77 |
| anti-VEGF (VNERK variant) | 61D6 | 53 |
| anti-CD40 | 62A7 | 45 |
| anti-Her2 (4D5 variant) | 62A7 | 55 |
| anti-Her2 (2C4 variant) | 62A7 | 73 |

Example 9

Co-Expression of Dsb Proteins and Full Length Antibodies in *E. coli*

Using the separate cistron system of the invention, full length anti-TF antibodies were also co-expressed with one or more Dsb proteins that are capable of facilitating the proper folding and assembly of the antibodies.

The organisms used for these fermentations include: 58H7 W3110 ΔfhuA (ΔtonA) Δ ptr3 ΔompT ΔdegP lac Iq ΔlacY; and 61D6 W3110 ΔfhuA (ΔtonA) ptr3 lac Iq lacL8 ΔompTΔ(nmpc-fepE) degP41.

anti-TF encoding plasmid paTF50 or pxTF2AP22 (a paTF50 variant with TIRs of 2 for both light chain and heavy chain) was used to transform competent cells of the above organisms. Plasmids encoding either dsbC (pJJ141), dsbA (pJJ142), or dsbA/C (pJJ247) were co-transformed with the anti-TF plasmid paTF50 or pxTF2AP22.

To construct the dsbC plasmid pJJ141, the kanamycin resistant plasmid pACYC177 was digested with AatII and HincII disrupting ampicillin resistance. The tac-dsbC plasmid pJJ40, described in U.S. Pat. No. 5,639,635, was digested with ClaI and then filled in with Klenow and deoxynucleotides. After phenol:chloroform extraction and precipitation, the linearized vector was digested with AatII and the 1.6 kb fragment was purified from an agarose gel and ligated to AatII/HincII digested pACYC177. The final plasmid pJJ141 encodes tac-dsbC and confers kanamycin resistance. Similarly, the dsbA plasmid pJJ142 was constructed using the same AatII/HincII cut parent vector ligated with a AatII/ClaI (filled in ClaI site) fragment from pJJ37, which encodes dsbA and is also described in U.S. Pat. No. 5,639,635.

To construct pJJ247, the plasmid encoding both dsbA and dsbC, pJJ142 was digested with KpnI and ScaI. DsbC was PCR amplified from plasmid pJJ141 using the following primers:

```
tacdsbCf1:
CATACTGGTACCAGGATCTAGAGGGAAGATTTATG   (SEQ ID NO:3)

tacdsbCr2:
CTGGTGAGTACTCAACCAAGTCATTCTG          (SEQ ID NO:4)
```

The primers contain restriction sites (KpnI, ScaI) which are underlined. After PCR amplification, the fragment was purified by agarose gel electrophoresis and digested with the appropriate enzymes and ligated to KpnI/ScaI digested pJJ142. The resulting plasmid, pJJ247, encodes a tac promoter driving the expression of both dsbA and dsbC with dsbA first in the series. The plasmid was sequenced from the middle of the dsbA gene through the 3' end of the dsbC gene.

In some cases, single plasmids encoding both anti-TF with a TIR of 1 for both light chain and heavy chain and either DsbC (pJJ241) or DsbA (pJJ237) were constructed to transform competent host cells.

To construct the plasmid pJJ237 which co-expresses anti-TF and dsbA, the anti-TF plasmid pATF50 was digested with AatII and HpaI and ligated to a AatII/HpaI cut fragment from pJJ223. This latter fragment contains araC, the pBAD promoter, dsbA, kanamycin resistance, a colE1 origin of replication, and the β-lactamase gene. The product of the ligation contains: both L and H chains of anti-TF under separate phoA promoters, an arabinose inducible promoter (pBAD) driving expression of dsbA with the plasmid conferring kanamycin and ampicillin resistance. This plasmid was termed pJG9. To make pJJ237, the arabinose regulon was changed to the tac promoter by PCR amplification. To do this, the following primers were used:

```
dsbAf11:
TGCACGGTTAACATGCTGTGGTGTCATGGTCGG     (SEQ ID NO:5)

dsbAr12:
TTTACCGTTAACAAACATCGCCGGAAC           (SEQ ID NO:6)
```

The underlined sites are HpaI sites. After amplification using pJJ142 as the template (contains tac-dsbA), the fragment was gel purified and digested with HpaI. The pJG9 vector was digested with HpaI and NaeI removing the araC-pBAD-dsbA region. The HpaI-NaeI cut vector was gel purified and ligated to the tac-dsbA HpaI cut PCR fragment. The resulting plasmid, termed pJJ237, contains the separate phoA promoters driving expression of αTF L and H chains and the tac promoter driving dsbA expression.

To construct plasmid pJJ241 which co-expresses anti-TF and dsbC, pJG9 was digested with HpaI and NgoMIV. NgoMIV cuts at the same site as NaeI but leaves a sticky end instead. DsbC was PCR amplified from pJJ141 as the template with the same forward primer as dsbA (dsbAf11; SEQ ID NO:5) and the reverse primer as follows:

dsbCr12: TCAGCTGCCGGCGTCCGATGCGAATTATTTACCG (SEQ ID NO:7)

The underlined site is a NgoMIV site. The amplified fragment was gel purified and digested with NgoMIV and HpaI and ligated to pJG9. The resulting plasmid contains the separate phoA promoters driving expression of anti-TF L and H chains and the tac promoter driving dsbC expression.

When a plasmid encoding anti-TF and a plasmid encoding one or more Dsb proteins were used together to transform the competent cells, transformants were plated on LB agar plates containing 50 µg/mL of both carbenicillin and kanamycin. In those cases where a single plasmid expressing both anti-TF and the selected Dsb proteins (dsbA or dsbC), tranformants were selected on LB agar plates containing 50 µg/mL of kanamycin.

Fermentations were done at the 10-liter scale as described in Example 4, with the addition of 50 mL of a 200 mM solution of isopropyl β-D-thiogalactopyranoside (IPTG) to the fermentation culture when the OD550 reached 150–200. IPTG additions can be made at times other than the one described and different amounts of IPTG than described can be also added. Soluble samples were prepared and submitted to the AME5-RP assay as described in Example 4. The various plasmid/host strains and resulting titers of peak 5 are summarized in Table 5.

TABLE 5

| anti-TF Plasmid | E. coli Host | Dsb Plasmid | AME5-RP Peak 5 (mg/L) |
| --- | --- | --- | --- |
| paTF50 | 58H7 | none | 100 |
| paTF50 | 61D6 | none | 127 |
| paTF50 | 58H7 | pJJ141 | 174 |
| pJJ241 | 58H7 | pJJ241 | 212 |
| paTF50 | 58H7 | pJJ142 | 125 |
| pJJ237 | 58H7 | pJJ237 | 135 |
| paTF50 | 61D6 | pJJ247 | 584 |
| pxTF2AP22 | 61D6 | none | 118 |
| pxTF2AP22 | 58H7 | pJJ141 | 349 |
| pxTF2AP22 | 58H7 | pJJ142 | 134 |
| pxTF2AP22 | 61D6 | pJJ247 | 881 |

Example 10

Co-Expression of FkpA and Full Length Antibodies in E. coli

Full length anti-TF antibodies were also co-expressed with FkpA, a peptidylprolyl cis,trans-isomerase with chaperone activity.

The organisms used for these fermentations include: 58H7 (genotype W3110 ΔfhuA (ΔtonA) Δ ptr3 ΔompT ΔdegP lac Iq ΔlacY); and 59A7 (genotype W3110 ΔfhuA (ΔtonA) phoAΔE15 Δ(argF-lac)169 deoC degP41 kan$^s$ ilvG$^+$Δ prc::kanR prc suppressor).

A separate plasmid encoding fkpA under the control of the tacII promoter (pJVG2) was co-transformed with anti-TF plasmid paTF50. To create pJVG2, plasmid pJJ222fkpA was digested with NheI and NgoMIV to create a 0.8 kb fragment containing fkpA. This fragment was purified by electrophoresis and phenol:chloroform extraction and precipitation. Plasmid pJJ239 which contains tac-DsbD on a pACYC177 vector analogous to pJJ142, was digested with XbaI and NgoMIV to create a 3.9 kb fragment containing an inducible tac promoter and kanamycin resistance. This fragment was purified by electrophoresis and phenol:chloroform extraction and precipitation. These two fragments were ligated creating pJVG2 containing an inducible tac promoter, fkpA and kanamycin resistance. This plasmid is similar to pJJ141 and pJJ142 in that it's a compatible pACYC177 plasmid that can be used to co-express fkpA with pBR322 based plasmids.

In addition, a single plasmid encoding both anti-TF chains under the control of separate phoA promoters and fkpA under the control of the arabinose promoter (pJG9fkpAB3) was used to transform competent cells of the above organisms. To create pJG9fkpAB3, plasmid pJJ222fkpA was digested with HpaI and NdeI to create a 4.1 kb fragment containing araC, the inducible promoter pBAD, fkpA and kanamycin resistance. FkpA had been originally PCR amplified from the E. coli chromosome and cloned behind the pBAD promoter in commericially available pBAD18. The fragment was purified by electrophoresis and phenol:chloroform extraction and precipitation. Plasmid pJG9 was digested with HpaI and NdeI to create a 5.1 kb fragment containing ampicillin resistance, the separate cistrons for both L and H chains of αTF antibody. It was purified by electrophoresis and phenol:chloroform extraction and precipitation. The two fragments were ligated to create pJG9fkpAB3, which contains separate promoters driving expression of anti-TF antibody chains, araC, the pBAD promoter driving expression of only fkpA, kanamycin resistance, a colE1 origin of replication, and ampicillin resistance.

When the anti-Tissue Factor plasmid paTF50 and the fkpA plasmid pJVG2 were used together to transform the competent cells, transformants were plated on LB agar plates containing 50 µg/mL of both carbenicillin and kanamycin. When cells were transformed with the single plasmid pJG9fkpAB3, tranformants were selected on LB agar plates containing 50 µg/mL of kanamycin.

Fermentations were done at the 10-liter scale as described in Example 4 with the following modifications. Fermentations using the cells transformed with the plasmid pJG9fkpAB3 had an addition of 200 mL of a 40% arabinose solution at approximately an OD550 of 150–200. Prior to the arabinose addition, the glucose feed rate was cut such that the culture became glucose limited. After the arabinose addition and consumption, the glucose feed rate was resumed to allow maximum glucose uptake by the culture. Fermentations using the cells co-transformed with the plasmids paTF50 and pJVG2 had an addition of 50 mL of a 200 mM solution of isopropyl P-D-thiogalactopyranoside (IPTG) to the fermentation culture when the OD550 reached 150–200. IPTG additions can be made at times other than the one described and different amounts of IPTG than described can be also added. Soluble samples were prepared and submitted to the AME5-RP assay as described in Example 4.

The fermentation with the 59A7 host transformed with paTF50 gave an AME5-RP Peak 5 titer of approximately 156 mg/L, compared to 247 mg/L for the 59A7 host transformed with the pJG9fkpAB3 plasmid. Likewise, the fermentation with the 58H7 host transformed with the plasmid paTF50 gave an AME5-RP Peak 5 titer of approximately 100 mg/L compared to 180 mg/L for the 58H7 host co-transformed with paTF50 and pJVG2.

Although the forgoing refers to particular embodiments, it will be understood that the present invention is not so limited. It will occur to those ordinary skilled in the art that various modifications may be made to the disclosed embodiments without diverting from the overall concept of the invention. All such modifications are intended to be within the scope of the present invention.

What is claimed is:

1. A polynucleotide molecule encoding an intact antibody, said polynucleotide molecule comprising (1) a first promoter and a first cistron forming a first promoter-cistron pair and (2) a second promoter and a second cistron forming a second promoter-cistron pair, wherein the first cistron of said first promoter-cistron pair comprises a first translational initiation region (TIR-L) operably linked to a nucleic acid sequence encoding an immunoglobulin light chain and the second cistron of said second promoter-cistron pair comprises a second translational initiation region (TIR-H) operably linked to a nucleic acid sequence encoding an immunoglobulin heavy chain, wherein upon expression of said polynucleotide in a prokaryotic host cell, secreted light and heavy chains are folded and assembled to form a biologically active intact antibody.

2. The polynucleotide molecule of claim 1, wherein the first and second promoters are prokaryotic promoters selected from the group consisting of phoA, tac, lpp, lac-lpp, lac, ara, trp, trc and T7 promoters.

3. The polynucleotide molecule of claim 2, wherein both promoters are PhoA promoters.

4. The polynucleotide molecule of claim 1, wherein each of the TIR-L and TIR-H comprises a prokaryotic secretion signal sequence or variant thereof.

5. The polynucleotide molecule of claim 4, wherein the prokaryotic secretion signal sequence is selected from the group consisting of STII, OmpA, PhoE, LamB, MBP and PhoA secretion signal sequences.

6. The polynucleotide molecule of claim 1, wherein the TIR-L and TIR-H provide approximately equal translational strengths.

7. The polynucleotide molecule of claim 6, wherein the relative translational strength combination is about (1-TIR-L, 1-TIR-H).

8. A recombinant vector for expressing an intact antibody in a prokaryotic host cell, said vector comprising the polynucleotide molecule of claim 1.

9. A prokaryotic host cell comprising the recombinant vector of claim 8.

10. The prokaryotic host cell of claim 9 which is a gram-negative bacterial cell.

11. The host cell of claim 10 which is E. coli.

12. The host cell of claim 11, further comprising a polynucleotide encoding at least one prokaryotic polypeptide selected from the group consisting of DsbA, DsbC, DsbG and FkpA.

13. The host cell of claim 12, wherein the polynucleotide encodes both DsbA and DsbC.

14. The host cell of claim 11, wherein the E. coli is of a strain deficient in endogenous protease activities.

15. The host cell of claim 14, wherein the genotype of the E. coli strain lacks degP and prc genes and harbors a mutant spr gene.

16. A process for producing a biologically active intact antibody in a prokaryotic host cell, said process comprising expressing in the host cell a polynucleotide comprising (1)

a first promoter and a first cistron forming a first promoter-cistron pair and (2) a second promoter and a second cistron forming a second promoter-cistron pair, wherein the first cistron of said first promoter-cistron pair comprises a first translational initiation region (TIR-L) operably linked to a nucleic acid sequence encoding an immunoglobulin light chain and the second cistron of said second promoter-cistron pair comprises a second translational initiation region (TIR-H) operably linked to a nucleic acid sequence encoding an immunoglobulin heavy chain, wherein upon expression of said polynucleotide, secreted light chain and heavy chain are folded and assembled to form a biologically active intact antibody; and recovering said intact antibody.

17. The process of claim 16, wherein the first and the second promoters are prokaryotic promoters selected from the group consisting of phoA, tac, lpp, lac-lpp, lac, ara, trp, trc and T7 promoters.

18. The process of claim 17, wherein both the first and the second promoters are PhoA promoters.

19. The process of claim 16, wherein each of the TIR-L and TIR-H comprises a prokaryotic secretion signal sequence or variant thereof.

20. The process of claim 19, wherein the prokaryotic secretion signal sequence is selected from the group consisting of STII, OmpA, PhoE, LamB, MBP and PhoA secretion signal sequences.

21. The process of claim 16, wherein the TIR-L and TIR-H provide approximately equal translational strengths.

22. The process of claim 21, wherein the relative translational strength combination is about (1-TIR-L, 1-TIR-H).

23. The process of claim 16, wherein the prokaryotic host cell is *E. coli*.

24. The process of claim 16, further comprising expressing in the prokaryotic host cell a polynucleotide encoding at least one prokaryotic polypeptide selected from the group consisting of DsbA, DsbC, DsbG and FkpA.

25. The process of claim 24, wherein the polynucleotide encodes both DsbA and DsbC.

26. The process of claim 23, wherein the *E. coli* is of a strain deficient in endogenous protease activities.

27. The process of claim 26, wherein the genotype of the *E. coli* lacks degP and prc genes and harbors a mutant spr gene.

* * * * *

UNITED STATES PATENT AND TRADEMARK OFFICE
CERTIFICATE OF CORRECTION

| | | |
|---|---|---|
| PATENT NO. | : 6,979,556 B2 | Page 1 of 1 |
| APPLICATION NO. | : 10/020786 | |
| DATED | : December 27, 2005 | |
| INVENTOR(S) | : Laura C. Simmons et al. | |

It is certified that error appears in the above-identified patent and that said Letters Patent is hereby corrected as shown below:

Title page, item (*) Notice: Patent Term Adjustment should read -- (221) days, instead of (157) days.--

Signed and Sealed this

Sixteenth Day of January, 2007

JON W. DUDAS
*Director of the United States Patent and Trademark Office*